(12) United States Patent
Kovach et al.

(10) Patent No.: US 10,023,587 B2
(45) Date of Patent: *Jul. 17, 2018

(54) OXABICYCLOHEPTANES AND OXABICYCLOHEPTENES, THEIR PREPARATION AND USE

(71) Applicant: LIXTE BIOTECHNOLOGY, INC., East Setauket, NY (US)

(72) Inventors: John S Kovach, East Setauket, NY (US); Francis Johnson, Setauker, NY (US)

(73) Assignee: Lixte Biotechnology, Inc., East Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,550

(22) Filed: Feb. 6, 2017

(65) Prior Publication Data

US 2017/0369503 A1   Dec. 28, 2017

Related U.S. Application Data

(60) Continuation of application No. 15/275,954, filed on Sep. 26, 2016, now abandoned, which is a continuation of application No. 15/150,129, filed on May 9, 2016, now abandoned, which is a continuation of application No. 15/004,525, filed on Jan. 22, 2016, now abandoned, which is a continuation of application No. 14/794,110, filed on Jul. 8, 2015, now abandoned, which is a continuation of application No. 14/328,384, filed on Jul. 10, 2014, now Pat. No. 9,079,917, which is a division of application No. 13/866,854, filed on Apr. 19, 2013, now Pat. No. 8,822,461, which is a continuation-in-part of application No. 13/174,249, filed on Jun. 30, 2011, now Pat. No. 8,426,444, which is a division of application No. 12/069,147, filed on Feb. 6, 2008, now Pat. No. 7,998,957.

(60) Provisional application No. 61/011,323, filed on Jan. 15, 2008, provisional application No. 60/964,904, filed on Aug. 14, 2007, provisional application No. 60/899,903, filed on Feb. 6, 2007.

(51) Int. Cl.
*C07D 493/08* (2006.01)
*A61K 31/496* (2006.01)
*A61K 31/203* (2006.01)

(52) U.S. Cl.
CPC .......... *C07D 493/08* (2013.01); *A61K 31/203* (2013.01); *A61K 31/496* (2013.01)

(58) Field of Classification Search
CPC .................................................. C07D 493/08
USPC ................................................... 514/254.11
See application file for complete search history.

(56) References Cited

U.S. PATENT DOCUMENTS

| | | |
|---|---|---|
| 2,957,906 A | 10/1960 | Erickson et al. |
| 3,980,674 A | 9/1976 | Kubela et al. |
| 4,143,054 A | 3/1979 | Sprague |
| 4,218,478 A | 8/1980 | Omura et al. |
| 4,298,752 A | 11/1981 | Dauben et al. |
| 4,463,015 A | 7/1984 | Haslanger et al. |
| 4,524,151 A | 6/1985 | Das et al. |
| 4,614,825 A | 9/1986 | Snitman et al. |
| 4,654,355 A | 3/1987 | Nakane et al. |
| 4,690,918 A | 9/1987 | Beppu et al. |
| 4,816,579 A | 3/1989 | Thottathil et al. |
| 4,851,423 A | 7/1989 | Girijavallabhan et al. |
| 4,851,553 A | 7/1989 | Thottathil |
| 5,266,710 A | 11/1993 | Patel et al. |
| 5,326,898 A | 7/1994 | Chandraratna |
| 5,763,647 A | 6/1998 | Ohtani et al. |
| 5,770,382 A | 6/1998 | Hwang et al. |
| 5,925,651 A | 7/1999 | Hutchinson |
| 5,968,965 A | 10/1999 | Dinsmore et al. |
| 6,222,055 B1 | 4/2001 | Wolter et al. |
| 6,632,823 B1 | 10/2003 | Vernier et al. |
| 6,696,483 B2 | 2/2004 | Singh |
| 6,706,762 B1 | 3/2004 | Evans et al. |
| 6,777,217 B1 | 8/2004 | Schreiber et al. |
| 6,905,669 B2 | 6/2005 | DiMartino et al. |
| 6,949,624 B1 | 9/2005 | Liu et al. |
| 7,067,551 B2 | 6/2006 | Remiszewski et al. |

(Continued)

FOREIGN PATENT DOCUMENTS

| DE | 19600707 A1 | 7/1997 |
|---|---|---|
| EP | 1443967 | 1/2007 |

(Continued)

OTHER PUBLICATIONS

Abel et al., "Epigenetic targets of HDAC inhibition in neurodegenerative and psychiatric disorders," Current Opinion in Pharmacology, vol. 8, No. 1, Feb. 2008 (pp. 57-64).

(Continued)

*Primary Examiner* — Taofiq A Solola
(74) *Attorney, Agent, or Firm* — Andrea L. C. Reid; Dechert LLP

(57) ABSTRACT

This invention provides compounds having the structure

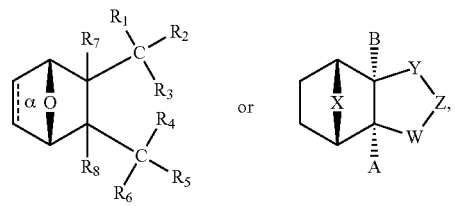

which may be used for the treatment of tumors.

3 Claims, 32 Drawing Sheets

(56) References Cited

U.S. PATENT DOCUMENTS

| | | |
|---|---|---|
| 7,154,002 B1 | 12/2006 | Bressi et al. |
| 7,998,957 B2 | 8/2011 | Kovach et al. |
| 8,058,268 B2 | 11/2011 | Kovach et al. |
| 8,227,473 B2 | 7/2012 | Kovach et al. |
| 2002/0115826 A1 | 8/2002 | Delorme et al. |
| 2002/0147345 A1 | 10/2002 | El Tayer et al. |
| 2002/0177692 A1 | 11/2002 | Bartel |
| 2003/0162186 A1 | 8/2003 | Bejanin et al. |
| 2004/0010045 A1 | 1/2004 | Yi |
| 2004/0053996 A1 | 3/2004 | Gesing et al. |
| 2004/0087657 A1 | 5/2004 | Richon et al. |
| 2004/0106141 A1 | 6/2004 | Mischel et al. |
| 2004/0116366 A1 | 6/2004 | Monia et al. |
| 2004/0122101 A1 | 6/2004 | Miller et al. |
| 2004/0161475 A1 | 8/2004 | Ellison et al. |
| 2004/0197888 A1 | 10/2004 | Armour et al. |
| 2004/0209934 A1 | 10/2004 | McCluskey et al. |
| 2004/0253637 A1 | 12/2004 | Buechler et al. |
| 2005/0014839 A1 | 1/2005 | Kozikowski et al. |
| 2005/0020831 A1 | 1/2005 | Inman et al. |
| 2005/0220831 A1 | 1/2005 | Inman et al. |
| 2005/0054626 A1 | 3/2005 | Carter et al. |
| 2005/0119229 A1 | 6/2005 | Ammermann et al. |
| 2005/0136090 A1 | 6/2005 | Falotico et al. |
| 2005/0171202 A1 | 8/2005 | Graupner et al. |
| 2005/0203082 A1 | 9/2005 | Hsu et al. |
| 2005/0215526 A1 | 9/2005 | Hulme et al. |
| 2005/0222013 A1 | 10/2005 | Jung et al. |
| 2005/0277583 A1 | 12/2005 | Yoshida et al. |
| 2005/0282893 A1 | 12/2005 | Au et al. |
| 2006/0030616 A1 | 2/2006 | McCluskey et al. |
| 2006/0117994 A1 | 6/2006 | Ryu et al. |
| 2006/0134682 A1 | 6/2006 | Roberts et al. |
| 2006/0167103 A1 | 7/2006 | Bacopoulos et al. |
| 2006/0235231 A1 | 10/2006 | Joel et al. |
| 2006/0264415 A1 | 11/2006 | Leit de Moradei et al. |
| 2007/0004771 A1 | 1/2007 | Lee et al. |
| 2007/0010669 A1 | 1/2007 | Breslow et al. |
| 2007/0049576 A1 | 3/2007 | Barlow et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2008/0132503 A1 | 6/2008 | Moradei et al. |
| 2008/0214569 A1 | 9/2008 | Zhuang et al. |
| 2009/0012066 A1 | 1/2009 | Izumo et al. |
| 2009/0018142 A9 | 1/2009 | Zhuang et al. |
| 2009/0035292 A1 | 2/2009 | Kovach et al. |
| 2009/0036309 A1 | 2/2009 | Kovach et al. |
| 2009/0143445 A1 | 6/2009 | Kovach et al. |
| 2010/0029484 A1 | 2/2010 | Kovach et al. |
| 2010/0029640 A1 | 2/2010 | Kovach et al. |
| 2010/0029683 A1 | 2/2010 | Kovach et al. |
| 2011/0287537 A1 | 11/2011 | Kovach et al. |
| 2012/0135522 A1 | 5/2012 | Kovach |
| 2012/0270736 A1 | 10/2012 | Kovach et al. |
| 2013/0302402 A1 | 11/2013 | Kovach et al. |

FOREIGN PATENT DOCUMENTS

| | | |
|---|---|---|
| FR | 2872704 | 1/2006 |
| JP | 5069091 | 10/1973 |
| JP | 5188631 | 1/1975 |
| JP | 5198755 | 1/1975 |
| JP | 51032733 A | 3/1976 |
| JP | 2256650 | 12/1989 |
| JP | 10504305 | 2/1996 |
| JP | 2002520415 | 1/2000 |
| JP | 2001329061 | 6/2000 |
| JP | 2004531500 | 10/2002 |
| JP | 2006519609 | 9/2004 |
| JP | 2005507852 | 3/2005 |
| JP | 2007511528 | 3/2007 |
| JP | 2007514665 | 6/2007 |
| RU | 201598 | 7/1994 |
| SU | 1553533 | 3/1990 |
| WO | WO-2000004023 A1 | 1/2000 |
| WO | WO-2002042310 A2 | 5/2002 |
| WO | WO-2002076989 A1 | 10/2002 |
| WO | WO-2003092616 A2 | 11/2003 |
| WO | WO-2005018673 | 3/2005 |
| WO | WO-2005049084 | 6/2005 |
| WO | WO 2005054257 | 6/2005 |
| WO | WO-2005058280 | 6/2005 |
| WO | WO-2005074941 | 8/2005 |
| WO | WO-2006023603 | 3/2006 |
| WO | WO-2006129105 | 12/2006 |
| WO | WO-2007014029 | 2/2007 |
| WO | WO-2007021682 | 2/2007 |
| WO | WO-2007092414 | 9/2007 |
| WO | WO-2007118137 | 10/2007 |
| WO | WO-2008028965 A2 | 3/2008 |
| WO | WO-2008030617 A2 | 3/2008 |
| WO | WO-2008058342 A1 | 5/2008 |
| WO | WO-2008097561 A1 | 8/2008 |
| WO | WO-2009020565 | 2/2009 |
| WO | WO-2009045440 | 4/2009 |
| WO | WO-2010014220 | 2/2010 |
| WO | WO-2010014254 | 2/2010 |
| WO | WO-2010147612 | 12/2010 |

OTHER PUBLICATIONS

Acharya et al., "Rational development of histone deacetylase inhibitors as anticancer agents: a review," Molecular Pharmacology, vol. 68, No. 4, Oct. 2005 (pp. 917-932).

Adcock, "HDAC inhibitors as anti-inflammatory agents," British Journal of Pharmacology, vol. 150, No. 7, Apr. 2007 (pp. 829-831).

Advisory Action dated Feb. 22, 2012 in connection with U.S. Appl. No. 12/460,404.

Advisory Action dated Jan. 13, 2012 in connection with U.S. Appl. No. 12/221,360.

Albert, "Changing the trajectory of cognitive decline," New England Journal of Medicine, vol. 357, No. 5, Aug. 2007 (pp. 502-503).

Amendment in Response to Dec. 12, 2012 Communication pursuant to Art. 94(3) EPC filed Apr. 22, 2013 with the European Patent Office in connection with European Patent Application No. 08725214.4.

Amendment in Response to Dec. 6, 2012 Office Action filed Dec. 10, 2013 in connection with Australian Patent Application No. 2008214299.

Amendment in Response to Jan. 4, 2011 Office Action filed Feb. 16, 2011 in connection with U.S. Appl. No. 12/069,147.

Amendment in Response to Mar. 9, 2011 Supplemental European Search Report filed Sep. 26, 2011 with the European Patent Office in connection with European Patent Application No. 08725214.4.

Amendment in Response to Oct. 26, 2010 Office Action and Supplemental Information Disclosure Statement filed Nov. 26, 2010 in connection with U.S. Appl. No. 12/069,147.

Amendment Under 37 C.F.R. 1.132 and Supplemental Information Disclosure Statement Pursuant to 37 C.F.R. 197(d) and Statement Under 37 C.F.R. 1.97(e)(1) filed Jan. 11, 2013 in connection with U.S. Appl. No. 13/174,249.

Andrabi et al., "B. Protein Phosphatase 2A regulates Life and death decisions via Akt in a context-dependent manner," Proc. Natl. acad. Sci USA 10:19011-19016.

Andrabi et at, "Protein phosphatase 2A regulates life and death decisions via Akt in a context-dependent manner," Proceedings of the National Academy of Sciences U.S.A., vol. 104, No. 48, Nov. 2007 (pp. 19011-19016).

Australian Office Action dated Dec. 6, 2012 in connection with Australian Patent Application No. 2008214299.

Avila et al. "Tau Phosphorylation, Aggregation, and Cell Toxicity," Journal of Biomedicine and Biotechnology, vol. 2006, No Month Listed 2006 (pp. 1-5).

Ayaydin et al., "Inhibition of serine/threonine-specific protein phosphatases causes premature activation of cdc2MsF kinase at

(56) References Cited

OTHER PUBLICATIONS

G2/M transition and early mitotic microtubule organisation in alfalfa," The Plant Journal, vol. 23, No. 1, Jul. 2000 (pp. 85-96).
Baskin et al., "Inhibitors of protein kinases and phosphatases alter root morphology and disorganize cortical microtubules," Plant Physiology, vol. 113, No. 2, Feb. 1997 (pp. 493-502).
Bastien et al., "Nuclear retinoid receptors and the transcription of retinoid-target genes," Gene, vol. 328, Mar. 2004 (pp. 1-16).
Beglopoulos et al., "Regulation of CRE-dependent transcription by presenilins: prospects for therapy of Alzheimer's disease," Trends in Pharmacological Sciences, vol. 27, No. 1, Jan. 2006 (pp. 33-40).
Berthold et al., "Myeloablative megatherapy with autologous stem-cell rescue versus oral maintenance chemotherapy as consolidation treatment in patients with high-risk neuroblastoma: a randomised controlled trial," The Lancet Biology, vol. 6, No. 9, Sep. 2005 (pp. 649-658).
Bertini et al., "Structural basis of serine/threonine phosphatase inhibition by the archetypal small molecules cantharidin and norcantharidin," Journal of Medicinal Chemistry, vol. 52, No. 15, Aug. 2009 (pp. 4838-4843).
Blaheta et al., "Valproate and valproate-analogues: potent tools to fight against cancer," Current Medicinal Chemistry, vol. 9, No. 15, Aug. 2002 (pp. 1417-1433).
Blaskovich et al., "Recent discovery and development of protein tyrosince phosphatase inhibitors," Expert Opinion on Therapeutic Patents, vol. 12, No. 6, Jun. 2002 (pp. 871-905).
Bommer et al., "The translationally controlled tumor protein TCTP," International Journal of Biochemistry and Cell Biology, vol. 36, No. 3, Mar. 2004 (pp. 379-385).
Bonness et al., "Cantharidin-induced mitotic arrest is associated with the formation of aberrant mitotic spindles and lagging chromosomes resulting, in part, from the suppression of PP2Aa," Molecular Cancer Therapeutics, vol. 5, No. 11, Nov. 2006 (pp. 2727-2736).
Brazil et al., "Advances in protein kinase B signalling: AKTion on multiple fronts," Trends in Biochemical Sciences, vol. 29, No. 5, May 2004 (pp. 233-242).
Burke, "Inhibition of mitogen-activated protein kinase and stimulation of Akt kinase signaling pathways: Two approaches with therapeutic potential in the treatment of neurodegenerative disease," Pharmacology & Therapeutics, vol. 114, No. 3, Jun. 2007 (pp. 261-277).
Camphausen et al., "Influence of in vivo growth on human glioma cell line gene expression: convergent profiles under orthotopic conditions," Proceedings of the National Academy of Sciences U.S.A., vol. 102, No. 23, Jun. 2005 (pp. 8287-8292).
CAS Registry No. 61531-23-5, Nov. 16, 1984 (discussed in the Dec. 6, 2012 Australian Office Action issued I connection with Australian Patent Application No. 2008214299).
Castedo et al., "Cell death by mitotic catastrophe: a molecular definition," Oncogene, vol. 23, No. 16, Apr. 2004 (pp. 2825-2837).
Chang et al., "All-trans-retinoic acid induces cell growth arrest in a human medullablastoma cell line," Journal of Neuro-Oncology, vol. 84, No. 3, Sep. 2007 (pp. 263-267).
Chen et al., "A knockout mouse approach reveals that TCTP functions as an essential factor for cell proliferation and survival in a tissue or cell type specific manner," Molecular Biology of the Cell, vol. 18, No. 7, Jul. 2007 (pp. 2525-2532).
Chen et al., "Mcl-1 Down-regulation Potentiates ABT-737 Lethality by Cooperatively Inducing Bak Activation and Bax Translocation," Cancer Research, vol. 67, No. 2, Jan. 2007 (pp. 782-791).
Chinese Office Action dated Jan. 14, 2013 in connection with Chinese Patent Application No. 200880004292.9, including English language translation provided by Chinese agent.
Chinese Office Action dated May 21, 2012 in connection with Chinese Patent Application No. 200880004292.9 including English language translation provided by Chinese agent.
Cho et al., "Crystal structure of a protein phosphatase 2A heterotrimeric holoenzyme," Nature, vol. 445, No. 7123, Jan. 2007 (pp. 53-57).

Communication pursuant to Art. 94(3) EPC dated Dec. 12, 2012 in connection with European Patent Application No. 08725214.4, filed Feb. 6, 2008.
Communication pursuant to Art. 94(3) EPC dated Jan. 30, 2013 in connection with European Patent Application No. 09803283.2, filed Jan. 24, 2011.
Communication pursuant to Art. 94(3) EPC dated Jul. 16, 2013 in connection with European Patent Application No. 09803283.2, filed Jan. 24, 2011.
Communication pursuant to Rules 70(2) and 70a(2) EPC dated Mar. 28, 2011 in connection with European Patent Application No. 08725214.4, filed Sep. 2, 2009.
Crafts, "Herbicides," Annual Review of Plant Physiology, vol. 4, Jun. 1953 (pp. 253-282).
Craig, "MCL1 provides a window on the role of the BCL2 family in cell proliferation, differentiation and tumorigenesis," Leukemia, vol. 16, No. 4, Apr. 2002 (pp. 444-454).
D'Adda di Fagagna, "Living on a break: cellular senescence as a DNA-damage response," Nature Reviews Cancer, vol. 8, No. 7, Jul. 2008 (pp. 512-522).
David et al., "Histone deacetylase associated with mSin3A mediates repression by the acute promyelocytic leukemia-associated PLZF protein," Oncogene, vol. 16, No. 19, May 1998 (pp. 2549-2556).
Decision of Rejection issued Aug. 22, 2013 by the Chinese Patent Office in connection with Chinese Patent Application No. 200880004292.9 (including English language summary provided by Chinese agent).
Dreesen et al., "Signaling pathways in cancer and embryonic stem cells," Stem Cell Review, vol. 3, No. 1, Jan. 2007 (pp. 7-17).
Drewinko et al., "Combination chemotherapy in vitro with adriamycin. Observations of additive, antagonistic, and synergistic effects when used in two-drug combinations on cultured human lymphoma cells," Cancer Biochemistry Biophysics, vol. 1, No. 4, May 1976 (pp. 187-195).
Erdodi et al., "Endothall thianhydride inhibits protein phosphatases-1 and -2A in vivo," American Journal of Physiology—Cell Physiology, vol. 269, No. 5, Nov. 5 (pp. C1176-C1184).
Essers et al., "Synthesis of the first fluorinated cantharidin analogues," Tetrahedron Letters, vol. 42, No. 32, Aug. 2001 (pp. 5429-5433).
Eurasian Official Action dated Feb. 15, 2013 in connection with Eurasian Patent Application No. 200970737 with English translation.
Eurasian Official Action dated Jun. 22, 2011 in connection with Eurasian Paten Application No. 200970737 with English Translation.
Eurasian Official Action dated Jun. 7, 2013 in connection with Eurasian Patent Application No. 201170288, filed Jul. 30, 2009 (including English language summary provided by Eurasian agent).
Eurasian Official Action dated May 24, 2012 in connection with Eurasian Patent Application No. 200970737 with English translation.
Eurasian Official Action dated Nov. 19, 2009 in connection with Eurasian Patent Application No. 200970737.
Eurasian Official Action dated Nov. 19, 2012 in connection with Eurasian Patent Application No. 201170288, filed Jul. 30, 2009 with English translation.
Eurasian Official Action dated Sep. 19, 2013 in connection with Eurasian Patent Application No. 200970737 (including English language summary provided by Eurasian agent).
European Search Report dated Mar. 9, 2011 in connection with European Patent Application No. 08725214.4, filed Sep. 2, 2009.
Fabel et al., "Long-term stabilization in patients with malignant glioma after treatment with liposomal doxorubicin," Cancer, vol. 92, No. 7, Oct. 2001 (pp. 1936-1942).
Fanghanel et al., "Cycloaddition Reactions of [1,]Dithiolo [1,2] dithiole Derivatives with Dimethyl Acetylenedicarboxylate: Formation of New Bi-, Tri- and Tetracyclic Thiopyran Derivatives," Synthesis, vol. 10, No Month Listed 1994 (pp. 1067-1071).
Final Office Action dated Dec. 15, 2011 in connection with U.S. Appl. No. 12/460,404.
Final Office Action dated Mar. 20, 2013 in connection with U.S. Appl. No. 13/493,816.

(56) References Cited

OTHER PUBLICATIONS

Final Office Action dated Nov. 2, 2011 in connection with U.S. Appl. No. 12/221,360.
Firmin et al., "Structures of a histone deacetylase homologue bound to the TSA and SAHA inhibitors," Nature, vol. 401, No. 6749, Sep. 1999 (pp. 188-193).
First Examiner's Report dated Sep. 27, 2013 by the Australian Patent Office in connection with Australian Patent Application No. 2009277031, filed Jan. 11, 2011.
First Official Action dated Jul. 1, 2013 in connection with Chinese Patent Application No. 200980130568.2 (including English language summary provided by Chinese agent).
Fischer et al., "Recovery of learning and memory is associated with chromatin remodelling," Nature, vol. 447, No. 7141, May 2007 (pp. 178-182).
Flicker et al., "Tyrosine kinase signaling pathways control the expression of retinoic acid receptor-alpha in SK-BR-3 breast cancer cells," Cancer Letters, vol. 115, No. 1, May 1997 (pp. 63-72).
Forester et al., "Control of mitotic exit by PP2A regulation of Cdc25C and Cdk1," Proceedings of the National Academy of Sciences U.S.A., vol. 104, No. 50, Dec. 2007 (pp. 19867-19872).
Furumai et al., "Potent histone deacetylase inhibitors built from trichostatin A and cyclic tetrapeptide antibiotics including trapoxin," Proceedings of the National Academy of Sciences U.S. A., vol. 98, No. 1, Jan. 2001 (pp. 87-92).
Gachet et al., "The growth-related, translationally controlled protein P23 has properties of a tubulin binding protein and associates transiently with microtubules during the cell cycle," Journal of Cell Science, vol. 112, pt. 8, Apr. 1999 (pp. 1257-1271).
Garcia-Echeverria et al., "Drug discovery approaches targeting the PI3K/Akt pathway in cancer," Oncogene, vol. 27, No. 41, Sep. 2008 (pp. 5511-5526).
Giannini et al., "Expression analysis of a subset of coregulators and three nuclear receptors in human colorectal carcinoma," Anticancer Research, vol. 25, No. 6B, Nov. 2005 (pp. 4287-4292).
Gottlicher et al., "Valproic acid defines a novel class of HDAC inhibitors inducing differentiation of transformed cells," EMBO Journal, vol. 20, No. 24, Dec. 2001 (pp. 6969-6978).
Graziano et al., "Comparison of the acute toxicity of endothal and cantharidic acid on mouse liver in vivo," Toxicology Letters, vol. 37, No. 2, Jul. 1987 (pp. 143-148).
Gumireddy et al., "All-trans-retinoic acid-induced apoptosis in human medulloblastoma: activation of caspase-3/poly (ADP-ribose) polymerase 1 pathway," Clinical Cancer Research, vol. 9, No. 11, Sep. 2003 (pp. 4052-4059).
Hart et al., "Modified norcantharidins; synthesis, protein phosphatases 1 and 2A inhibition, and anticancer activity, Bioorganic and Medicinal Chemistry Letters, vol. 14, No. 8, Apr. 2004 (pp. 1969-1973).
Havrilesky et al., "Relationship between expression of coactivators and corepressors of hormone receptors and resistance of ovarian cancers to growth regulation by steroid hormones," Journal of Society of Gynecologic Investigation, vol. 8, No. 2, Mar. 2001 (pp. 104-113).
Hermanson et al., "N-CoR controls differentiation of neural stem cells into astrocytes," Nature, vol. 419, No. 6910, Oct. 2002 (pp. 934-939).
Hildmann et al., "Histone-deacetylases—an important class of cellular regulators with a variety of functions," Applied Microbiology and Biotechnology, vol. 75, No. 3, Jun. 2007 (pp. 487-497).
Hill et al., "Heterocyclic substituted cantharidin and norcantharidin analogues—synthesis, protein phosphatase (1 and 2A) inhibition, and anti-cancer activity," Bioorganic and Medicinal Chemistry, vol. 17, No. 12, Jun. 2007 (pp. 3392-3397).
Hirose et al., "Akt activation suppresses Chk2-mediated methylating agent-induced G2 arrest and protects from temozolomide-induced mitotic catastrophe and cellular senescence," Cancer Research, vol. 65, No. 11, Jun. 2005 (pp. 4861-4869).
Hong et al., "Norcantharidin-Induced Post-G2/M Apoptosis Is Dependent on Wild-Type p53 Gene," Biochemical and Biophysical Research Communications, vol. 276, No. 1, Sep. 2000 (pp. 278-285).
Honkanen, "Cantharidin, another natural toxin that inhibits the activity of serine/threonine protein phosphatases types 1 and 2A," FEBS Letters, vol. 330, No. 30, Sep. 1993 (pp. 283-286).
Hoshikawa et al., "Trichostatin A induces morphological changes and gelsolin expression by inhibiting histone deacetylase in human carcinoma cell lines," Experimental Cell Research, vol. 214, No. 1, Sep. 1994 (pp. 189-197).
Huang, "Targeting histone deacetylases for the treatment of cancer and inflammatory diseases," Journal of Cell Physiology, vol. 209, No. 3, Dec. 2006 (pp. 611-616).
Hughes et al., "Ciliary neurotrophic factor induces type-2 astrocyte differentiation in culture," Nature, vol. 335, No. 6185, Sep. 1988 (pp. 70-73).
Ianzini et al., "Delayed DNA damage associated with mitotic catastrophe following X-irradiation of HeLa S3 cells," Mutagenesis, vol. 13, No. 4, Jul. 1998 (pp. 337-344).
International Preliminary Report on Patentability in connection with PCT/US2008/011367, dated Apr. 7, 2010.
International Preliminary Report on Patentability in connection with PCT/US2009/004430, dated Feb. 1, 2011.
International Preliminary Report on Patentability issued by the United States Patent and Trademark Office as International Searching Authority for International Patent Application No. PCT/US2007/003095 dated Aug. 12, 2008 (7 pages).
International Preliminary Report on Patentability issued by the United States Patent and Trademark Office as International Searching Authority for International Patent Application No. PCT/US2008/001549 dated Aug. 11, 2009 (6 pages).
International Preliminary Report on Patentability issued by the United States Patent and Trademark Office as International Searching Authority for International Patent Application No. PCT/US2008/009330 dated Nov. 4, 2008 (6 pages).
International Preliminary Report on Patentability issued by the United States Patent and Trademark Office as International Searching Authority for International Patent Application No. PCT/US2010/000279 dated Dec. 20, 2011 (7 pages).
International Search Report and Written Opinion issued by the United States Patent and Trademark Office as International Searching Authority for International Patent Application No. PCT/US2007/003095 dated Feb. 14, 2008 (13 pages).
International Search Report and Written Opinion issued by the United States Patent and Trademark Office as International Searching Authority for International Patent Application No. PCT/US2008/001549 dated May 16, 2008 (7 pages).
International Search Report and Written Opinion issued by the United States Patent and Trademark Office as International Searching Authority for International Patent Application No. PCT/US2008/009330 dated Nov. 4, 2008 (7 pages).
International Search Report and Written Opinion issued by the United States Patent and Trademark Office as International Searching Authority for International Patent Application No. PCT/US2010/000279 dated May 3, 2010 (8 pages).
International Search Report in connection with PCT/US2008/011367, dated Dec. 12, 2008.
International Search Report in connection with PCT/US2009/004108, dated Sep. 15, 2009.
International Search Report in connection with PCT/US2009/004378, dated Sep. 18, 2009.
International Search Report in connection with PCT/US2009/004430, dated Jan. 12, 2010.
Janssens et al., "Protein phosphatase 2A: a highly regulated family of serine/threonine phosphatases implicated in cell growth and signalling," The Biochemical Journal, vol. 353, Pt. 3, Feb. 2001 (pp. 417-439).
Japanese Office Action dated Jan. 22, 2013 in connection with Japanese Patent Application No. 2009-549092.
Japanese Office Action dated Sep. 10, 2013 in connection with Japanese Patent Application No. 2009-549092 (including English language summary provided by Japanese agent).

(56) References Cited

OTHER PUBLICATIONS

Johnson et al., 37 Plk1 activation by Ste20-like kinase (Slk) phosphorylation and polo-box phosphopeptide binding assayed with the substrate translationally controlled tumor protein (TCTP), Biochemistry, vol. 47, No. 12, Mar. 2008 (pp. 3688-3696).

Joshi et al., "Retinoic acid receptors and tissue-transglutaminase mediate short-term effect of retinoic acid on migration and invasion of neuroblastoma SH-SY5Y cells," Oncogene, vol. 25, No. 2, Jan. 2006 (pp. 240-247).

Jul. 4, 2013 Communication pursuant to Article 94(3) EPC issued by the European Patent Office in connection with European Patent Application No. 08794986.3.

Kamitani et al., "Histone acetylation may suppress human glioma cell proliferation when p21 WAF/Cip1 and gelsolin are induced," Neuro-Oncology, vol. 4, No. 2, Apr. 2002 (pp. 95-101).

Kawamura et al., "Endothall thioanhydride: structural aspects of unusually high mouse toxicity and specific binding site in liver," Chemical Research in Toxicology, vol. 3, No. 4, Jul. 1990 (pp. 318-324).

Kayser et al., "Metal hydride reductions of unsymmetrical cyclic anhydrides. The importance of the antiperiplanar effect on the regioselectivity of these reactions," Canadian Journal of Chemistry, vol. 60, No. 10, May 1982 (pp. 1192-1198).

Kayser et al., "On the regioselectivity of Wittig reactions with unsymmetrically substituted succinic anhydrides," Canadian Journal of Chemistry, vol. 67, No. 9, Sep. 1989 (pp. 1401-1410).

Kelly et al., "Drug insight: Histone deacetylase inhibitors-development of the new targeted anticancer agent suberoylanilide hydroxamic acid," Nature Clinical Practice Oncology, vol. 2, No. 3, Mar. 2005 (pp. 150-157).

Kijima et al., "Trapoxin, an antitumor cyclic tetrapeptide, is an irreversible inhibitor of mammalian histone deacetylase," Journal of Biological Chemistry, vol. 268, No. 30, Oct. 1993 (pp. 22429-22435).

Kim et al., "Selective Induction of cyclin-Dependent Kinase Inhibitors and Their Roles in Cell Cycle Arrest Caused by Trichostatin A, an Inhibitor of Histone Deacetylase," Annals of the New York Academy of Sciences, vol. 886, Dec. 1999 (pp. 200-203).

Kim et al., "Susceptibility and radiosensitization of human glioblastoma cells to trichostatin A, a histone deacetylase inhibitor," International Journal of Radiation Oncology, Biology, Physics, vol. 59, No. 4, Jul. 2004 (pp. 1174-1180).

King, "Bioisosteres, Conformational Restriction and Pro-drugs: Approaches to Lead Optimisation—Case history: An Example of a Conformational Restriction Approach," Medicinal Chemistry: Principles and Practice, Chapter 14, No Month Listed 1994 (pp. 206-209).

Kitamura et al., "Histone deacetylase inhibitor but not arsenic trioxide differentiates acute promyelocytic leukaemia cells with t(11;17) in combination with all-trans retinoic acid," British Journal of Haematology, vol. 108, No. 4, Mar. 2000 (pp. 696-702).

Korzus et al., "CBP histone acetyltransferase activity is a critical component of memory consolidation," Neruon, vol. 42, No. 6, Jun. 2004 (pp. 961-972).

Kovach et al., "Enhancement of the antiproliferative activity of human interferon by polyamine depletion," Cancer Treatment Reports, vol. 69, No. 1, Jan. 1985 (pp. 97-103).

Kozikowski et al., "Functional differences in epigenetic modulators-superiority of mercaptoacetamide-based histone deacetylase inhibitors relative to hydroxamates in cortical neuron neuroprotection studies," Journal of Medicinal Chemistry, vol. 50, No. 13, Jun. 2007 (pp. 3054-3061).

Kurebayashi et al., "Expression levels of estrogen receptor-alpha, estrogen receptor-beta, coactivators, and corepressors in breast cancer," Clinical Cancer Research, vol. 6, No. 2, Feb. 2000 (pp. 512-518).

Kwon et al., "Depudecin induces morphological reversion of transformed fibroblasts via the inhibition of histone deacetylase," Proceedings of the National Academy of Sciences U.S.A., vol. 95, No. 7, Mar. 1998 (pp. 3356-3361).

Langley et al., "Pulse inhibition of histone deacetylases induces complete resistance to oxidative death in cortical neurons without toxicity and reveals a role for cytoplasmic p21(wafl/cipl) in cell cycle-independent neuroprotection," Journal of Neuroscience, vol. 28, No. 1, Jan. 2008 (pp. 163-176).

Lavinsky et al., "Diverse signaling pathways modulate nuclear receptor recruitment of N-CoR and SMRT complexes," Proceedings of the National Academy of Sciences U.S.A., vol. 95, No. 6, Mar. 1998 (pp. 2920-2925).

Lei et al., "Plk1 depletion in nontransformed diploid cells activates the DNA-damage checkpoint," Oncogene, vol. 27, No. 28, Jun. 2008 (pp. 3935-3943).

Levenson et al., "Regulation of histone acetylation during memory formation in the hippocampus," Journal of Biological Chemistry, vol. 279, No. 39, Sep. 2004 (pp. 40545-40559).

Levesque, "Reduction of L-DOPA-induced dyskinesias by retinoid agonists: a new way to improve Parkinson's disease treatment," The Parkinson Alliance, 2004 Pilot Study Grants, abstract only.

Li et al., "Cantharidin-binding protein: identification as protein phosphatase 2A," Proceedings of the National Academy of Sciences U.S.A., vol. 89, No. 24, Dec. 1992 (pp. 11867-11870).

Li et al., "Protein phosphatase 2A and its[3H]cantharidin/[3H]endothall thioanhydride binging site. Inhibitor specificity of cantharidin and ATP analogues," Biochemical Pharmacology, vol. 46, No. 8, Oct. 1993 (pp. 1435-1443).

Li et al., "Valproic acid induces growth arrest, apoptosis, and senescence in medulloblastomas by increasing histone hyperacetylation and regulating expression of p21Cipl, CDK4, and CMYC," Molecular Cancer Therapeutics, vol. 4, No. 12, Dec. 2005 (pp. 1912-1922).

Lim et al., "Tumour maintenance is mediated by eNOS," Nature, vol. 452, Apr. 2008 (pp. 646-649).

Lin et al., "Role of the histone deacetylase complex in acute promyelocytic leukaemia," Nature, vol. 391, No. 6669, Feb. 1998 (pp. 811-814).

Liu et al., "Normal cells, but not cancer cells, survive severe Plk1 depletion," Molecular and Cellular Biology, vol. 26, No. 6, Mar. 2006 (pp. 2093-2108).

Liu et al., "Stabilization and enhancement of the antiapoptic activity of Mcl-1 by TCTP," Molecular and Cellular Biology, vol. 25, No. 8, Apr. 2005 (pp. 3117-3126).

Lopez-Pajares et al., "Phosphorylation of MDMX mediated by Akt leads to stabilization and induces 14-3-3 binding," Journal of Biological Chemistry, vol. 283, No. 20, May 2008 (pp. 13707-13713).

Lu et al., "Aqueous ring-opening metathesis polymerization and copolymerization of 2,3-dicarboxylic acid anhydride, 2,3-bis(methoxymethyl) and 2,3-dicarboxylic acid monomethyl ester derivatives of 7-oxanorbornene," European Polymer Journal, vol. 29, No. 2-3, Feb.-Mar. 1993 (pp. 269-279).

Lu et al., "Aqueous ring-opening metathesis polymerization of 7-oxanorbornene derivatives with oxygen-containing functionalities," Macromolecular Chemistry and Physics, vol. 195, No. 4, Apr. 1994 (pp. 1273-1288).

Lu et al., "LB-1, an inhibitor of serine-threonine protein phosphatase PP2A, suppresses the growth of glioblastoma cells in vitro and in vivo," AACR Annual Meeting, Apr. 12-16, 2008, San Diego, CA, vol. 68, No. 9, May 2008 (Abstract #5693).

Managan et al, "Turning Back the Clock on Neurodegeneration," Cell, vol. 129, No. 5, Jun. 2007 (pp. 851-853).

Manka et al., "Retro Diels-Alder Reactions of 5,6-Disbustituted-7-oxabicyclo[2.2.1]hept-2-enes: Experimental and Density Functional Theory Studies," Journal of Organic Chemistry, vol. 65, No. 17, Aug. 2000 (pp. 5202-5206).

Mardor et al., "Monitoring response to convection-enhances taxol delivery in brain tumor patients using diffusion-weighted magnetic resonance imaging," Cancer Research, vol. 61, No. 13, Jul. 2001 (pp. 4971-4973).

Marks et al., "Histone deacetylases," Current Opinion in Pharmacology, vol. 3, No. 4, Aug. 2003 (pp. 344-351).

(56) References Cited

OTHER PUBLICATIONS

Matsuzawa et al., "Endothal and cantharidin analogs: relation of structure to herbicidal activity and mammalian toxicity," Journal of Agricultural and Food Chemistry, vol. 35, No. 5, Sep. 1987 (pp. 823-829).
Matthay et al., "Treatment of High-Risk Neuroblastoma and Intensive Chemotherapy, Radiotherapy, Autologous Bone Marrow Transplantation, and 13-cis-Retinoic Acid," New England Journal of Medicine, vol. 341, Oct. 1999 (pp. 1165-1173).
May 15, 2013 Office Action in connection with U.S. Appl. No. 13/378,623.
McCluskey et al., "Anhydride modified cantharidin analogues. Is ring opening important in the inhibition of protein phosphatase 2A?," European Journal of Medicinal Chemistry, vol. 35, No. 10, Oct. 2000 (pp. 957-964).
McCluskey et al., "Anhydride modified cantharidin analogues: synthesis, inhibition of protein phosphatases 1 and2A and anticancer activity," Bioorganic and Medicinal Chemistry Letters, vol. 10, No. 15, Aug. 2000 (pp. 1687-1690).
McCluskey et al., "Inhibition of Protein Phosphatase 2A by Cantharidin Analogues," Bioorganic and Medicinal Chemistry Letters, vol. 6, No. 9, May 1996 (pp. 1025-1028).
Mexican Office Action dated Aug. 15, 2012 in connection with Mexican Patent Application No. MX/a/2009/008347 including English language summary provided by Mexican agent.
Mexican Office Action dated Jan. 24, 2013 in connection with Mexican Patent Application No. MX/a/2009/008347 including English language summary provided by Mexican agent.
Mexican Office Action dated Jul. 19, 2012 in connection with Mexican Patent Application No. MX/a/2011/001007, filed Jan. 26, 2011 including language summary provided by Mexican agent.
Mexican Office Action dated Jun. 4, 2012 in connection with Mexican Patent Application No. MX/a/2009/008347 including English language summary provided by Mexican agent.
Mexican Office Action dated Mar. 23, 2012 in connection with Mexican Patent Application No. MX/a/2009/008347 including English language summary provided by Mexican agent.
Mexican Office Action dated Mar. 25, 2013 in connection with Mexican Patent Application No. MX/a/2011/001007, filed Jan. 26, 2011 including English language summary provided by Mexican agent.
Mexican Office Action dated Sep. 25, 2012 in connection with Mexican Patent Application No. MX/a/2011/001007, filed Jan. 26, 2011 including English language summary provided by Mexican agent.
Mielnicki et al., "Epigenetic regulation of gelsolin expression in human breast cancer cells," Experimental Cell Research, vol. 249, No. 1, May 19999 (pp. 161-176).
Momparler, "In vitro systems for evaluation of combination chemotherapy," Pharmacology and Therapeutics, vol. 8, No. 1, No Month Listed 1980 (pp. 21-35).
Morse et al., "Docetaxel induces cell death through mitotic catastrophe in human breast cancer cells," Molecular Cancer Therapeutics, vol. 4, No. 10, Oct. 2005 (pp. 1495-1504).
Myers et al., "Associations and Interactions between Ets-1 and Ets-2 and Coregulatory Proteins, Src-1, AIB1, and NCoR in Breast Cancer," Clinical Cancer Research, vol. 11, Mar. 2005 (pp. 2111-2122).
National Library of Medicine, Medical Subject Headings (MeSH): Phosphatases (2009).
Neviani et al., "FTY720, a new alternative for treating blast crisis chronic myelogenous leukemia and Philadelphia chromosome-positive acute lymphocytic leukemia," Journal of Clinical Investigation, vol. 117, No. 9, Sep. 2007 (pp. 2408-2421).
Ngan et al., "Oxaliplatin induces mitotic catastrophe and apoptosis in esophageal cancer cells," Cancer Science, vol. 99, No. 1, Jan. 2008 (pp. 129-139).
Non-final Office Action dated Aug. 20, 2012 in connection with U.S. Appl. No. 13/174,249.
Non-final Office Action dated Aug. 3, 2011 in connection with U.S. Appl. No. 12/460,404.
Non-Final Office Action dated Dec. 10, 2008 in connection with U.S. Appl. No. 11/703,401.
Non-Final Office Action dated Dec. 10, 2009 in connection with U.S. Appl. No. 11/703,401.
Non-final Office Action dated Feb. 16, 2011 in connection with U.S. Appl. No. 12/221,360.
Non-final Office Action dated Feb. 16, 2011 in connection with U.S. Appl. No. 12/460,407.
Non-final Office Action dated Jan. 4, 2011 in connection with U.S. Appl. No. 12/069,147.
Non-Final Office Action dated Mar. 30, 2009 in connection with U.S. Appl. No. 11/703,401.
Non-Final Office Action dated May 26, 2011 in connection with U.S. Appl. No. 12/221,360.
Non-final Office Action dated Nov. 20, 212 in connection with U.S. Appl. No. 13/493,816.
Non-final Office Action dated Oct. 26, 2010 in connection with U.S. Appl. No. 12/069,147.
Non-final Office Action dated Sep. 30, 2010 in connection with U.S. Appl. No. 12/460,407.
Notice of Allowance dated Dec. 28, 2012 in connection with U.S. Appl. No. 13/174,249.
Notice of Allowance dated Mar. 19, 2012 in connection with U.S. Appl. No. 12/460,404.
Notice of Allowance dated Apr. 6, 2011 in connection with U.S. Appl. No. 12/069,147.
Notice of Allowance dated May 23, 2013 in connection with U.S. Appl. No. 13/493,816.
Notification Concerning Availability of the Publication of the International Application in connection with PCT/US2008/011367, dated Apr. 9, 2009.
Notification Concerning Transmittal of International Preliminary Report on Patentability in connection with PCT/US2008/001549, dated Aug. 11, 2009.
Notification of Transmittal of International Preliminary Report on Patentability in connection with PCT/US2008/011367, dated Apr. 15, 2010.
Notification of Transmittal of the International Preliminary Report on Patentability, in connection with PCT/US2009/004108, dated Feb. 10, 2011.
Notification of Transmittal of the International Preliminary Report on Patentability, in connection with PCT/US2009/004430, dated Feb. 10, 2011.
Notification of Transmittal of the International Search Report and the Written Opinion of the International Search Authority, or the Declaration, in connection with PCT/US2009/004108, dated Sep. 15, 2009.
Notification of Transmittal of the International Search Report and the Written Opinion of the International Search Authority, or the Declaration, in connection with PCT/U S2009/004108, dated Sep. 15, 2009.
Notification of Transmittal of the International Search Report and the Written Opinion of the International Search Authority, or the Declaration, in connection with PCT/US2009/004378, dated Sep. 18, 2009.
Notification of Transmittal of the International Search Report and the Written Opinion of the International Search Authority, or the Declaration, in connection with PCT/US2009/004430, dated Jan. 12, 2010.
Notification of Transmittal of the International Search Report and Written Opinion of the International Searching Authority, or the Declaration in connection with PCT/US2008/011367, dated Dec. 12, 2008.
Nov. 9, 2012 Patent Examination Report issued in connection with Australian Patent Application No. 2008284364.
Oct. 4, 2011 Communication issued in connection with European Patent Application No. 08794986.3.
Office Action dated Aug. 17, 2010 in connection with U.S. Appl. No. 11/703,401.
Office Action dated Aug. 20, 2013 in connection with U.S. Appl. No. 13/378,623.

(56) References Cited

OTHER PUBLICATIONS

Office Action dated Dec. 20, 2013 by the Canadian Patent Office in connection with Canadian Patent Application No. 2,676,422.
Olivier et al., "Recent advances in p53 research: an interdisciplinary perspective," Cancer Gene Therapy, vol. 16, No Month Listed 2009 (pp. 1-12).
Olmos et al., "Targeting polo-like kinase: learning too little too late?," Journal of Clinical Oncology, vol. 26, No. 34, Dec. 2008 (pp. 5497-5499).
Paez et al., "PI3K/PTEN/Akt Pathway," Signal Transduction in Cancer, vol. 115, No Month Listed 2006 (pp. 145-167).
Park et al., "N-CoR pathway targeting induces glioblastoma derived cancer stem cell differentiation," Cell Cycle, vol. 6, No. 4, Feb. 2007 (pp. 467-470).
Patent Search Report dated Oct. 25, 2011 in connection with Eurasian Patent Application No. 201170288, filed Jul. 30, 2009.
Peng et al., "Induction of apoptosis by norcantharidin in human colorectal carcinoma cell lines: involvement of the CD95 receptor/ligand," Journal of Cancer Research and Clinical Oncology, vol. 128, No. 4, Apr. 2002 (pp. 223-230).
Perrotti et al., "Protein phosphatases 2A (PP2A), a drugable tumor suppressor in Ph1(+) leukemias," Cancer and Metastasis Reviews, vol. 27, No. 2, Jun. 2008 (pp. 159-168).
Prados et al., "Phase II Study of Erlotinib Plus Temozolomide During and After Radiation Therapy in Patients with Newly Diagnosed Glioblastoma Multiforme or Gliosarcoma," Journal of Clinical Oncology, vol. 27, No. 4, Feb. 2009 (pp. 579-584).
Price et al., "Histone deacetylase inhibitors: an analysis of recent patenting activity," Expert Opinion on Therapeutic Patents, vol. 17, No. 7, Aug. 2007 (pp. 745-765).
Ramezanian et al., "A new super-electrophile: alpha(phenylsulfonyl)maleic anhydride," Journal of Organic Chemistry, vol. 54, No. 12, Jun. 1989 (pp. 2852-2854).
Registry (STN) Online, Nov. 16, 1984, CAS registered No. 57958-23-3 (Search Date Jan. 16, 2013).
Restriction Requirement dated May 18, 2011 in connection with U.S. Appl. No. 12/460,404.
Restriction Requirement dated Sep. 28, 2012 in connection with U.S. Appl. No. 13/493,816.
Richon et al., "A class of hybrid polar inducers of transformed cell differentiation inhibits histone deacetylases," Proceedings of the National Academy of Sciences U.S.A., vol. 95, No. 6, Mar. 1998 (pp. 3003-3007).
Riester et al., "Histone deacetylase inhibitors—turning epigenic mechanisms of gene regulation into tools of therapeutic intervention in malignant and other diseases," Applied Microbiology and Biotechnology, vol. 75, Jun. 2007 (pp. 499-514).
Rinkenberger et al., "Mc1-1 deficiency results in peri-implantation embryonic lethality," Genes and Development, vol. 14, No. 1, Jan. 2000 (pp. 23-27).
Rubie et al., "Phase II Study of Temozolomide in Relapsed or Refractory high-Risk Neuroblastoma: A Jount Societe Francaise des Cancers del'Enfant and United Kingdom Children Cancer Study Group-New Agents Group Study," Journal of Clinical Oncology, vol. 24, No. 33, Nov. 2006 (pp. 5259-5264).
Rutka et al., "Effect of retinoids on the proliferation, morphology and expression of glial fibrillary acidic protein of an anaplastic astrocytoma cell line," International Journal of Cancer, vol. 42, No. 3, Sep. 1988 (pp. 419-427).
Sahin et al., "Retinoic acid isomers protect hippocampal neurons from amyloid-beta induced neurodegeneration," Neurotoxicity Research, vol. 7, No. 3, No Month Listed 2005 (pp. 243-250).
Saito et al., "A synthetic inhibitor of deacetylase, MS-27-275, with marked in vivo antitumor activity against human tumors," Proceedings of the National Academy of Sciences U.S.A., vol. 96, No. 8, Apr. 1999 (pp. 4592-4597).
Sakoff et al., "Anticancer Activity and Protein Phosphatase 1 and 2A Inhibition of a New Generation of Cantharidin Analogues," Investigational New Drugs, vol. 20, No. 1, Feb. 2002 (pp. 1-11).

Sakoff et al., "Protein Phosphatase Inhibition: Structure Based Design. Towards New Therapeutic Agents," Current Pharmaceutical Design, vol. 10, No. 10, No Month Listed 2004 (pp. 1139-1159).
Sanderson et al., "Plasma pharmacokinetics and metabolism of the histone deacetylase inhibitor trichostatin a after intraperitoneal administration to mice," Drug Metabolism and Disposition, vol. 32, No. 10, Jul. 2004, (pp. 1132-1138).
Science IP Search Report dated Sep. 20, 2007.
Shimi et al., "A new antitumour substance, 7-oxabicyclo (2.2.1)-5-heptene-2,3-dicarboxylic anhydride," European Journal of Cancer, vol. 18, No. 8, Aug. 1982 (pp. 785-793).
Shore et al., "Unique Biology of Mc1-1: Therapeutic Opportunities in Cancer," Current Molecular Medicine, vol. 8, No. 2, Mar. 2008 (pp. 138-147).
Short et al., "DNA repair after irradiation in glioma cells and normal human astrocytes," Neuro-Oncology, vol. 9, No. 4, Oct. 2007 (pp. 404-411).
Singh et al., "Identification of a cancer stem cell in human brain tumors," Cancer Research, vol. 63, No. 18, Sep. 2003 (pp. 5821-5828).
Singh et al., "Identification of human brain tumour initiating cells," Nature, vol. 432, Nov. 2004 (pp. 396-401).
Smith et al., "Histone deacetylase inhibitors enhance Candida albicans sensitivity to azoles and related antifungals: correlation with reduction in CDR and ERG upregulation," Antimicrobial Agents and Chemotherapy, vol. 46, No. 11, Nov. 2002 (pp. 3532-3539).
Song et al., Synthesis and Biological Properties of Amino Acid Amide Ligand-Based Pyridinioalkanoyl Thioesters as Anti-HIV Agents, Bioorganic and Medicinal Chemistry, vol. 10, No. 5, May 2002 (pp. 1263-1273).
Sridharan et al., "Illuminating the black box of reprogramming," Cell Stem Cell, vol. 2, No. 4, Apr. 2008 (pp. 295-297).
Stewart et al., "Synthesis and biological evaluation of norcantharidin analogues: towards PP1 selectivity," Bioorganic and Medicinal Chemistry, vol. 15, No. 23, Dec. 2007 (pp. 7301-7310).
Strebhardt et al., "Targeting polo-like kinase 1 for cancer therapy," Nature Reviews: Cancer, vol. 6, Apr. 2006 (11 pages).
Stupp et al., Radiotherapy plus Concomitant and Adjuvant Temozolomide for Glioblastoma, The New England Journal of Medicine, vol. 352, Mar. 2005 (pp. 987-996).
Supplemental European Search Report and European Search Opinion dated Apr. 2, 2012 in connection with European Patent Application No. 09803283.2, filed Jan. 24, 2011.
Supplemental European Search Report in connection with EP 08794986.3, dated Dec. 15, 2010.
Susini et al., "TCTP protects from apoptotic cell death by antagonizing bax function," Cell Death and Differentiation, vol. 15, Feb. 2008 (pp. 1211-1220).
Suzuki et al., "Synthesis and histone deacetylase inhibitory activity of new benzamide derivatives," Journal of Medicinal Chemistry, vol. 42, No. 15, Jul. 1999 (pp. 3001-3003).
Sweatt, "Behavioural Neuroscience: Down Memory Lane," Nature, vol. 447, May 2007 (pp. 151-152).
Tocris Biosciences: retinoic acid receptors product data sheet (2010).
Toma et al., "Retinoids and human breast cancer: in vivo effects of an antagonist for RAR-alpha," Cancer Letters, vol. 219, No. 1, Feb. 2005 (pp. 27-31).
Touma et al., "Retinoic acid and the histone deacetylase inhibitor trichostatin a inhibit the proliferation of human renal cell carcinoma in a xenograft tumor model," Clinical Cancer Research, vol. 11, No. 9, May 2005 (pp. 3558-3566).
Trost et al., "New synthetic reagents, Methylthiomaleic anhydride: a synthon for protected carbomethoxyketene," Journal of the American Chemical Society, vol. 99, No. 21, Oct. 1977 (pp. 7079-7082).
Tuynder et al., "Biological models and genes of tumor reversion: cellular reprogramming through tptl/TCTP and SIAH-1," Proceedings of the National Academy of Sciences U.S.A., vol. 99, No. 23, Nov. 2002 (pp. 14976-14981).
Tuynder et al., "Translationally controlled tumor protein is a target of tumor reversion," Proceedings of the National Academy of Sciences U.S.A., vol. 101, No. 43, Oct. 2004 (pp. 15364-154369).

(56) References Cited

OTHER PUBLICATIONS

Uchida et al., "Direct isolation of human central nervous system stem cells," Proceedings of the National Academy of Sciences U.S.A., vol. 97, No. 26, Dec. 2000 (pp. 14720-14725).
Valeriote et al., "Synergistic interaction of anticancer agents: a cellular perspective," Cancer Chemotherapy Reports, vol. 59, No. 5, Sep.-Oct. 1975 (pp. 895-900).
Vazquez et al., "The genetics of the p53 pathway, apoptosis and cancer therapy," Nature Reviews: Drug Discovery, vol. 7, No. 12, Dec. 2008 (pp. 979-987).
Wang, "Effect of norcantharidin on the number of white blood cells," Chinese Pharm. Bull., vol. 22, No Month Listed 1987 (pp. 517-519) with English translation of abstract prepared at the applicants 'attorney' office.
Wang, "Hydrolysis and demethylation of cantharidin on the relief of its urinary irritation," Chin. Pharmac. Bull., vol. 18, No Month Listed 1983 (pp. 18-19) with English language title available from the journal and English language summary prepared at the applicants' attorneys' office.
Wang, "Medical uses of mylabris in ancient China and recent studies," Journal of Ethnopharmcology, vol. 26, No. 2, Sep. 1983 (pp. 147-162).
Wang, "Results of clinical trials in 244 cases of primary hepatoma and with norcantharidin," Chinese Pharm. Bull., vol. 21, No Month Listed 1986 (pp. 90-93) with English translation of abstract prepared at the applicants' attorneys' office.
Warrell et al., "Therapeutic Targeting of Transcription in Acute Promyelocytic Leukemia by Use of an Inhibitor of Histone Deacetylase," Journal of the National Cancer Institute, vol. 90, No. 21, Nov. 1998 (pp. 1621-1625).
Waters et al., "Analysis of co-factor function in a glucocorticoid-resistant small cell carcinoma cell line," Journal of Endocrinology, vol. 183, No. 2, Nov. 2004 (pp. 375-383).

Weinmann et al., "Histone deacetylase inhibitors: a survey of recent patents," Expert Opinion on Therapeutic Patents, vol. 15, No. 12, Nov. 2005 (pp. 1677-1690).
Westermarck et al., "Multiple pathways regulated by the tumor suppressor PP2A in transformation," Trends in Molecular Medicine, vol. 14, No. 4, Apr. 2008 (pp. 152-160).
Written Opinion in connection with PCT/US2008/011367, dated Dec. 12, 2008.
Written Opinion in connection with PCT/US2009/004108, dated Sep. 15, 2009.
Written Opinion in connection with PCT/US2009/004378, dated Sep. 18, 2009.
Written Opinion in connection with PCT/US2009/004430, dated Jan. 12, 2010.
Yan et al., "Inhibition of protein phosphatase activity induces p53-dependent apoptosis in the absence of p53 transactivation," Journal of Biological Chemistry, vol. 272, No. 24, Jun. 1997 (pp. 15220-15226).
Yang et al., "An N-terminal region of translationally controlled tumor protein is required for its antiapoptotic activity," Oncogene, vol. 24, No. 30, Jul. 2005 (pp. 4778-4788).
Yarm, "Plk phosphorylation regulates the microtubule-stabilizing protein TCTP," Molecular and Cellular Biology, vol. 22, No. 17, Sep. 2002 (pp. 6209-6221).
Yoshida et al., "Potent and specific inhibition of mammalian histone deacetylase both in vivo and in vitro by trichostatin A," Journal of Biological Chemistry, vol. 265, No. 28, Oct. 1990 (pp. 17174-17179).
Yoshida et al., "Trichostatin and leptomycin. Inhibition of histone deacetylation and signal-dependent nuclear export," Annals of the New York Academy of Sciences, vol. 886, No Month Listed 1999 (pp. 23-26).
Yung et al., "Treatment of recurrent malignant gliomas with high-dose 13-cis-retinoic acid," Clinical Cancer Research, vol. 2, No. 12, Dec. 1996 (pp. 1931-1935).
Yur'ev et al., Chemical Abstracts, vol. 56, No. 73368, No Month Listed 1961.

Fig. 19A
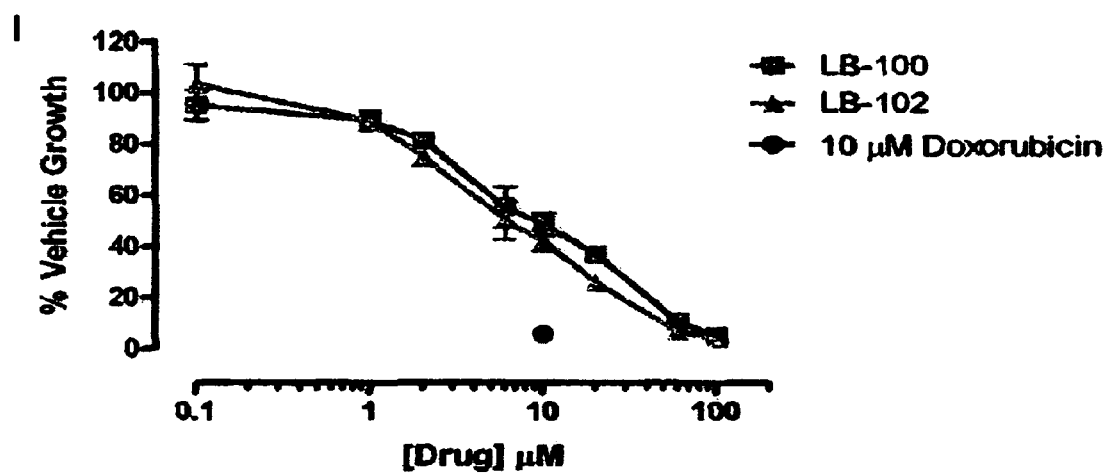
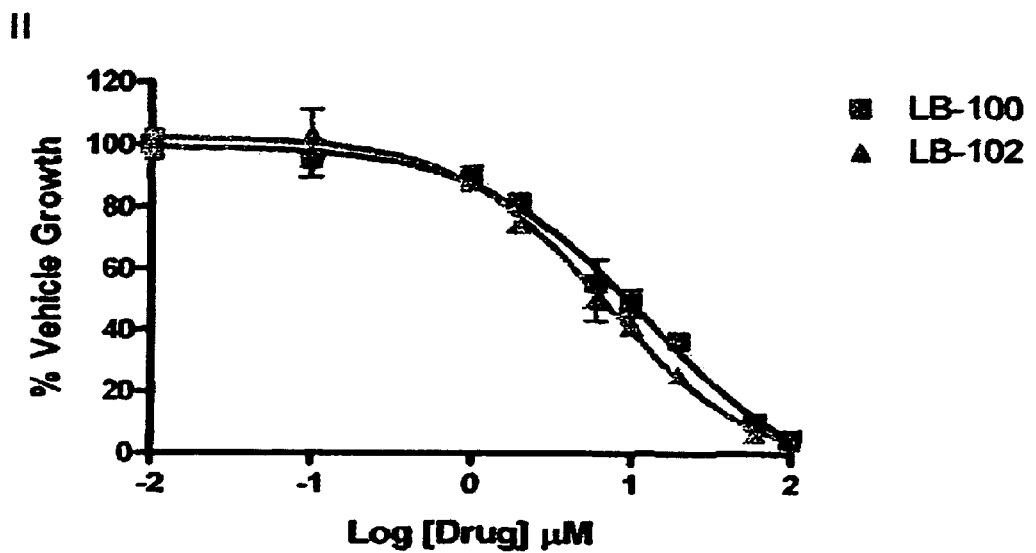

Fig. 19C
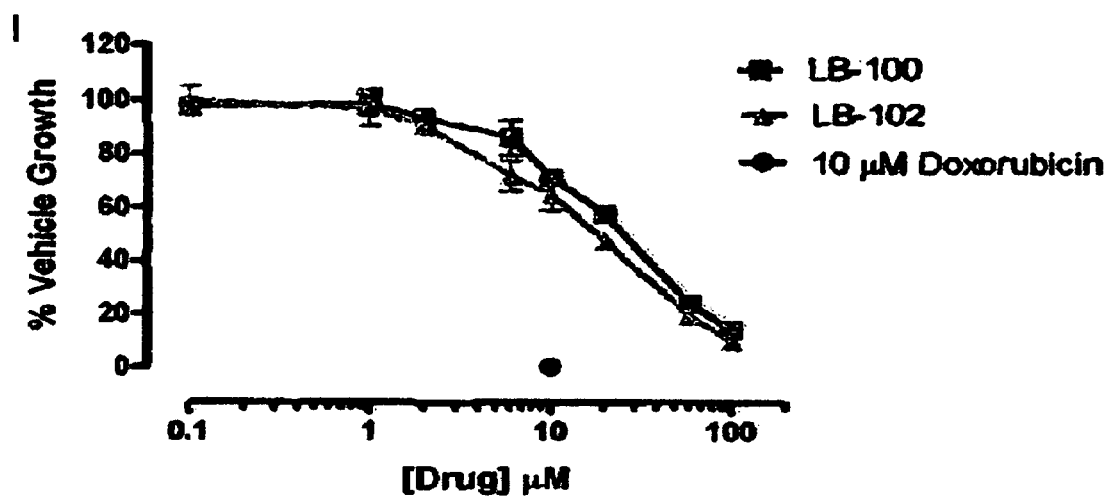
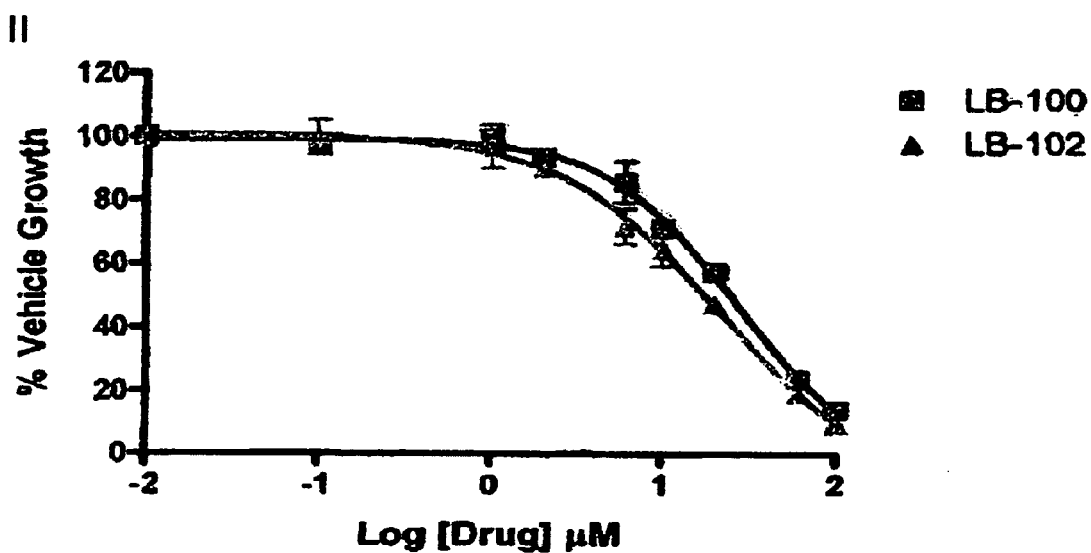

Fig. 19D
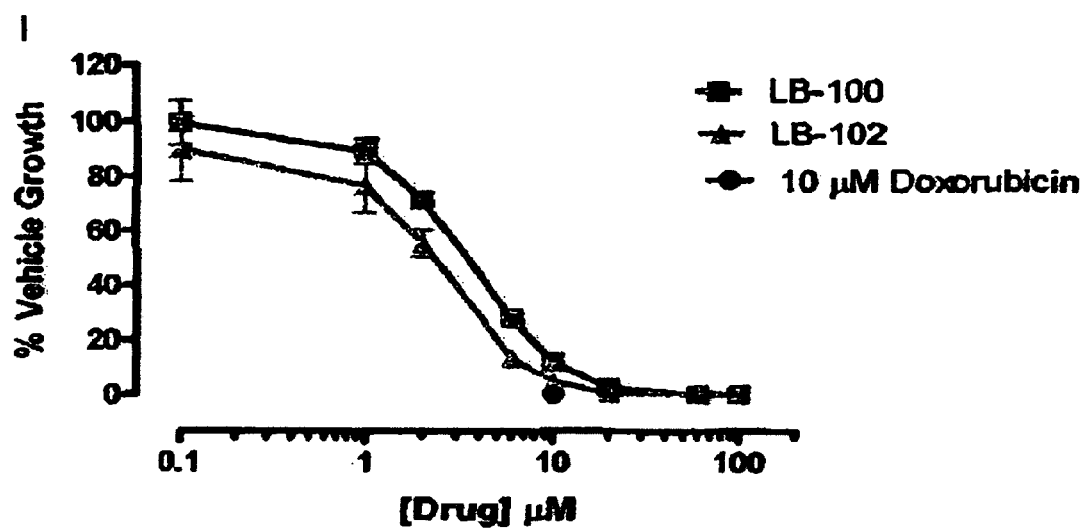
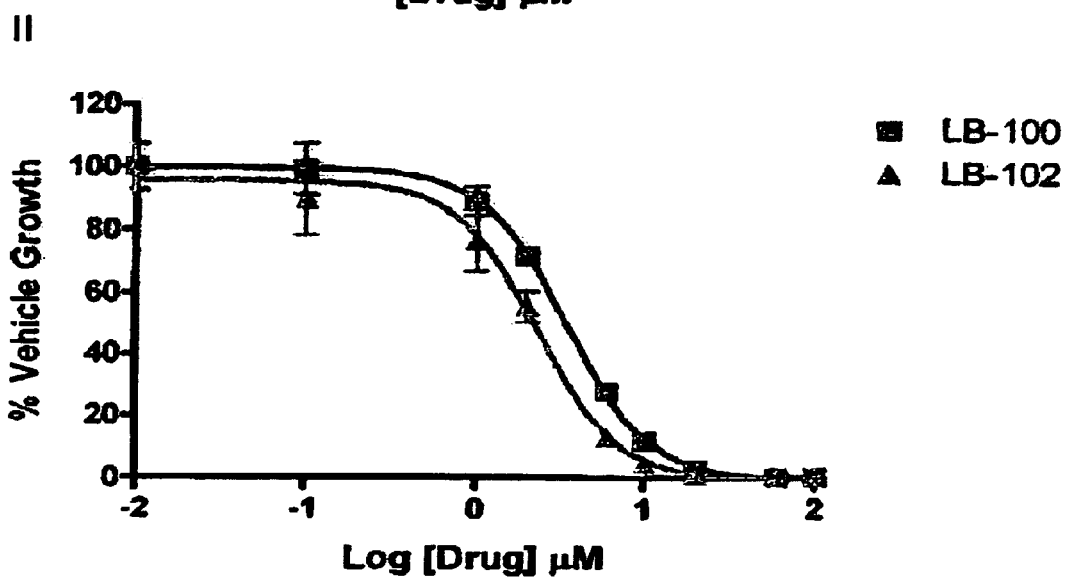

Fig. 19E
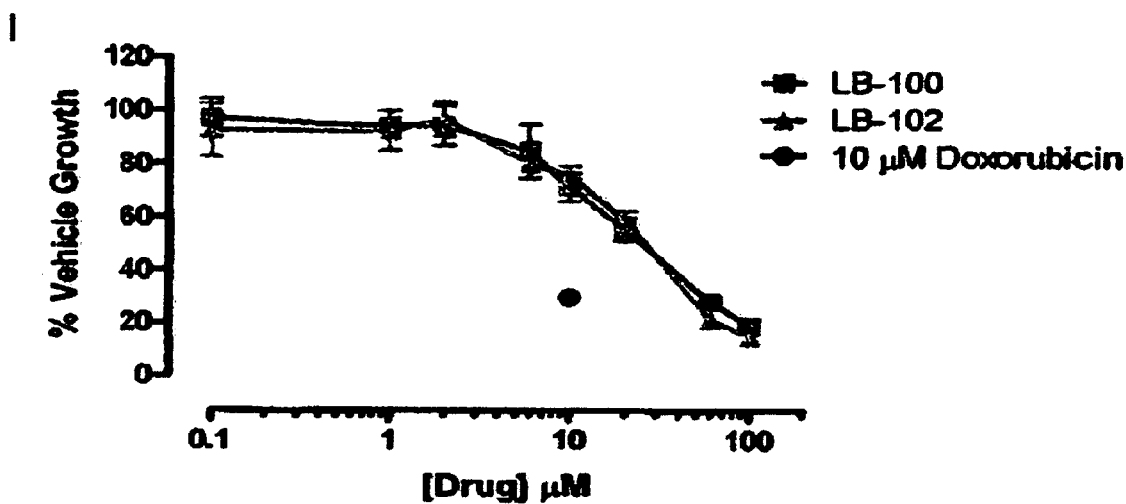
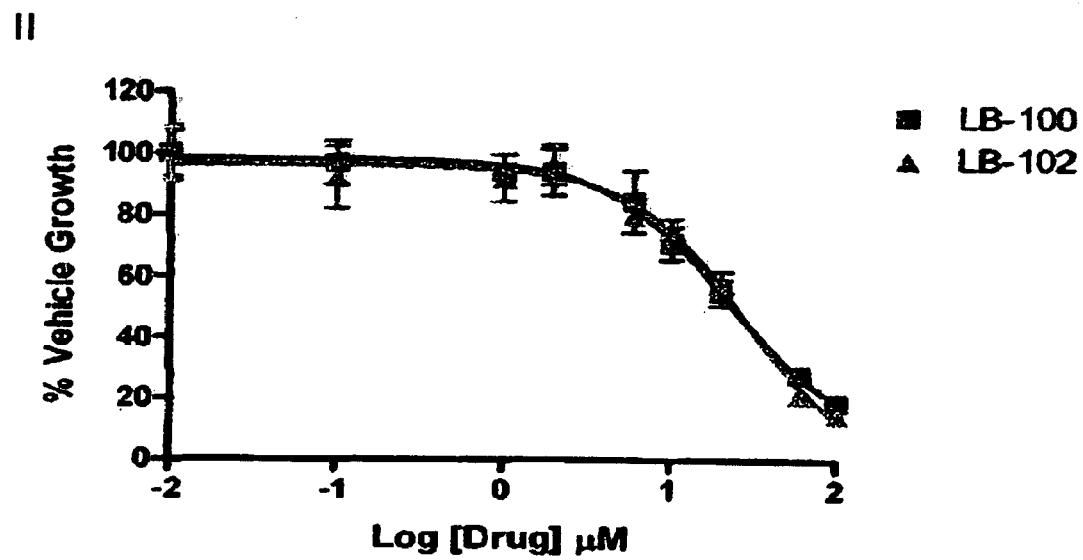

Fig. 19F
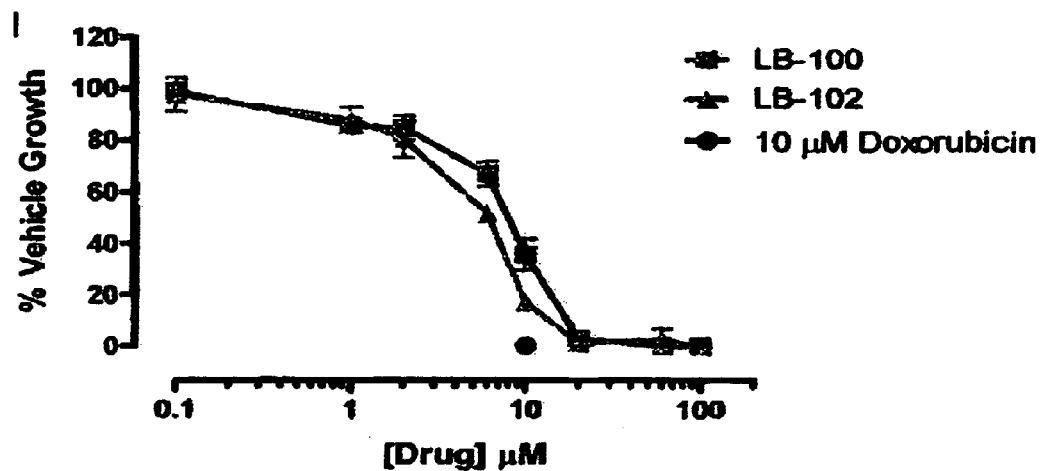
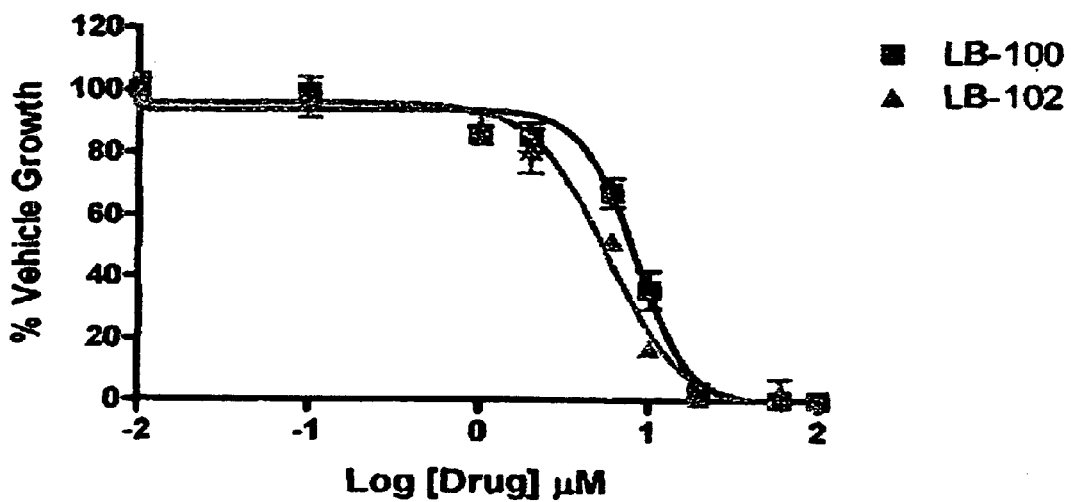

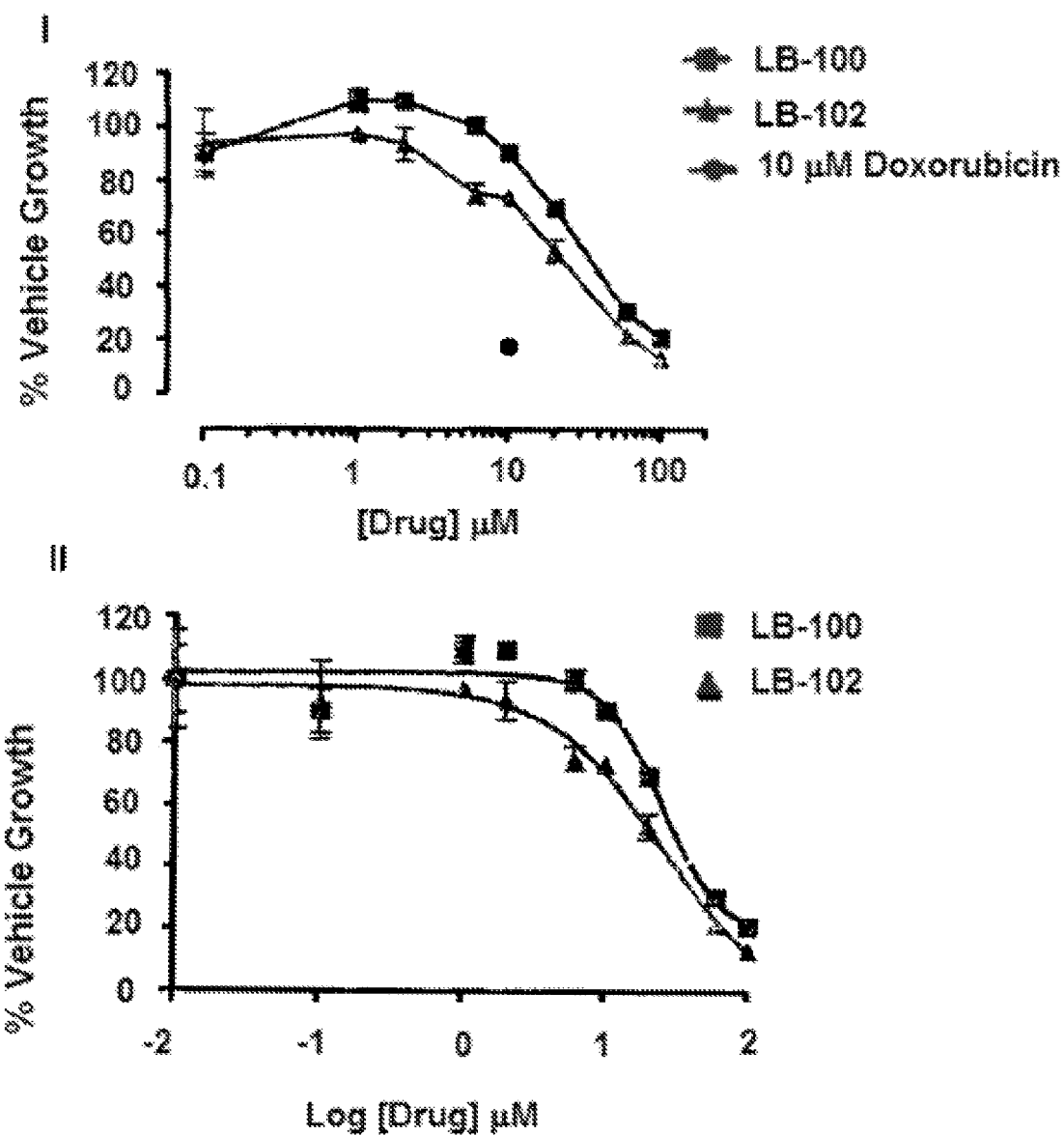

Fig. 19H
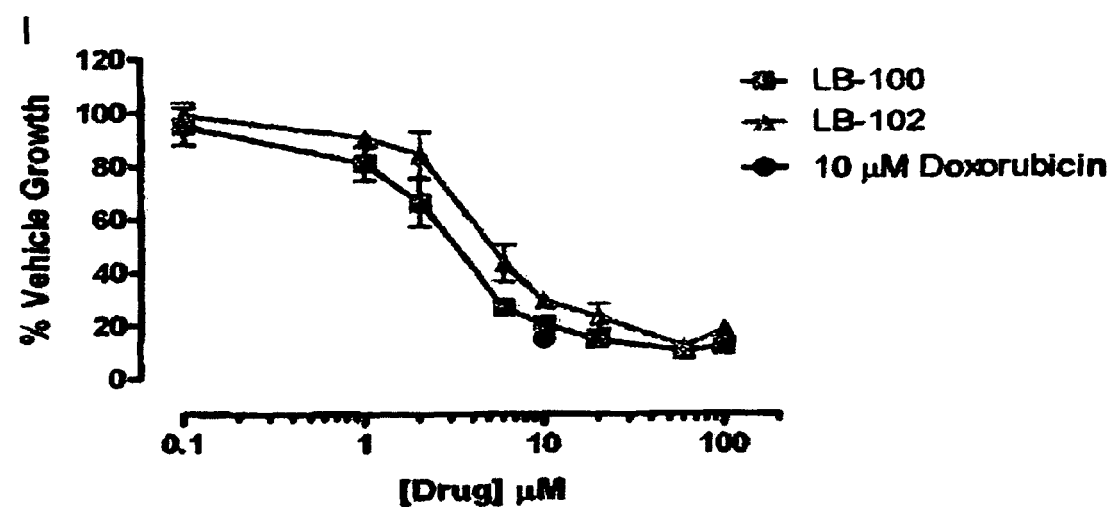
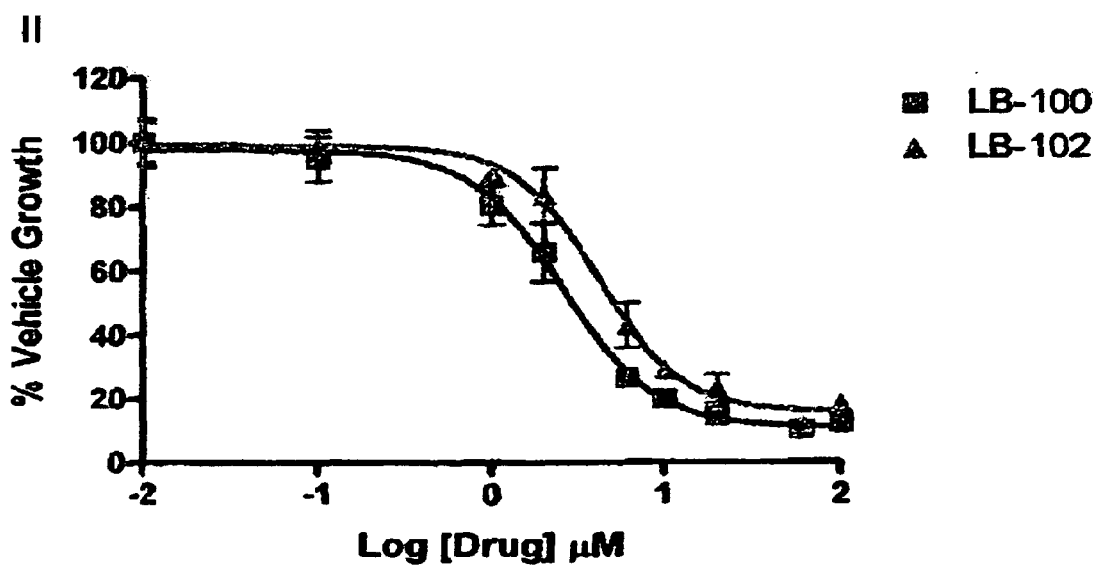

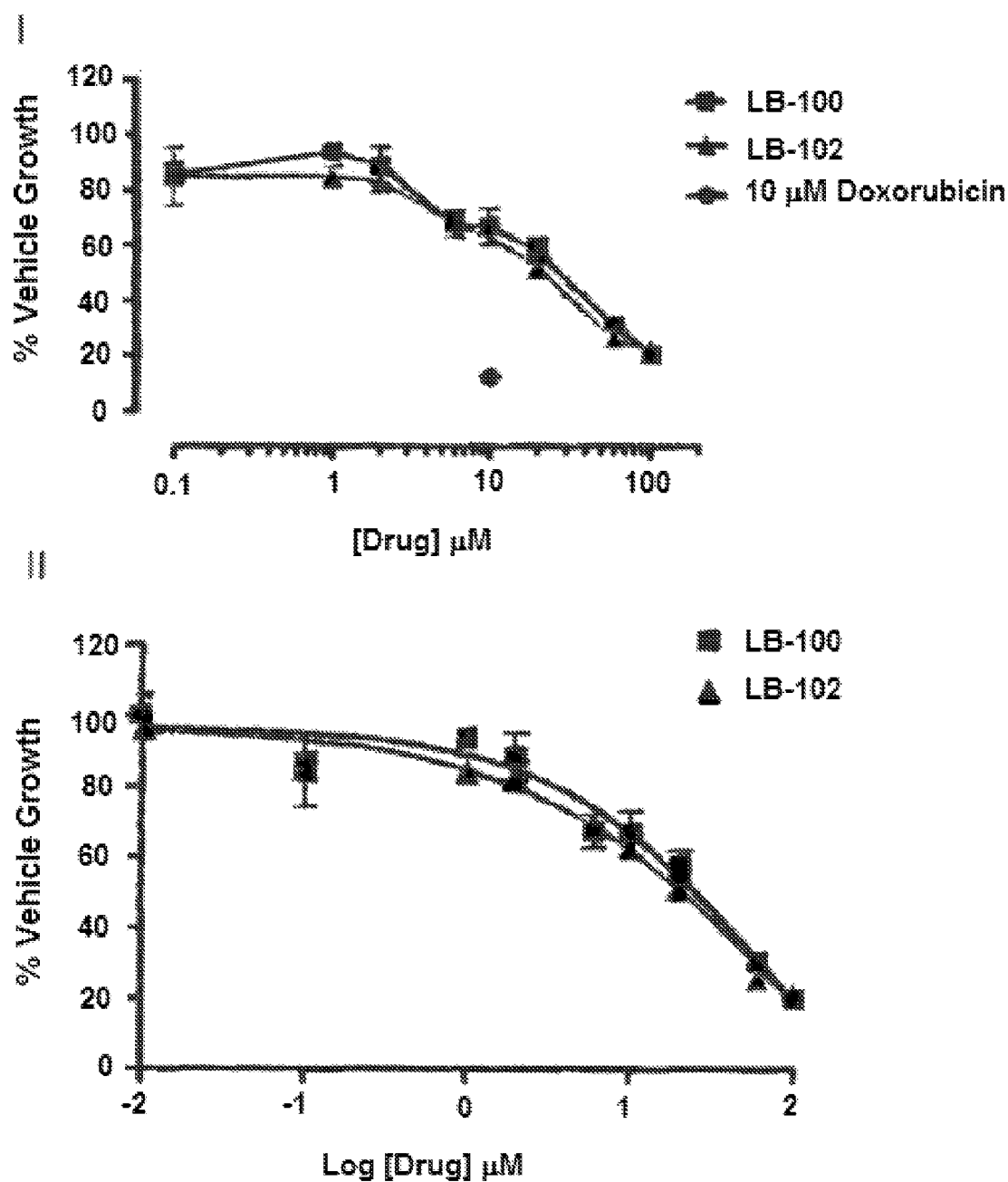

Fig. 19K
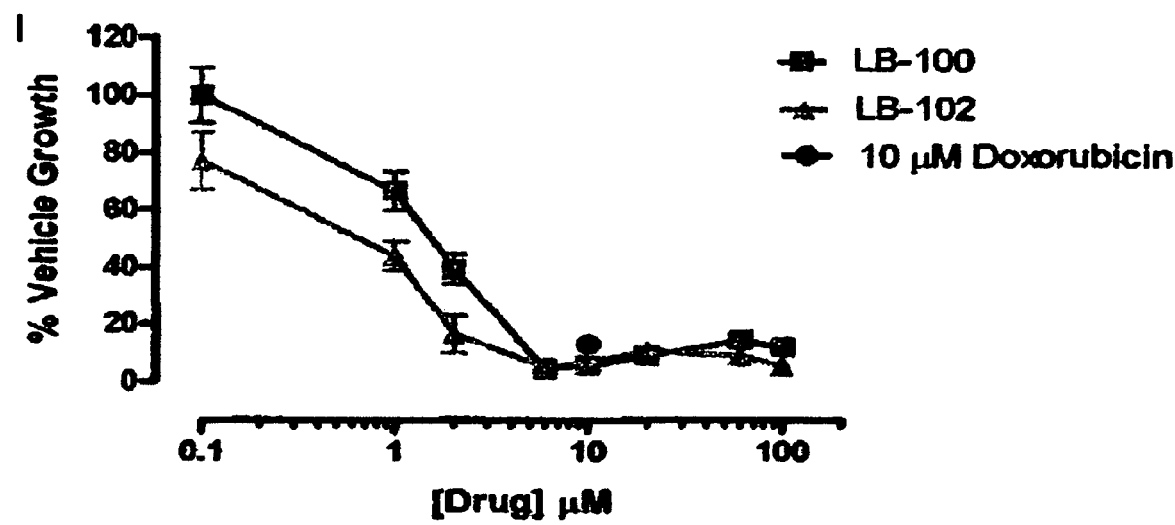
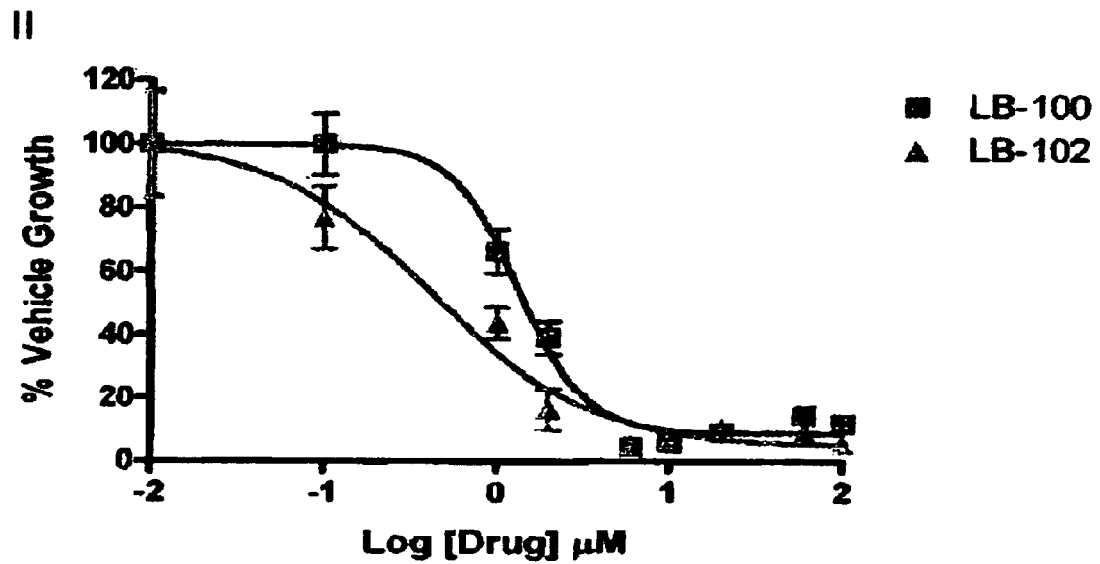

OXABICYCLOHEPTANES AND OXABICYCLOHEPTENES, THEIR PREPARATION AND USE

The present application is a continuation of U.S. Ser. No. 15/275,954, filed Sep. 26, 2016, which is a continuation of U.S. Ser. No. 15/150,129, filed May 9, 2016, which is a continuation of U.S. Ser. No. 15/004,525, filed Jan. 22, 2016, which is a continuation of U.S. Ser. No. 14/794,110, filed Jul, 8, 2015, which is a continuation of U.S. Ser. No. 14/328,384, filed Jul. 10, 2014, now U.S. Pat. No. 9,079,917, which is a divisional of U.S. Ser. No. 13/866,854, filed Apr, 19, 2013, now U.S. Pat. No. 8,822,461, which is a continuation of U.S. Ser. No. 13/174,249, filed Jun. 30, 2011, now U.S. Pat. No. 8,426,444, which is a divisional of U.S. Ser. No. 12/069,147, filed Feb. 6, 2008, now U.S. Pat. No. 7,998,957, which claims the benefit of U.S. Provisional Application 61/011,323, filed Jan. 15, 2008, U.S. Provisional Application No. 60/964,904, filed Aug. 14, 2007 and U.S. Provisional Application No. 60/899,903, filed Feb. 6, 2007, the contents of each of which are hereby incorporated by reference.

Throughout this application, certain publications are referenced. Full citations for these publications may be found immediately preceding the claims. The disclosures of these publications in their entireties are hereby incorporated by reference into this application in order to describe more fully the state-of-the art to which this invention relates.

BACKGROUND OF THE INVENTION

Retinoids, metabolites of vitamin A, have been examined therapeutically against a variety of tumors, including gliomas. (Yung et al. (1996)) Nuclear receptor co-repressor (N-CoR) is closely associated with the retinoid receptor and is released upon ligand binding to the receptor. (Bastien et al. (2004)) By preventing the action of protein phosphatase-1 and protein phosphatase-2A, anti-phosphatases increase the phosphorylated form of N-CoR and promotes its subsequent cytoplasmic translocation. (Hermanson et al. (2002))

The phosphatase inhibitor, Cantharidin, has anti-tumor activity against human cancers of the liver (hepatomas) and of the upper gastrointestinal tract but is toxic to the urinary tract (Wang, 1989).

The publication of a report that cantharidin acts as a protein phosphatase inhibitor prompted a more general interest in compounds with this type of chemical structure (Li and Casida, 1992). Previously, it had been found that the simpler congener and its hydrolysis product (commercially available as the herbicide, Endothall) are hepatotoxic (Graziani and Casida, 1997). Binding studies have shown that the action of certain cantharidin homologs is direct on protein phosphatase-2A and indirect on protein phosphatase-1 (Honkanen et al., 1993; Li et al., 1993).

Of the known congeners of this type of compound, only the parent, cantharidin and its bis(normethyl)-derivative, norcantharidin, have seen any use as anti-cancer drug substances and only norcantharidin is used as an anti-neoplastic agent (Tsauer et al., 1997).

Despite these successes, few compounds of this type have been screened for anti-tumor or cytotoxic activity. Currently, there is a significant need to develop inhibitors of protein phosphatases that are more active, less toxic and more specific in action than the known substances mentioned above.

SUMMARY OF THE INVENTION

A compound having the structure

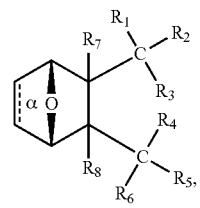

wherein bond α is present or absent;

$R_1$ and $R_2$ is each independently H, O$^-$, or OR$_9$,
  where $R_9$ is H, alkyl, alkenyl, alkynyl or aryl,
  or $R_1$ and $R_2$ together are =O;

$R_3$ and $R_4$ are each different and each is OH, O$^-$, OR$_9$, SH, S$^-$, SR$_9$

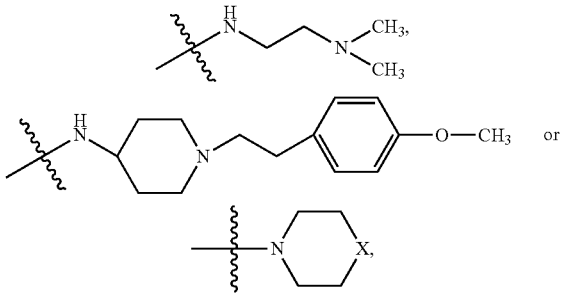

where X is O, S, NR$_{10}$, or N*R$_{10}$R$_{10}$,
  where each $R_{10}$ is independently alkyl, substituted $C_2$-$C_{12}$ alkyl, alkenyl, substituted $C_4$-$C_{12}$ alkenyl, alkynyl, substituted alkynl, aryl, substituted aryl where the substituent is other than chloro when $R_1$ and $R_2$ are =O,

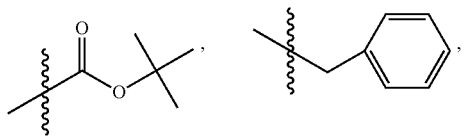

—CH$_2$CN, —CH$_2$CO$_2$R$_{11}$, —CH$_2$COR$_{11}$, —NHR$_{11}$ or —NH$^+$(R$_{11}$)$_2$, wherein $R_{11}$ is alkyl, alkenyl or alkynyl, each of which is substituted or unsubstituted, or H;

$R_5$ and $R_6$ is each independently H, OH, or $R_5$ and $R_6$ taken together are =O; and $R_7$ and $R_8$ is each independently H, F, Cl, Br, SO$_2$Ph, CO$_2$CH$_3$, or SR$_{12}$,
  where $R_{12}$ is H, aryl or a substituted or unsubstituted alkyl, alkenyl or alkynyl, or a salt, enantiomer or zwitterion of the compound.

A compound having the structure

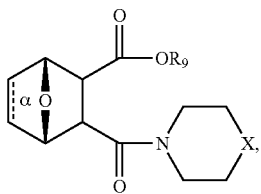

wherein
bond α is present or absent;
R$_9$ is present or absent and when present is H, alkyl, alkenyl, alkynyl or phenyl; and
X is O, NR$_{10}$, or NH$^+$R$_{10}$,
where each R$_{10}$ is independently H, alkyl, substituted C$_2$-C$_{12}$ alkyl, alkenyl, substituted C$_4$-C$_{12}$ alkenyl, alkynyl, substituted alkynl, aryl, substituted aryl where the substitutent is other than chloro,

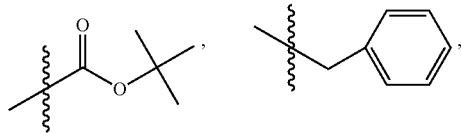

—CH$_2$CN, —CH$_2$CO$_2$R$_{12}$, or —CH$_2$COR$_{12}$, where R$_{12}$ is H or alkyl,
or a salt, zwitterions, or enantiomer of the compound.
A compound having the structure

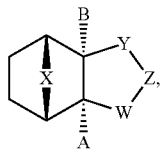

wherein
A and B is each independently H, F, Cl, Br, SO$_2$Ph, CO$_2$CH$_3$, CN, COR$_{14}$ or SR$_{14}$,
where R$_{14}$ is H or aryl or a substituted or unsubstituted alkyl, alkenyl or alkynyl;
X is O, NH or S;
Z is O, S, SR$_{15}$, NH, NR$_{15}$, CH$_2$OH, CH$_2$OR$_{15}$,
where R$_{15}$ is an aryl or a substituted or unsubstituted alkyl, alkenyl or alkynyl; and
Y and W is each independently CH$_2$, CHOH, C=O, or C=S,
or a salt of the compound.

The invention further contemplates a method of controlling undesired vegetation comprising contacting the vegetation or its environment with a herbicidally effective amount of the compounds of the invention.

The invention further contemplates a method of inhibiting plant phosphatase activity comprising contacting the plant or its environment with a herbicidally effective amount of the compounds of the invention.

This invention further contemplates a method of preventing or treating fungal infections in a subject comprising administering to the subject an effective amount of the compounds of this invention.

This invention further contemplates a method of treating cancer in a subject comprising administering to the subject an effective amount of the compounds of the invention.

BRIEF DESCRIPTION OF THE FIGURES

FIG. 19A: Graphical representation (I) and curve fit with $IC_{50}$ value (II) of data obtained following exposure of MDA-MB-231 cells to compound 100 and compound 102 using the CellTiter-Glo assay. The effects of 10 μM doxorubicin that was used as a positive control are also shown in I. Each point represents the mean±SD of at least triplicate samples.

FIG. 19C: Graphical representation (I) and curve fit with $IC_{50}$ value (II) of data obtained following exposure of NCI-H460 cells to compound 100 and compound 102 using the CellTiter-Glo assay. The effects of 10 μM doxorubicin that was used as a positive control are also shown in I. Each point represents the mean±SD of at least triplicate samples.

FIG. 19D Graphical representation (I) and curve fit with $IC_{50}$ value (II) of data obtained following exposure of NCI-H522 cells to compound 100 and compound 102 using the CellTiter-Glo assay. The effects of 10 μM doxorubicin that was used as a positive control are also shown in I. Each point represents the mean±SD of at least triplicate samples.

FIG. 19E Graphical representation (I) and curve fit with $IC_{50}$ value (II) of data obtained following exposure of NCI-H69 cells to compound 100 and compound 102 using the CellTiter-Glo assay. The effects of 10 μM doxorubicin that was used as a positive control are also shown in I. Each point represents the mean±SD of at least triplicate samples.

FIG. 19F: Graphical representation (I) and curve fit with $IC_{50}$ value (II) of data obtained following exposure of GXF-209 cells to compound 100 and compound 102 using the CellTiter-Glo assay. The effects of 10 μM doxorubicin that was used as a positive control are also shown in I. Each point represents the mean±SD of at least triplicate samples.

FIG. 19G: Graphical representation (I) and curve fit with $IC_{50}$ value (II) of data obtained following exposure of HepG2 cells to compound 100 and compound 102 using the CellTiter-Glo assay. The effects of 10 μM doxorubicin that was used as a positive control are also shown in I. Each point represents the mean±SD of at least triplicate samples.

FIG. 19H: Graphical representation (I) and curve fit with $IC_{50}$ value (II) of data obtained following exposure of OVCAR-3 cells to compound 100 and compound 102 using the CellTiter-Glo assay. The effects of 10 μM doxorubicin that was used as a positive control are also shown in I. Each point represents the mean±SD of at least triplicate samples.

FIG. 19I: Graphical representation (I) and curve fit with $IC_{50}$ value (II) of data obtained following exposure of PANC-1 cells to compound 100 and compound 102 using the CellTiter-Glo assay. The effects of 10 μM doxorubicin that was used as a positive control are also shown in I. Each point represents the mean±SD of at least triplicate samples.

FIG. 19K: Graphical representation (I) and curve fit with $IC_{50}$ value (II) of data obtained following exposure of LNCAP cells to compound 100 and compound 102 using the CellTiter-Glo assay. The effects of 10 μM doxorubicin that was used as a positive control are also shown in I. Each point represents the mean±SD of at least triplicate samples.

DETAILED DESCRIPTION OF THE INVENTION

A compound having the structure

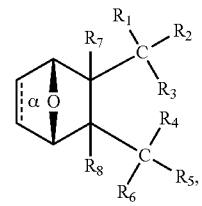

Figure 1:
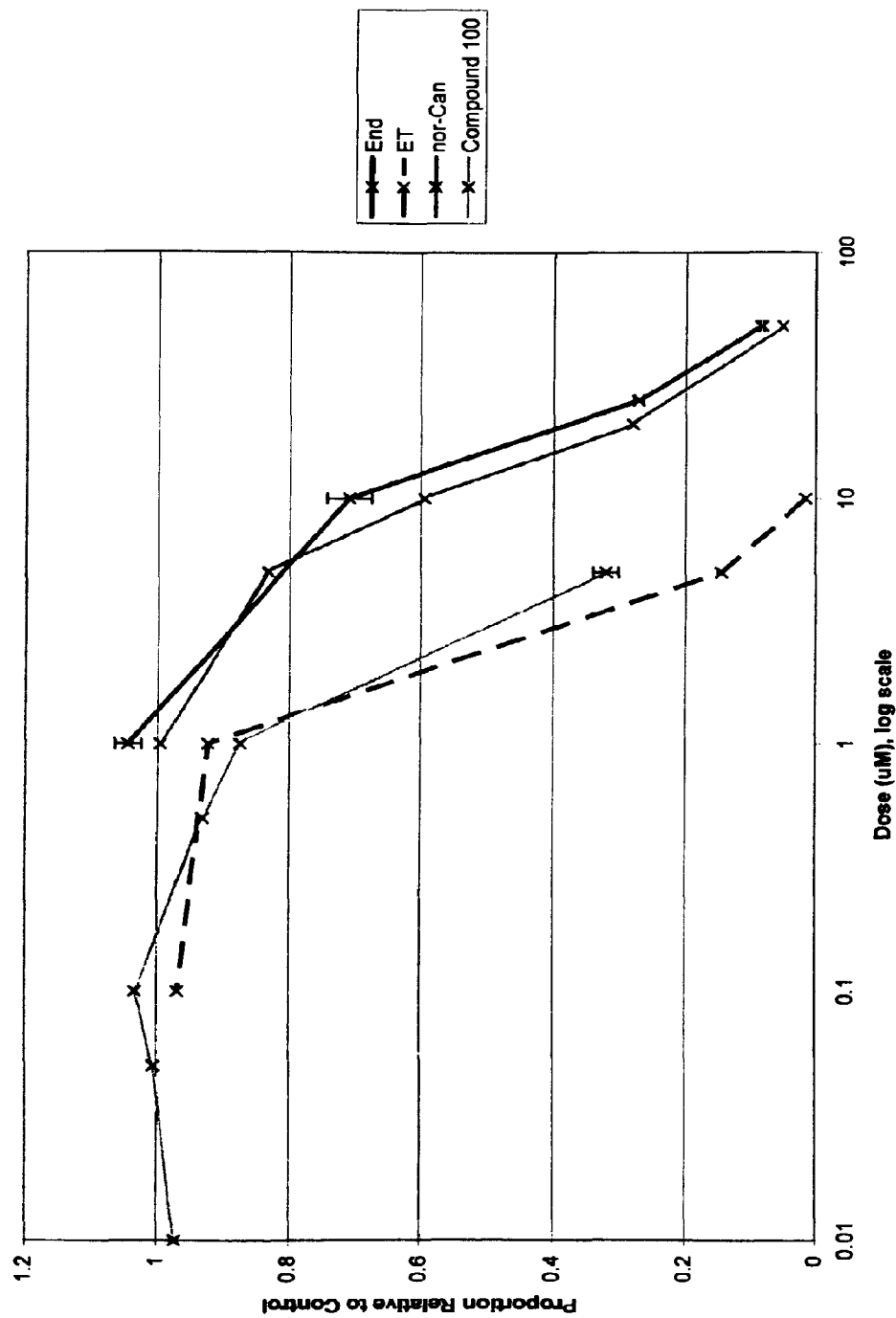
FIG. 1: Logarithmic curve of gliomal cell line U373 treated with endothal (End), endothal thioanhydride (ET), nor-cantharidin (nor-Can) or Compound 100. Increasing dosages demonstrate a greater inhibition of growth. Error bars indicate SD.

wherein bond α is present or absent; $R_1$ and $R_2$ is each independently H, O⁻, $OR_9$, where $R_9$ is H, alkyl, alkenyl, alkynyl or aryl, or $R_1$ and $R_2$ together are =O; $R_3$ and $R_4$ are each different and each is OH, O⁻, $OR_9$, SH, S⁻, $SR_9$

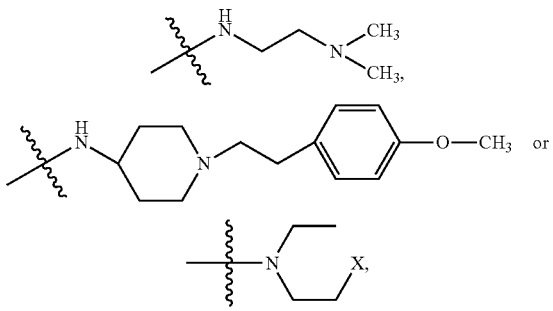

where X is O, S, $NR_{10}$, $N^+R_{10}R_{10}$, where each $R_{10}$ is independently alkyl, substituted $C_2$-$C_{12}$ alkyl, alkenyl, substituted $C_4$-$C_{12}$ alkenyl, alkynyl, substituted alkynl, aryl, substituted aryl where the substituent is other than chloro when $R_1$ and $R_2$ are =O,

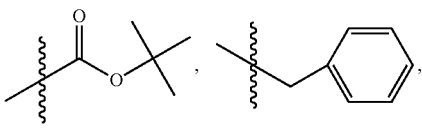

—CH$_2$CN, —CH$_2$CO$_2$R$_{11}$, —CH$_2$COR$_{11}$, —NHR$_{11}$, —NH$^+$(R$_{11}$)$_2$ wherein each R$_{11}$ is independently alkyl, alkenyl or alkynyl, each of which is substituted or unsubstituted, or H;

R$_5$ and R$_6$ is each independently H, OH, or R$_5$ and R$_6$ taken together are =O; and R$_7$ and R$_8$ is each independently H, F, Cl, Br, SO$_2$Ph, CO$_2$CH$_3$, CN, COR$_{12}$, or SR$_{12}$, where R$_{12}$ is H, aryl or a substituted or unsubstituted alkyl, alkenyl or alkynyl, or a salt, enantiomer or zwitterion of the compound.

An embodiment of the invention provides a compound of the structure

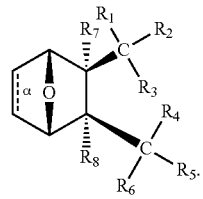

The invention further provides the instant composition, wherein R$_1$ and R$_2$ together are =O; R$_3$ is O$^-$ or OR$_9$, where R$_9$ is H, methyl, ethyl or phenyl; R$_4$ is

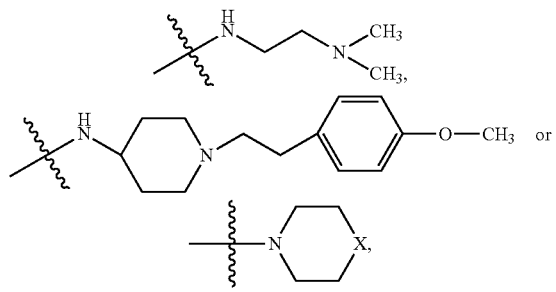

where X is O, S, NR$_{10}$ or N$^+$R$_{10}$R$_{10}$, where each R$_{10}$ is independently H, alkyl, substituted C$_2$-C$_{12}$ alkyl, alkenyl, substituted C$_4$-C$_{12}$ alkenyl, alkynyl, substituted alkynl, aryl, substituted aryl where the substituent is other than chloro when R$_1$ and R$_2$ are =O,

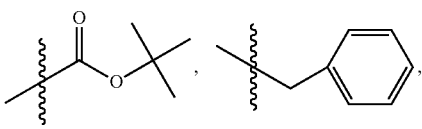

—CH$_2$CN, —CH$_2$CO$_2$R$_{11}$, —CH$_2$COR$_{11}$, —NHR$_{11}$, —NH$^+$(R$_{11}$)$_2$ where R$_{11}$ is alkyl, alkenyl or alkynl, each of which is substituted or unsubstituted, or H;

R$_5$ and R$_6$ taken together are =O; and R$_7$ and R$_8$ is each independently H, F, Cl, Br, SO$_2$Ph, CO$_2$CH$_3$, CN, COR$_{12}$, or SR$_{12}$, where R$_{12}$ is H or a substituted or unsubstituted alkyl, alkenyl or alkynyl.

The invention further provides the instant composition, wherein R$_3$ is O$^-$.

The invention further provides the instant composition, wherein R$_4$ is

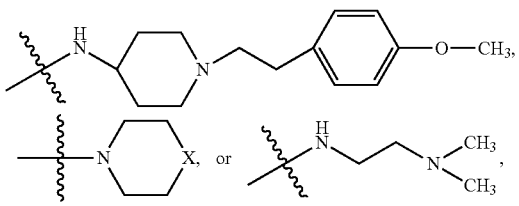

In an embodiment, the invention provides a compound having the structure (Compound 104)

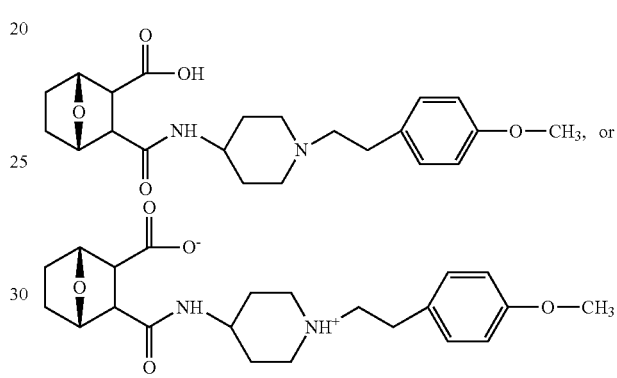

In an embodiment, the invention provides a compound having the structure (Compound 104E)

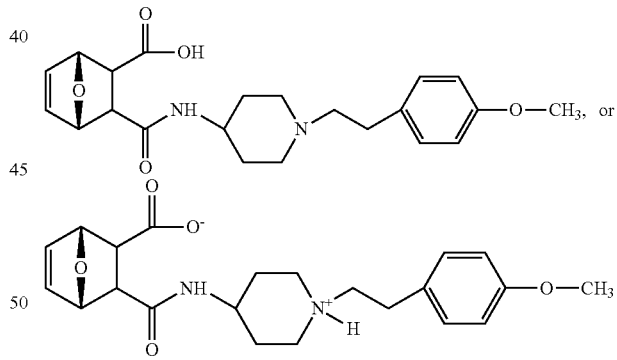

In an embodiment, the invention provides a compound having the structure (Compound 106)

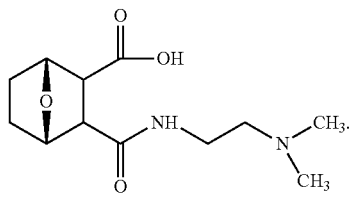 [SMILES: CN(C)CCNC(=O)C1C(C(=O)O)[C@H]2CC[C@@H]1O2]

In an embodiment, the invention provides a compound having the structure (Compound 106E)

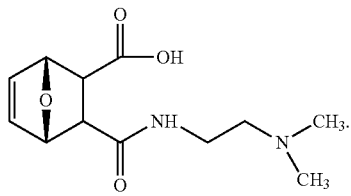 [SMILES: CN(C)CCNC(=O)C1C(C(=O)O)[C@H]2C=C[C@@H]1O2]

The invention further provides the instant composition, wherein $R_4$ is

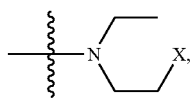

where X is O, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynl,

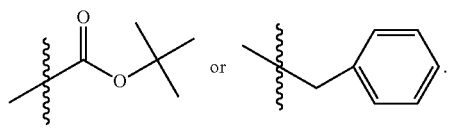

The invention further provides the instant composition, wherein $R_4$ is

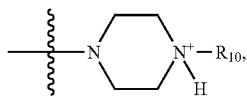

where $R_{10}$ H, alkyl, substituted $C_2$-$C_{12}$ alkyl, alkenyl, substituted $C_4$-$C_{12}$ alkenyl, alkynyl, substituted alkynyl, substituted aryl where the substituent is other than chloro when $R_1$ and $R_2$ are =O,

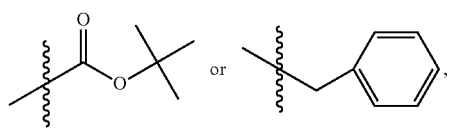

—$CH_2CN$, —$CH_2CO_2R_{11}$, —$CH_2COR_{11}$, —$NHR_{11}$, or $NH^+(R_{11})_2$, where R11 is H or alkyl.

The invention further provides the instant composition, wherein $R_4$ is

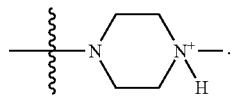

The invention further provides the instant composition, wherein $R_4$ is

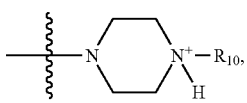

where $R_{10}$ is

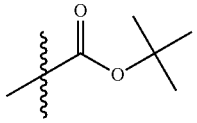

The invention further provides the instant composition, wherein $R_4$ is

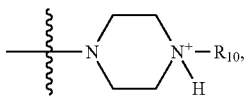

where $R_{10}$ is

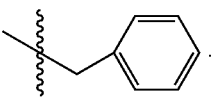 [SMILES: *Cc1ccccc1]

The invention further provides the instant composition, wherein $R_4$ is

The invention further provides the instant composition, wherein $R_4$ is

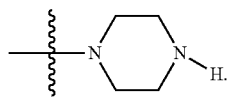

The invention further provides the instant composition, wherein $R_5$ and $R_6$ together are =O.

The invention further provides the instant composition, wherein $R_7$ and $R_8$ are each H.

The invention also provides a compound having the structure

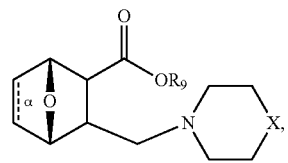

wherein bond α is present or absent; $R_9$ is present or absent and when present is H, $C_1$-$C_{10}$ alkyl, $C_2$-$C_{10}$ alkenyl or phenyl; and X is O, S, $NR_{10}$ or $N^+R_{10}R_{10}$, where each $R_{10}$ is independently alkyl, C2-C12 substituted alkyl, alkenyl, C4-C12 substituted alkenyl, alkynyl, substituted alkynyl, aryl, substituted aryl where the substitutent is other than chloro,

$-CH_2CO_2R_{11}$, $-CH_2COR_{11}$, $-CH_2CN$, or $-CH_2CH_2R_{16}$, where $R_{11}$ is H or alkyl, and where $R_{16}$ is any substitutent that is a precursor to an aziridinyl intermediate, or a salt, enantiomer or zwitterion of the compound.

In an embodiment, the invention provides the structure

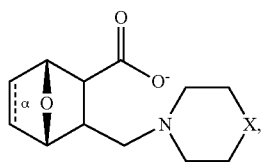

wherein, bond α is present or absent; X is O, S, $NR_{10}$ or $N^+R_{10}R_{10}$, where each $R_{10}$ is independently H, alkyl, $C_2$-$C_{12}$ substituted alkyl, alkenyl, $C_4$-$C_{12}$ substituted alkenyl, alkynyl, substituted alkynyl, aryl, substituted aryl where the substitutent is other than chloro,

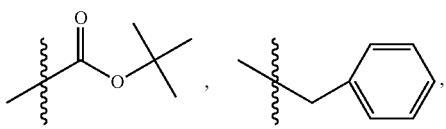

$-CH_2CO_2R_{11}$, $-CH_2COR_{11}$, $-CH_2CN$, or $-CH_2CH_2R_{16}$, where $R_{11}$ is H or alkyl, and where $R_{16}$ is any substitutent that is a precursor to an aziridinyl intermediate, or a salt, enantiomer or zwitterion of the compound.

The invention further provides an embodiment wherein X is O or $NH^+R_{10}$, where $R_{10}$ is H, alkyl, $C_2$-$C_{12}$ substituted alkyl, alkenyl, $C_4$-$C_{12}$ substituted alkenyl, alkynyl, substituted alkynyl, aryl, substituted aryl where the substitutent is other than chloro,

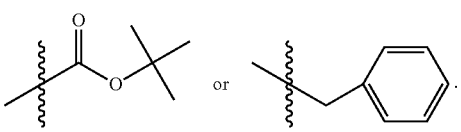

The invention further provides an embodiment wherein X is O.

The invention further provides an embodiment wherein X is $-CH_2CH_2R_{16}$, where $R_{16}$ is any substituent is a precursor to an aziridinyl intermediate.

The invention further provides an embodiment wherein X is $NH^+R_{10}$, where $R_{10}$ is H, alkyl, substituted C2-C12 alkyl, alkenyl, substituted C4-C12 alkenyl, alkynyl, alkynyl, aryl, substituted aryl where the substituent is other than chloro,

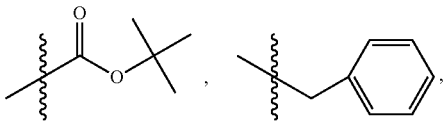

$-CH_2CO_2R_{11}$, $-CH_2COR_{11}$, $-CH_2CN$, or $-CH_2CH_2R_{16}$, where $R_{11}$ is H or alkyl, and where $R_{16}$ is any substitutent that is a precursor to an aziridinyl intermediate.

The invention further provides an embodiment, wherein $R_{10}$ is methyl.

The invention further provides an embodiment, wherein $R_{10}$ is

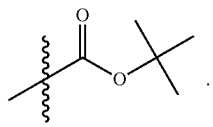 [SMILES: *C(=O)OC(C)(C)C]

The invention further provides an embodiment, wherein $R_{10}$ is

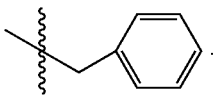

The invention further provides an embodiment, wherein $R_{10}$ is ethyl.

The invention further provides an embodiment, wherein $R_{10}$ is absent.

In another embodiment, the invention provides the structure

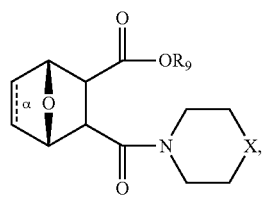

wherein $R_9$ is present or absent and when present is H, alkyl, alkenyl, alkynyl or phenyl; and X is O, $NR_{10}$ or $N^+R_{10}R_{10}$, where each $R_{10}$ is independently alkyl, C2-C12 substituted alkyl, alkenyl, C4-C12 substituted alkenyl, alkynyl, substituted alkynyl, aryl, substituted aryl where the substitutent is other than chloro,

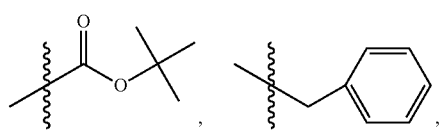

$-CH_2CO_2R_{11}$, $-CH_2COR_{11}$, or $-CH_2CN$, where $R_{11}$ is H or alkyl, or a salt, zwitterion or enantiomer of the compound.

In another embodiment of the invention, $R_{10}$ is cyclopropyl.

In another embodiment, the invention provides the structure

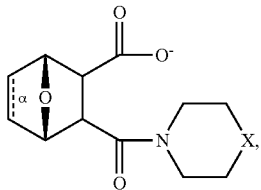

wherein X is O or $NH^+R_{10}$, where $R_{10}$ is present or absent and when present is alkyl, alkenyl or alkynyl, each of which is substituted or unsubstituted,

$-CH_2CO_2R_{11}$, $-CH_2COR_{11}$, or $-CH_2CN$, where $R_{11}$ is H or alkyl.

In an embodiment, the invention provides a compound having the structure (Compound 100)

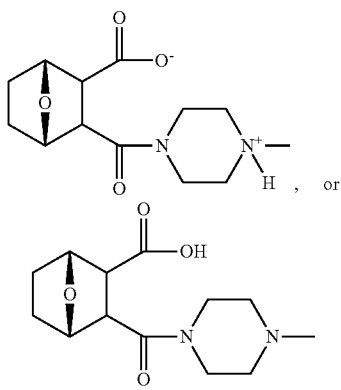

In an embodiment, the invention provides a compound having the structure (Compound 102)

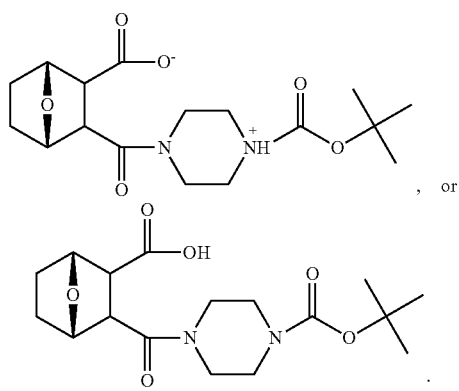

In an embodiment, the invention provides a compound having the structure (Compound 101)

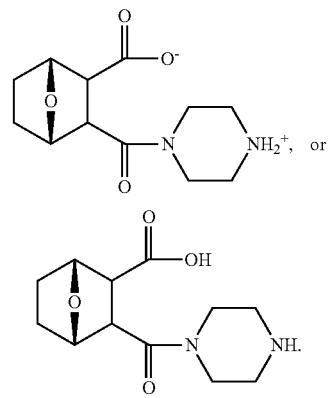

In an embodiment, the invention provides a compound having the structure (Compound 103)

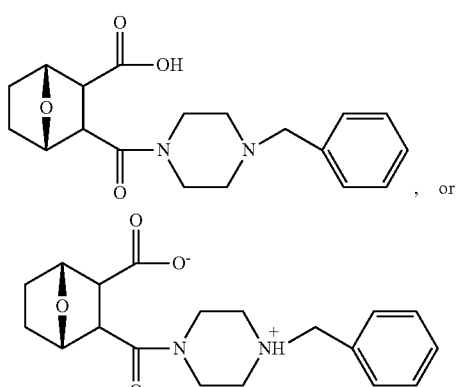

In an embodiment, the invention provides a compound having the structure (Compound 105)

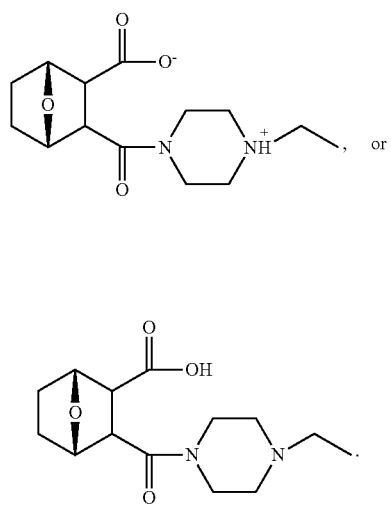 [SMILES: CCN1CCN(C(=O)C2C(C(=O)[O-])[C@H]3CC[C@@H]2O3)CC1 ; CCN1CCN(C(=O)C2C(C(=O)O)[C@H]3CC[C@@H]2O3)CC1]

In another embodiment, the invention provides the structure

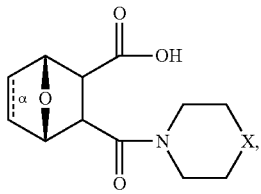

wherein X is O, NR$_{10}$ or NH$^+$R$_{10}$,
where R$_9$ is alkyl, alkenyl, alkynyl or aryl, and where R$_{10}$ is present or absent and when present is alkyl, alkenyl or alkynyl, each of which is substituted or unsubstituted,

—CH$_2$CO$_2$R$_{11}$, —CH$_2$COR$_{11}$ or —CH$_2$CN, where R$_{11}$ is H or alkyl.

In another embodiment of the invention, R$_{10}$ is cyclopropyl.

In an embodiment, the invention provides a compound having the structure (Compound 111)

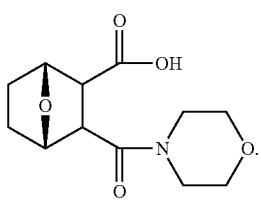

In an embodiment, the invention provides a compound having the structure (Compound 104E)

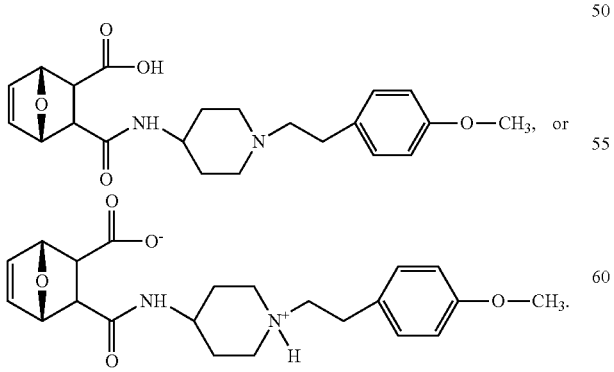

In an embodiment, the invention provides a compound having the structure (Compound 100E)

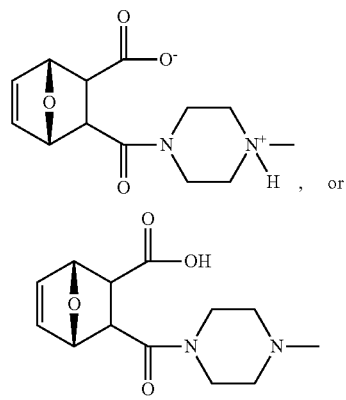

In an embodiment, the invention provides a compound having the structure (Compound 102E)

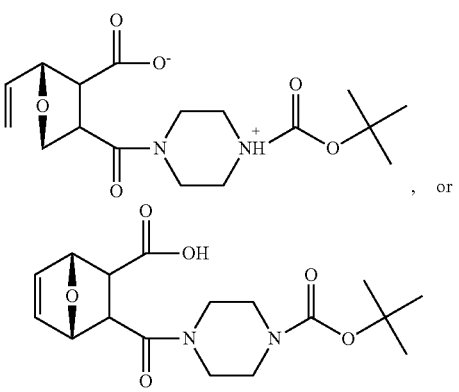

In an embodiment, the invention provides a compound having the structure (Compound 101E)

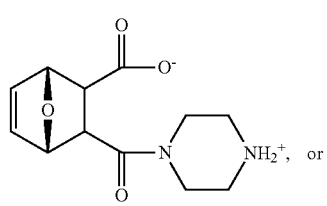

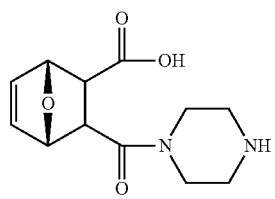

In an embodiment, the invention provides a compound having the structure (Compound 103E)

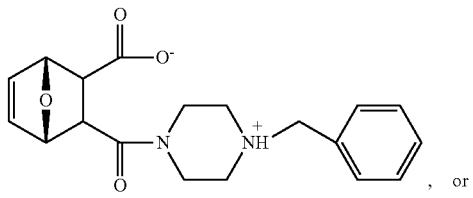

, or

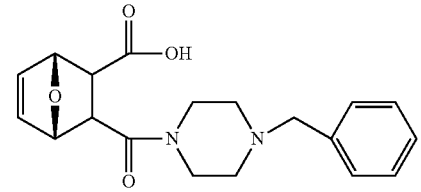

In an embodiment, the invention provides a compound having the structure (Compound 105E)

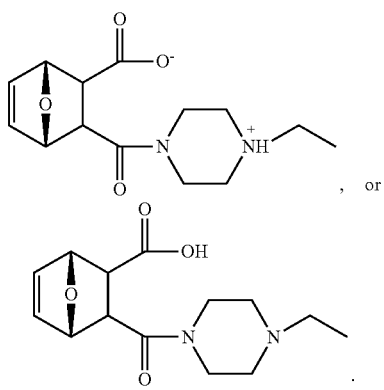

, or

In an embodiment, the invention provides a compound having the structure (Compound 111E)

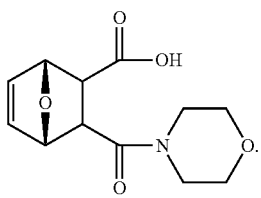 [SMILES: O=C(O)C1C(C(=O)N2CCOCC2)[C@@H]2CC[C@H]1O2]

This invention provides a compound having the structure (compound 106)

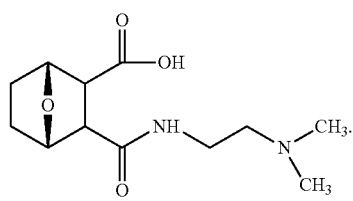 [SMILES: CN(C)CCNC(=O)C1C(C(=O)O)[C@H]2CC[C@@H]1O2]

This invention provides a compound having the structure (compound 106E)

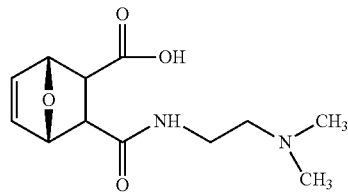 [SMILES: CN(C)CCNC(=O)C1C(C(=O)O)[C@H]2C=C[C@@H]1O2]

This invention provides a compound having the structure (compound 108)

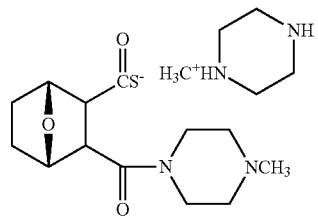

This invention provides a compound having the structure (compound 107)

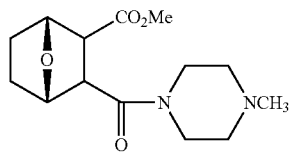 [SMILES: COC(=O)C1C(C(=O)N2CCN(C)CC2)[C@@H]2CC[C@H]1O2]

This invention provides a compound having the structure (compound 107E)

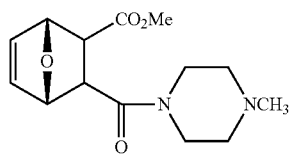 [SMILES: COC(=O)C1C(C(=O)N2CCN(C)CC2)[C@@H]2C=C[C@H]1O2]

In another embodiment, the invention provides a compound having the structure

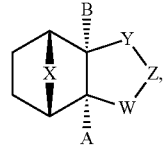

wherein A and B is each independently H, F, Cl, Br, SO$_2$Ph, CO$_2$CH$_3$, COR$_{14}$, SR$_{14}$, where R$_{14}$ is H or aryl or a substituted or unsubstituted alkyl, alkenyl or alkynyl; X is O, NH or S; Z is O, S, SR$_{15}$, NH, NR$_{15}$, CH$_2$OH, CH$_2$OR$_{15}$, where R$_{15}$ is an aryl or a substituted or unsubstituted alkyl, alkenyl or alkynyl; and Y and W is each independently CHOH CH$_2$, C=S or C=O, or a salt of the compound.

In an embodiment of the foregoing invention, Y and W are each independently CH$_2$ or C=S.

The invention further provides an embodiment wherein X is O; Z is S; and Y and W are each C=S.

The invention further provides an embodiment wherein A and B are each F.

The invention further provides an embodiment wherein A is H; and B is F.

In another embodiment, the invention provides a compound having the structure

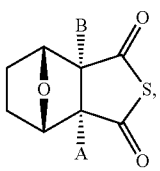

wherein A is F or $SR_{14}$, where $R_{14}$ is aryl or a substituted or unsubstituted alkyl, alkenyl or alkynyl; and B is F, Cl, Br, $SO_2Ph$, $CO_2CH_3$, or $SR_{14}$, where $R_{14}$ is aryl or a substituted or unsubstituted alkyl, alkenyl or alkynyl.

In a further embodiment, the invention provides the structures

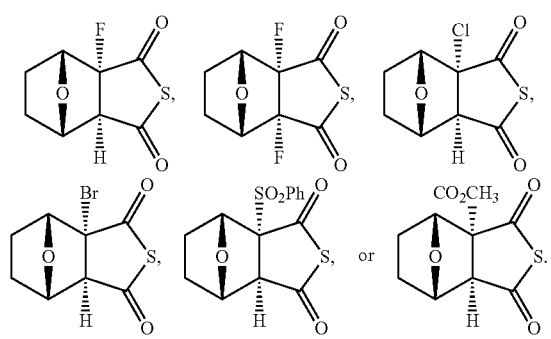

The invention provides a pharmaceutical composition comprising the compounds of the invention and a pharmaceutically acceptable carrier.

The invention also provides a process for making a compound comprising reacting a compound having the structure

with a compound having the structure

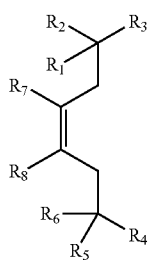

to form a compound having the following structure

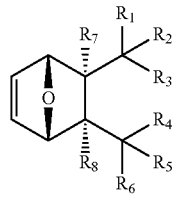

reacting a compound having the above structure with hydrogen in the presence of a catalyst to form

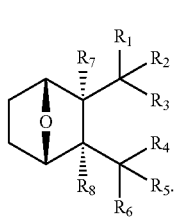

The invention also provides a process for making a compound comprising reacting a compound having the structure

with a compound having the structure

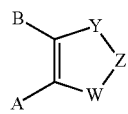

to form a compound having the following structure

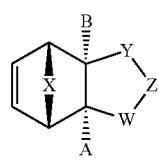

reacting a compound having the above structure with hydrogen in the presence of a catalyst a catalyst to form

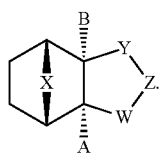

The invention also provides a process for making a compound having the structure

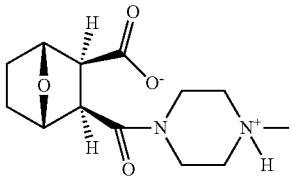 [SMILES: C[NH+]1CCN(C(=O)[C@@H]2[C@H](C(=O)[O-])[C@H]3CC[C@@H]2O3)CC1]

comprising
dissolving a compound having the following structure

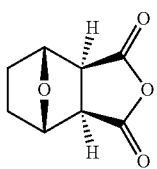 [SMILES: O=C1OC(=O)[C@H]2[C@@H]1[C@@H]1CC[C@H]2O1]

in benzene and adding a compound having the structure

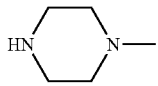

at room temperature to produce a compound having the structure

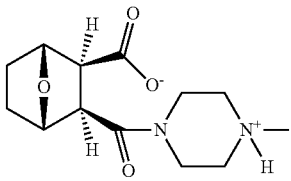 [SMILES: C[NH+]1CCN(C(=O)[C@@H]2[C@H](C(=O)[O-])[C@H]3CC[C@@H]2O3)CC1]

and recrystallizing the compound produced from a hot solvent.

The invention also provides a process for making a compound comprising
dissolving a compound having the following structure

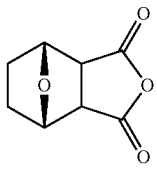

in benzene and adding a compound having the structure

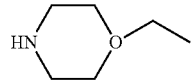

at room temperature to produce a compound having the structure

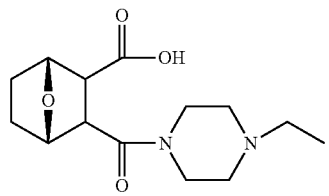 [SMILES: CCN1CCN(C(=O)C2C(C(=O)O)[C@H]3CC[C@@H]2O3)CC1]

recrystallizing the compound produced from a hot solvent.

In an embodiment, the solvent is dimethylformamide (DMF) or ethanol.

The invention provides a method of treating a patient suffering from a tumor overexpressing N-CoR comprising administering to the patient one or more of the compounds of this invention, alone or in combination with one or more retinoid receptor ligand, or one or more histone deacetylase ligands, or both, in each case in an amount effective to treat the patient.

In an embodiment, the compound is selected from Compound 100 and Compound 105.

In the method of the invention, the histone deacetylase ligand may be an inhibitor, e.g. the histone deacetylase inhibitor of HDAC-3 (histone deacetylase-3). The histone deacetylase ligand may also be selected from the group consisting of 2-amino-8-oxo-9,10-epoxy-decanoyl, 3-(4-aroyl-1H-pyrrol-2-yl)-N-hydroxy-2-propenamide, APHA Compound 8, apicidin, arginine butyrate, butyric acid, depsipeptide, depudecin, HDAC-3, m-carboxycinnamic acid bis-hydroxamide, N-(2-aminophenyl)-4-[N-(pyridin-3-yl-methoxycarbonyl) aminomethyl] benzamide, MS 275, oxamfiatin, phenyLbutyrate, pyroxamide, scriptaid, sirtinol, sodium butyrate, suberic bishydroxamic acid, suberoylanilide hydroxamic acid, trichostatin A, trapoxin A, trapoxin B and valproic acid.

The compounds of this invention may be used in combination with compounds which inhibit the enzyme histone deacetylase (HDAC). These HDAC enzymes post-translationally modify histones (U.S. Patent Publication No. 2004/0197888, Armour et al.) Histones are groups of proteins which associate with DNA in eukaryotic cells to form compacted structures called chromatin. This compaction allows an enormous amount of DNA to be located within the nucleus of a eukaryotic cell, but the compact structure of chromatin restricts the access of transcription factors to the DNA. Acetylation of the histones decreases the compaction of the chromatin allowing transcription factors to bind to the DNA. Deacetylation, catalysed by histone deacetylases (HDACs), increases the compaction of chromatin, thereby reducing transcription factor accessibility to DNA. Therefore, inhibitors of histone deacetylases prevent the compaction of chromatin, allowing transcription factors to bind to DNA and increase expression of the genes.

In the methods of the invention, an assessment of the percentage of cells with N-CoR in the cytoplasm relative to the percentage of cells with N-CoR in the nucleus is representative of the ratio of the number of more-differentiated cells to the number of less-differentiated cells in a given tissue.

In the method of the invention, tumors that overexpress N-CoR may include glioblastoma multiforme, breast cancer, colorectal cancer, small cell lung cancer or ovarian cancer.

This invention also provides a method of inhibiting growth of a tumor overexpressing N-CoR in a patient, comprising administering to the patient one or more of the compounds of this invention, alone or in combination with one or more retinoid receptor ligand, one or more histone deacetylase ligand, or both, in each case in amounts effective to affect N-CoR so as to thereby induce differentiation of cells of the tumor overexpressing N-CoR and inhibit growth of the tumor in the patient.

In an embodiment, the compound is selected from Compound 100 and Compound 102.

In the methods of the invention, an assessment of the percentage of cells with N-CoR in the cytoplasm relative to the percentage of cells with N-CoR in the nucleus is representative of the ratio of the number of more-differentiated cells to ratio of less-differentiated cells in a given tissue.

In the method of the invention, tumors that overexpress N-CoR may include glioblastoma multiforme, breast cancer, colorectal cancer, small cell lung cancer or ovarian cancer.

The invention further contemplates a method of controlling undesired vegetation comprising contacting the vegetation or its environment with a herbicidally effective amount of the compounds of the invention.

The invention further contemplates a method of inhibiting plant phosphatase activity comprising contacting the plant or its environment with a herbicidally effective amount of the compounds of the invention.

This invention further contemplates a method of preventing or treating fungal infections in a subject comprising administering to the subject an effective amount of the compounds of this invention.

This invention further contemplates a method of treating cancer in a subject comprising administering to the subject an effective amount of the compounds of the invention.

This invention further contemplates a method of treating a subject afflicted with breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, or acute lymphocytic leukemia comprising administering to the subject a therapeutically effective amount of the compounds of the invention, thereby treating the subject.

The invention further contemplates the use of prodrugs which are converted in vivo to the compounds of the invention (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter a reactive site) or the pharmacokinetics of the compound.

In an embodiment of the invention the compound has the structure

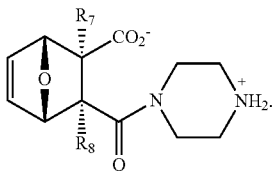

In an embodiment of the invention the compound has the structure

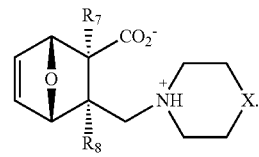

As used herein, "zwitterion" means a compound that is electrically neutral but carries formal positive and negative charges on different atoms. Zwitterions are polar, have high solubility in water and have poor solubility, in most organic solvents.

Aziridines are organic compounds sharing the aziridine functional group which is a three membered heterocycle with one amine group and two methylene groups. Precursors to aziridinyl intermediates include compounds known to those skilled in the art which readily provide arizidinyl intermediates under suitable conditions.

The compounds described in the present invention are in racemic form or as individual enantiomers. The enantiomers can be separated using known techniques, such as those described, for example, in Pure and Applied Chemistry 69, 1469-1474, (1997) IUPAC.

As used herein, "overexpressing N-CoR" means that the level of the Nuclear receptor co-repressor (N-CoR) expressed in cells of the tissue tested are elevated in comparison to the levels of N-CoR as measured in normal healthy cells of the same type of tissue under analogous conditions. The nuclear receptor co-repressor (N-CoR) of the subject invention may be any molecule that binds to the ligand binding domain of the DNA-bound thyroid hormone receptor ($T_3R$) and retinoic acid receptor (RAR). (U.S. Pat. No. 6,949,624, Liu et al.) Examples of tumors that overexpress N-CoR may include glioblastoma multiforme, breast cancer (Myers et al.), colorectal cancer (Giannini and Cavallini), small cell lung carcinoma (Waters et al.) or ovarian cancer (Havrilesky et al.).

"Solvent" as used herein is intended to include compounds such as, hexanes, benzene, toluene, diethyl ether, chloroform, methylene chloride, ethyl acetate, 1,4-dioxane, water, THF, acetone, acetonitrile, DMF, DMSO, acetic acid, n-butanol, isopropanol, n-propanol, ethanol, methanol, formic acid, carbon tetrachloride, benzenethiol, chlorobenzene, cyclohexanethiol, 1-diethylaminoethanol, ethylene dichloride, ethylene glycol, xylene, 1,1,2,2-tetrachloroethane, phenol, acetic acid, 1-butanol, 2-butanol, 2-butanone, diglyme, dimethylether, dioxane, petroleum ether, (NMP) N-methyl-2-pyrrolidinone, heptane, glycerin, HMPA (Hexamethylphosphorus triamide), MTBE (methyl t-butyl ether), nitromethane, pyridine, 1-propanol, 2-propanol, and triethylamine.

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds therefore may be in a salt form. As used herein, a "salt" is a salt of the instant compounds which has been modified by making acid or base salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. For a description of possible salts, see, e.g., Berge et al. (1977) "Pharmaceutical Salts", *J. Pharm. Sci.* 66:1-19.

As used herein, "therapeutically effective amount" means an amount sufficient to treat a subject afflicted with a disease (e.g. tumors overexpressing N-CoR) or to alleviate a symptom or a complication associated with the disease.

As used herein, "herbicidally effective" means an amount sufficient to adversely affect plant growth, particularly through inhibition of plant phosphatase 2 A activity.

As used herein, "treating" means slowing, stopping or reversing the progression of a disease, particularly tumors overexpressing N-CoR.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, ..., n−1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, ..., n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2, ..., n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, Liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Discussion

We found that one protein found to have increased expression in glioblastoma multiforme (GBMs) as compared to normal brain is nuclear receptor co-repressor (N-CoR), a regulator of the normal neural stem cell pool. Expression of N-CoR in GBM was confirmed by immunohistochemistry and Western blotting.

N-CoR is expressed in the nucleus of neural stem cells (NSCs). (Hermanson et al. (2002)) Following phosphatidyl-inositol-3-OH kinase/Akt1 kinase-dependent phosphorylation, N-CoR translocates to the cytoplasm and leads to astrocytic differentiation of NSCs. The nuclear retention of N-CoR, therefore, is essential for the maintenance of NSCs in the undifferentiated state (Hermanson et al.). Analogous to $CD133_+$ NSC found within the developing brain, brain tumor stem cells (BTSC) bearing CD133 have been identified within GBM. (Uchida et al. (2000); and Singh et al. (2003)) BTSC are capable of proliferation, self-renewal, and differentiation. BTSC, but not CD133—differentiated tumor cells, are able to recapitulate tumors upon xenograft transplantation. (Singh et al. (2004)).

Retinoids, metabolites of vitamin A, have been examined therapeutically in a variety of tumors, including gliomas. (Yung et al. (1996)) N-CoR is closely associated with the retinoid receptor and is released upon ligand binding to the receptor. (Bastien et al. (2004)) We hypothesized that one effect of retinoids on malignant gliomas may be the induction of differentiation by the binding of retinoids to the retinoid receptor followed by dissociation of the N-CoR/retinoid receptor complex and translocation of N-CoR to the cytoplasm. This idea would explain the previous observation of increase GFAP expression in a glioma cell line (U343 MG-A) treated with retinoids. (Rudka et al. (1988)) To test this we targeted two different sites, individually or simultaneously, within the N-CoR pathway by treating the GBM cell line U343 MG-A with 50 µM of retinoic acid (RA) and/or 10 nM of okadaic acid (OA), a protein phosphatase-1 and protein phosphatase-2A inhibitor. By preventing the action of protein phosphatase-1 and protein phosphatase-2A, okadaic acid increases the phosphorylated form of N-CoR and promotes its subsequent cytoplasmic translocation. (Hermanson et al. (2002))

Cell line U343 MG-A is available from the University of California at San Francisco (UCSF) Brain Tumor Research Center Tissue Bank. (University of California, San Francisco, Health Sciences West building, San Francisco, Calif. 94143-0520.) In addition, cell lines U343 and U87 are commercially available from EPO-GmbH, Robert-Rössle-Str.10, 13092 Berlin-Buch, Germany.

Several molecules that have anti-PP2A activity synergize with retinoic acids in inhibiting the growth of cells of tumors that overexpress N-CoR in vitro. The most effective group of phosphatase inhibitors synergizing with retinoic acids that have been evaluated are analogues of the ancient therapeutic agent, mylabris, derived from the crushed bodies of the blister beetle, in which the principal active agent is cantharidin, a known potent inhibitor of PP2A (Wang, 1989; Peng et al., 2002).

Cantharidin has anti-tumor activity against human cancers of the liver (hepatomas) and of the upper gastrointestinal tract but is toxic to the urinary tract (Wang, 1989). Norcantharidin, a demethylated cantharidin, maintains anti-tumor activity of cantharidin against hepatomas and cancers of the stomach and esophagus, but has little or no urinary tract toxicity. Norcantharidin also stimulates white blood cell production in patients and mice, a phenomenon not understood mechanistically, but a pharmacological effect of potential benefit as an anticancer agent (Wang et al., 1986; Wang, 1989).

The publication of a report that cantharidin acts as a protein phosphatase inhibitor prompted a more general interest in compounds with this type of chemical structure (Li and Casida, 1992). Previously, it had been found that the simpler congener and its hydrolysis product (commercially available as the herbicide, Endothall) are hepatoxic (Graziano and Casida, 1997). The primary targets in liver appear to be the protein phosphatases PP2A and PP1, all of the compounds showing $ED_{50}$ values at the micromolar level. Binding studies have shown that the action of certain cantharidin homologs is direct on PP2A and indirect on PP1 (Honkanen et al., 1993; Li et al., 1993). Phosphatase PP1B is affected only at millimolar levels of these compounds, whereas the enzyme PP2C is not influenced at all.

In the past, several cantharidin analogues had been synthesized and evaluated for anti-phosphatase activity and for their ability to inhibit the growth of cancer cells in culture (Sakoff and McClusky, 2004; Hart et al., 2004). Some of the previously evaluated modified norcantharidin molecules inhibited the growth of several human tumor cell lines. The activity of norcantharidin analogues against cells of tumors overexpressing N-CoR or the activity of norcantharidins combined with other potential anti-tumor agents was not analyzed. Further studies included 16 "modified norcantharidins" evaluated for activity against four human tumor cell lines including ovarian, kidney, colorectal and lung as well as a mouse leukemia line. None were as active as single agents as cantharidin or norcantharidin and none were evaluated for activity in combination with another antitumor agent (McCluskey et al., US Patent Application Publication No. 2006/0030616, 2006).

A different series of cantharidin analogues had been previously synthesized and evaluated as pesticides and for antitumor activity against cancer cell lines. Forty-three analogues of endothal and cantharidin have been developed and assessed for their activity as herbicides and their lethality to mice (Matsuzawa et al., 1987). Endothal thioanhydride was shown to be a more potent herbicide than endothal but was toxic to the liver of mice (Matsuzawa et al., 1987; Kawamura et al., 1990).

More recently, it has been found that endothal thioanhydride is an active agent against PP2A and PP1 in vivo (Erdodi et al., 1995). Endothal and endothal thioanhydride, like cantharidin, inhibit the activity of PP2A and to some extent, the activity of PP1 (Erdodi et al., 1995). In the liver, the principal target appears to be PP1. In fibroblasts, only endothal thioanhydride caused marked morphological changes whereas cantharidin and endothal did not (Erdodi et al., 1995). The enhanced activity of endothal thioanhydride in vivo is thought to be related to its enhanced lipophilicity resulting in increased diffusion across the plasmalemma (Essers et al., 2001). A more recent publication has described the synthesis of the mono-, and the di-fluoro analogues of Endothal and also the corresponding anhydrides, however no pharmacological data accompanied this synthetic work (Essers et al., 2001).

Of the known congeners of this type of compound, only the parent, cantharidin and its bis(normethyl)-derivative, norcantharidin, have seen any use as anti-cancer drug substances and only norcantharidin is used as an anti-neoplastic agent (Tsauer et al., 1997).

In pursuing the development of new drug substances in this area, we have found it essential to develop inhibitors that have greater specificity, especially towards those enzymes which display high activity against the replication processes of cancer cells. High specificity also holds out the possibility of avoiding targets important to normal cell function. From the point of view of the physical characteristics of any newly-developed drug substance, it must preeminently have good membrane permeability (i.e., has a log P value of between 2 and 4 units).

The compounds described herein have an antagonistic effect on phosphatase-2A and phosphatase 1. We have confirmed that at least Compounds 100, 105, and 102 are effective in inhibiting the growth of cells of tumors overexpressing N-CoR. Compounds 100 and 105 are advantageous over other cantharidin homologs as they exist as zwitterions, which renders them water soluble and stable at acid pH, features desirable for orally effective drugs. Compound 102 is lipid soluble, which affords a greater ability than Compounds 100 and 105 to cross the blood-brain barrier. This is especially important when treating such tumors as glioblastoma multiforme.

Compound 100, norcantharidin (nor-Can), endothal (End), and endothal thioanhydride (ET) were evaluated for their ability to inhibit the growth of GBMs in a dose dependent manner in vivo as shown in FIG. 1.

From graphic plots of the glioblastoma multiforme GBM cell line U373 (available from the National Institute of Neurological Disorders and Stroke Molecular Pathogenesis Unit, Building 10, Room 5 D37, National Institutes of Health, 900 Rockville Pike, Bethesda, Md., 20892) as a function of exposure to different doses of drug for 7 days, the concentration of each compound that inhibited brain tumor cell proliferation by 50% (IC50) was estimated. The IC50s expressed in micro-molarity (µM), were: 2.5, 3.0, 12.0, and 15.0 for endothal thioanhydride, Compound 100, norcantharidin, and endothal respectively as seen in FIG. 1. As shown, on a molar basis, Compound 100 was a potent inhibitor of GBMs in vitro.

In combination with anti-phosphatases, retinoids synergistically inhibit the proliferation of glioblastoma multiforme. Synergism (potentiation) of the inhibitory activity of two drugs in combination is said to be present when the percent survival in the presence of two drugs is greater than the sum of the percent survivals of the two drugs used alone at the same doses in the combination.

Figure 2:
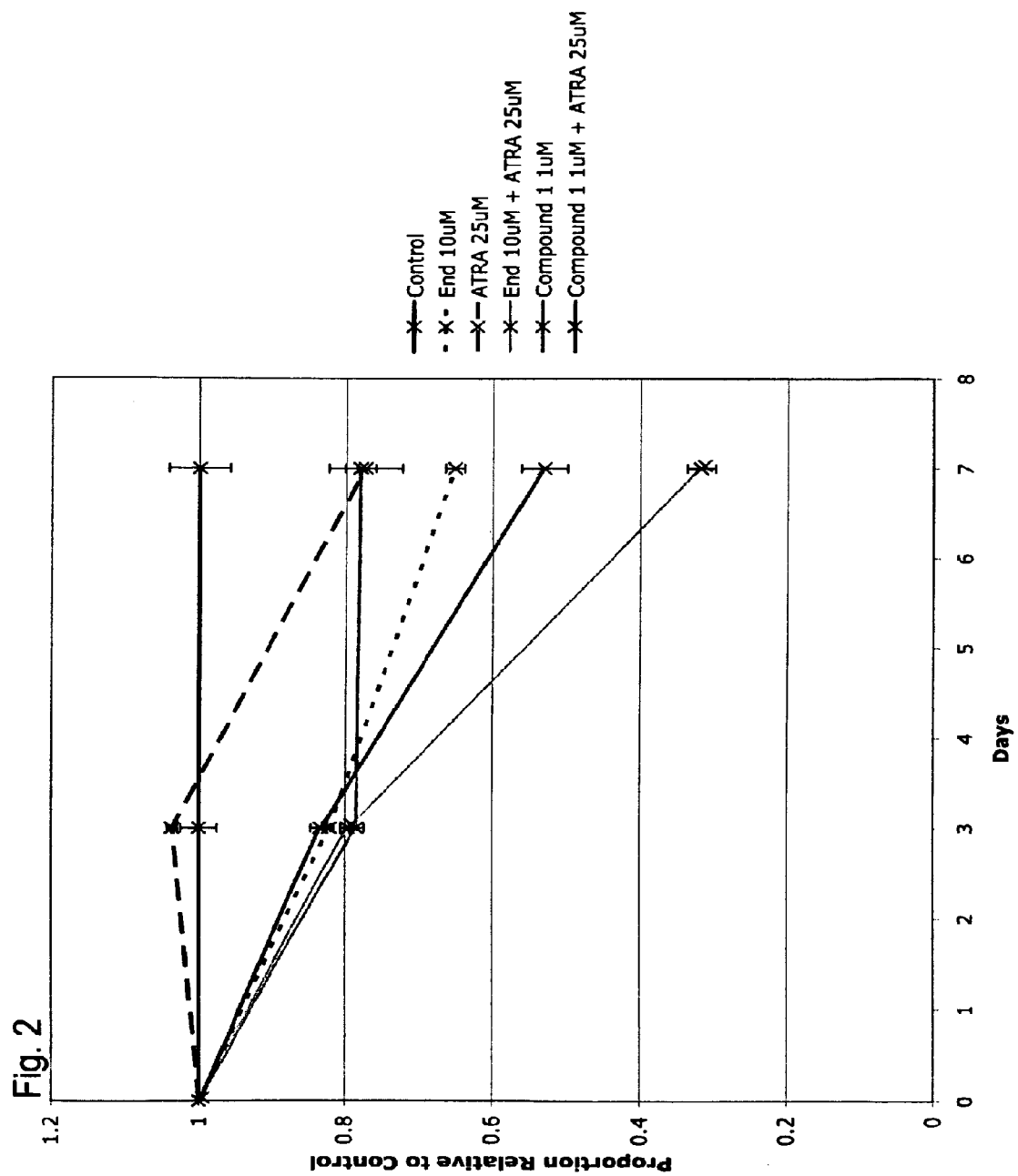
FIG. 2: Inhibition of gliomal cell line U373 treated with endothal (End) or Compound 100 or each with and without all-trans Retinoic acid (ATRA) for 7 days. Individual treatment with endothal and Compound 100 shows modest inhibition of growth. Combination of End or Compound 100 with ATRA shows synergistic reduction in cell growth. Error bars indicate SD.

The inhibitory activity of Compound 100 was further evaluated in combination with retinoids as well as individually. As shown in FIG. 2, the combination of Compound 100 with all-trans retinoic acid (ATRA) demonstrated a synergistic reduction in cell growth.

The expected percent survival of U373 cells exposed to the combination of ATRA and End is 50% (77% by ATRA× 65% by End=50%) whereas the observed survival was 32%. The expected percent survival in the presence of the combination of ATRA and Compound 100 is 60% (77% by ATRA×78% by Compound 100-60%), whereas the observed survival was 53%.

To determine whether there is tumor type specificity of the inhibitory properties of PP2A inhibitors, retinoic acid and Trichostatin A we measured their inhibitory effects as single agents against the GBM line U373, a breast cancer line, MCF-7 (obtained from ATCC) and a kidney cancer cell line, UMRC (UMRC obtained by Dr. Zhuang, NINDS, NIH from the Intramural Research Support Program, SAIC, National Cancer Institute, Frederick Cancer Research and Development Center).

Figure 3:
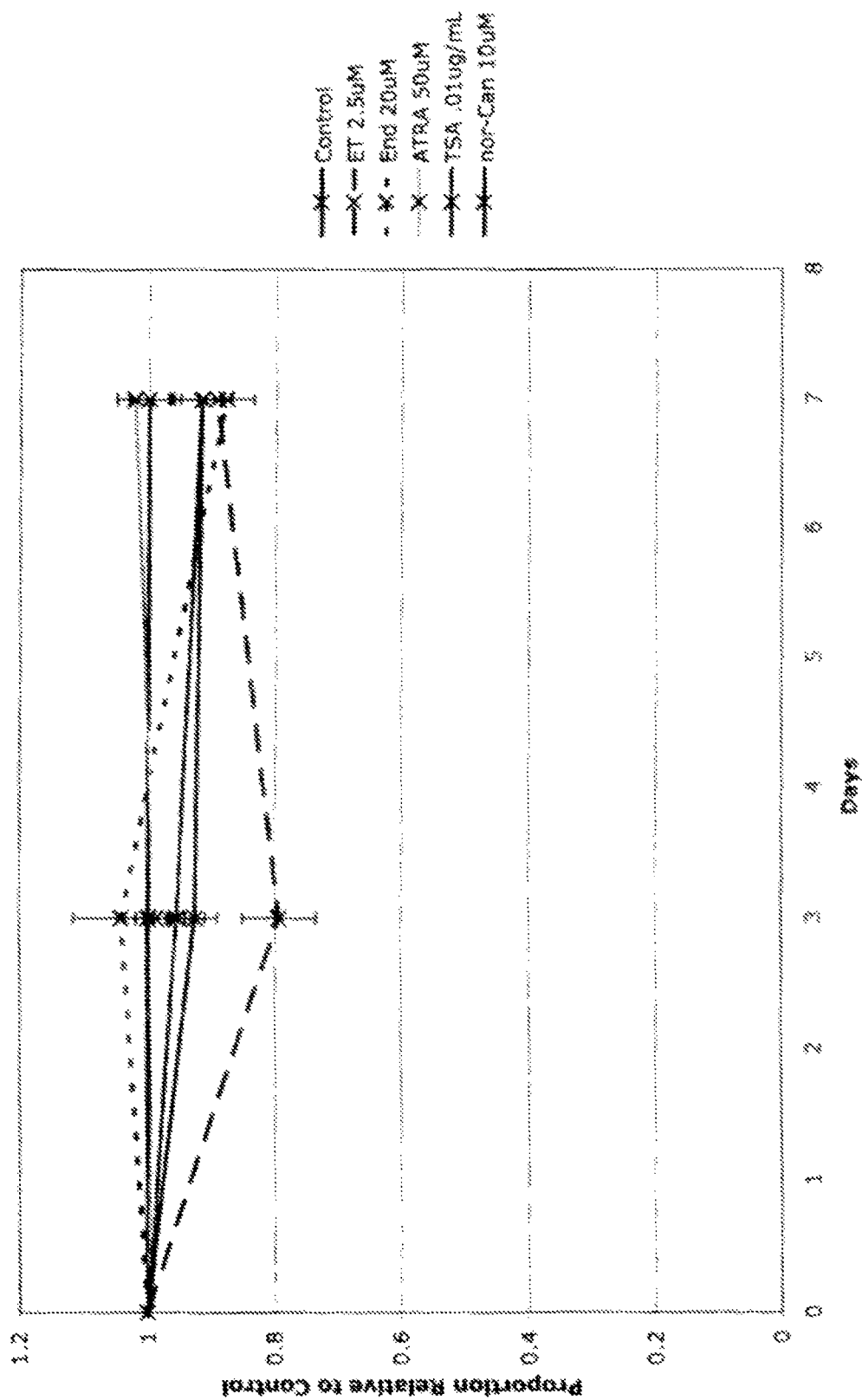
FIG. 3: Inhibition of growth of kidney cancer cell line, UMRC by endothal thioanhydride (ET), endothal (End), all-trans Retinoic Acid (ATRA), Trichostatin A (TSA) and norcantharidin (nor-Can) for 7 days. Error bars indicate SD.
Figure 4:
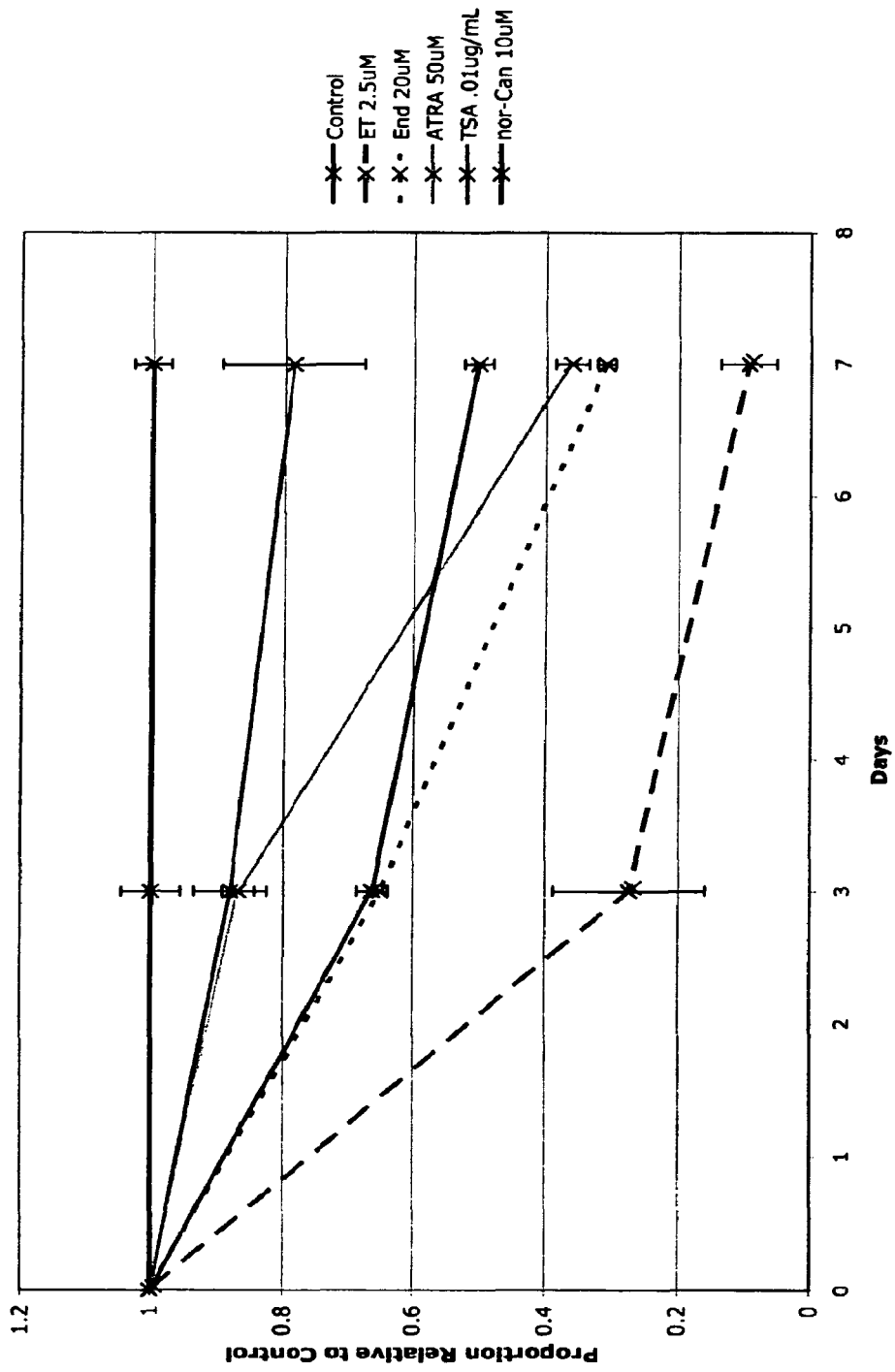
FIG. 4: Inhibition of growth of gliomal cell line U373 by endothal thioanhydride (ET), endothal (End), all-trans Retinoic Acid (ATRA), Trichostatin A (TSA) and norcantharidin (nor-Can) for 7 days. Individual treatment with endothal thioanhydride showed the greatest inhibition of growth. Error bars indicate SD.
Figure 5:
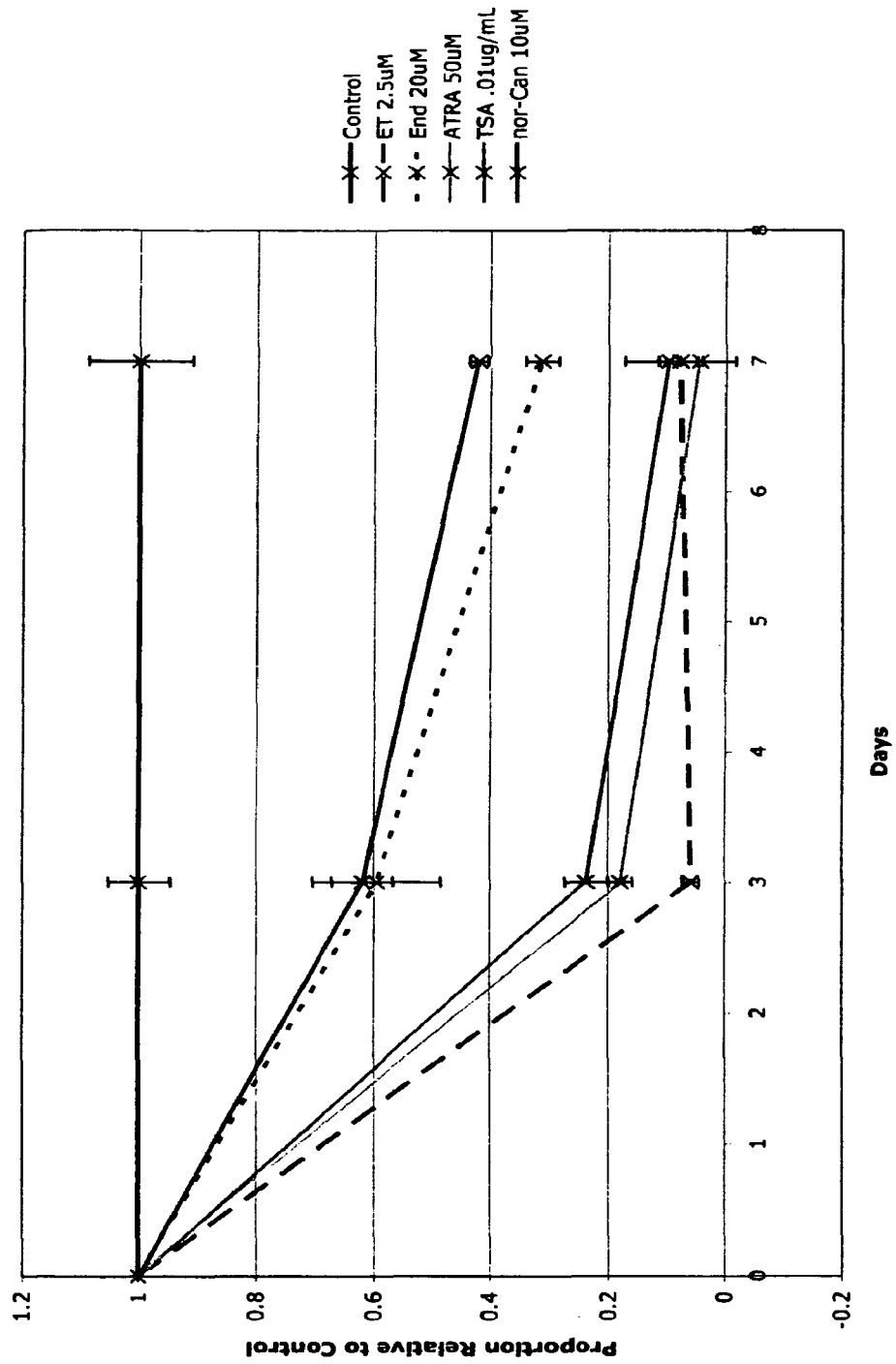
FIG. 5: Inhibition of growth of breast cancer cell line, MCF-7 by Inhibition of UMRC by endothal thioanhydride (ET), endothal (End), all-trans Retinoic Acid (ATRA), Trichostatin A (TSA) and norcantharidin (nor-Can) for 7 days. Treatment with individual doses of endothal, ATRA and TSA showed an inhibition in growth. Error bars indicate SD.

The kidney cancer cell line, UMRC (FIG. 3) was less sensitive than the brain tumor line, U373 (FIG. 4) whereas the breast cancer line, MCF-7 (FIG. 5) was as sensitive as U373 to all-trans retinoic acid, endothal thioanhydride, norcantharidin, endothal, and Trichostatin A. There is some cell type specificity of these drugs for GBMs. The activity of the drugs against MCF-7 cells indicates that regimens being developed for brain tumor treatment are likely also useful against breast cancer and other tumors that overexpress N-CoR.

We have shown that Compound 100 will have similar inhibitory effects in the treatment of breast cancer and other tumors that overexpress N-CoR due to the structural similarities of Compound 100 to endothal as well as their similar effects in the treatment of glioblastoma multiforme.

Endothal is also known as an active defoliant and potent contact herbicide used in many agricultural situations. It is considered effective as a pre-harvest desiccant and as a selective pre-emergence herbicide (Crafts, 1953).

Endothal, norcantharidins and cantharidin are all well known inhibitors of mammalian protein phosphatase as well as potent herbicides (Matsuzawa et al., 1987). The mechanism by which endothal and other homologs exert their potent herbicidal activity has not been studied extensively despite the widespread use of endothal internationally in agriculture. It should be noted that endothal is water soluble where cantharidin and norcantharidin are not.

It was assumed that the activity of endothal as a contact herbicide and defoliant is related to the known irritating toxicity of its parent compound, norcantharidin. However, more recent studies suggest that the herbicidal activity of endothal may be a function primarily of its anti-plant protein phosphatase (PP2A) activity. Li et al. (1993) showed that cantharidin and endothal inhibit spinach leaf PP2A and PP1 and inhibit the activation of nitrate reductase by light in the intact spinach leaf, a process mediated by PP2A. Smith et al. (1994) demonstrate that the structurally unrelated protein phosphatase inhibitors okadaic acid and calyculin-A are potent inhibitors at nanomolar concentrations of the growth of certain plants. The activity of okadaic acid and calyculin-A strongly suggest that the activity of endothal as an herbicide is due to its anti-phosphatase activity.

Baskin and Wilson (1997) showed inhibitors of serine-threonine protein phosphatases including cantharidin inhibit organization of plant microtubules. Ayaydin et al. (2000) show that endothal inhibited PP2A activity causing alteration of cell division in cultured alfalfa cells. They noted that endothal was cell permeable.

Like endothal, Compounds 100 and 105 are water soluble. But unlike endothal, which is a diacid, Compounds 100 and 105 may be zwitterions. The fact that compounds disclosed herein such as Compound 100 are more potent than endothal against mammalian cancer cell growth may be due to greater cell permeability of the zwitterions than the diacid. Compounds 100 and 105 are more potent herbicides on a molar basis because of better cell penetration. Compounds 100 and 105, as zwitterions, are also less toxic to distributors and applicators of the herbicide as well as to the public inadvertently exposed to the agent. Compounds 100 and 105 do not have the acidic character of endothal.

The compounds herein, including Compounds 100 and 105, therefore, are useful, commercially feasible, and safer herbicides both with respect human exposure and to the environment.

EXPERIMENTAL DETAILS

Methods and Materials

Preparation of Endothall Anhydride

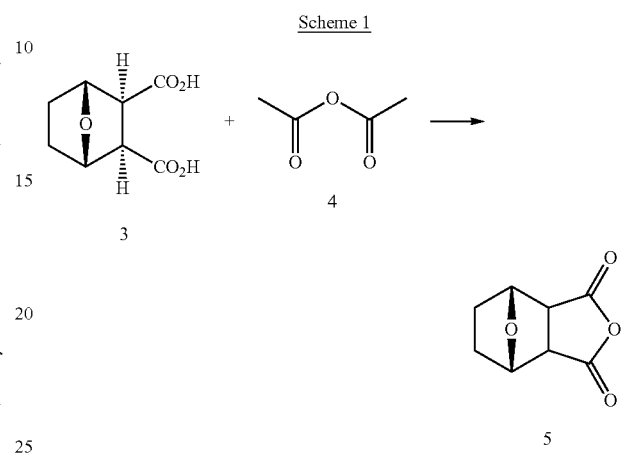

As shown in scheme 1, we prepared endothal anhydride by adding acetic anhydride (0.5 mL)(4) to a suspension of Endothall (186 mg) (3) in benzene (3 mL) and the mixture was then stirred until the solid had gone into solution (2 hours). The solution was heated under vacuum to remove the benzene and the residue was then heated at 80° C. for 30 min. Petroleum ether (5 mL) was then added and the desired anhydride spontaneously crystallized. The product was removed by filtration washed with a little petroleum ether to give the pure product (85 mg) which was used immediately in the following two preparations.

Preparation of Endothall 4-Methylpiperazine Monoamide (EMPM) (Compound 100)

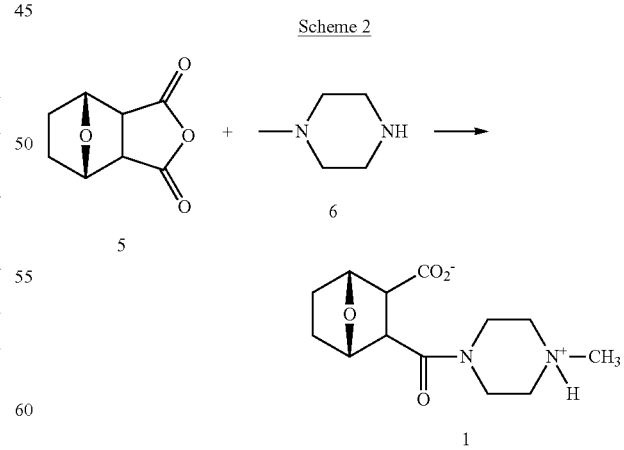

Endothall anhydride (85 mg)(5) prepared as described above was dissolved in benzene (2 mL) and N-methylpiperazine (60 mg)(6) was added in one portion at room temperature. Almost immediately a white crystalline appeared. The mixture was left at room temperature overnight and the product was then removed by filtration washed with a little benzene then dried (145 mg). A negative ion mass spectrum showed a parent ion at m/z 267 (theo. 267) confirming the molecular weight as 268 mass units. The product was recrystallized from hot DMF to give 95 mg of the pure monoamide, Compound 100 (1) m.p. 226-227° C. with some decomposition beginning at 224° C. The $^1$HNMR spectrum of the sodium salt of compound 100 confirms the structure. Sodium salt. $^1$H NMR: (D$_2$O): 1.41-1.70 (m, 4H), 2.18 (s, 3H), 2.21-2.55 (m, 4H), 2.92 (d, 1H), 3.17 (d, 1H), 3.22-3.40 (m, 2H), 3.45 (m, 2H), 4.60 (q, 1H), 4.78 (q, 1H). Mass spectrometry data measuring the mass to charge ratio of compound 100 showed peaks at 141 m/z, 167 m/z, 254 m/z 199 m/z and 185 m/z corresponding to negatively charged fragments (Table 1).

Preparation of Endothall 4-Ethylpiperazine Monoamide (EEPM) (Compound 105)

Endothal anhydride (1.68 g; 10 mmol) and N-ethylpiperazine (3.42 g; 30 mmol) were added to 10 mL of toluene and heated under reflux for 18 h. The solvent was then evaporated under reduced pressure and the residue was crystallized from methyl t-butyl ether to give the crude product (1.8 g). Recrystallization from the same solvent gave a total of 1.2 g (42.5% yield) in two crops. m.p. 215-218° C. (with decomposition). The $^1$H NMR of the sodium salt in D$_2$O and the MS negative ion spectrum confirm the structure and molecular weight (m/z 282.2 ams), respectively. Sodium salt. $^1$H NMR: (D2O): 0.95 (t, 3H), 1.42-1.65 (m, 4H), 2.20-2.42 (m, 4H), 2.43-2.55 (m, 2H), 2.93 (d, 1H), 3.08 (d, 1H), 3.20-3.33 (m, 2H), 3.42-3.58 (m, 2H), 4.45 (q, 1H), 4.75 (q, 1H). The MS spectrum indicates the presence of the association dimer at m/z 563.3 ams, which could be expected for a zwitterion. In addition, a trace of Endothal (MS m/z 185 ams) is present but this is not evident in the NMR spectrum. A negative ion mass spectrum showed a parent ion at 282.2 m/z (theo. 282.2) confirming molecular weight as 282.2 mass units.

Preparation of 4-(3-Carboxy-7oxa-bicyclo[2.2.1]heptane-2-carbonyl)piperazine-1-carboxylic acid tert-butyl ester (Compound 102)

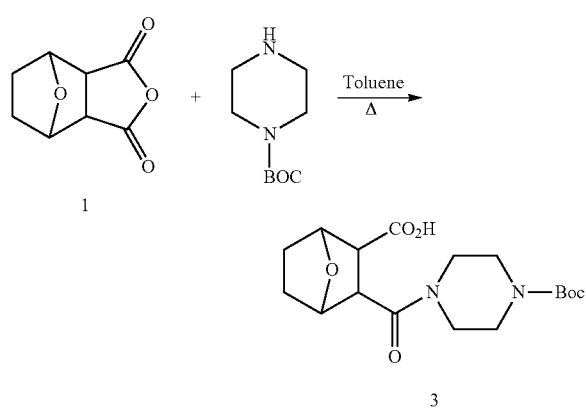

Endothal anyhydride (1) (500 mg, 3 mmole) and N-BOC piperazine (2) (1.86 g, 10 mmole) were added to dry toluene (8 mL) and heated at 100-110° C. for 8 h. The solvent was removed on a rotary evaporator and to the residue was added a mixture of 10% aqueous citric acid (20 mL) and ethyl acetate (20 mL). The separated solid (compound 102) (3) was filtered, washed with hexane and dried under vacuum. Yield 500 mg (47%). mp 206-208° C. The mass spectrum and the $^1$HNMR data confirmed the identity of compound 102. Mass spectrometry data measuring the mass to charge ratio of compound 102 showed peaks at 141.1 m/z, 185 m/z, and 354 m/z. $^1$H NMR: (DMSO-d$_6$): 1.42 (s, 9H), 1.45-1.72 (m, 4H), 3.02-3.15 (d, 1H), 3.20-3.55 (m, 9H), 4.65-4.70 (m, 2H).

Preparation of 3-(1-[2-(4-Methoxy-phenyl)-ethyl]piperidin-4-ylcarbamoyl)-7-oxa-bicyclo[2.2.1]-heptane-2-carboxylic acid (Compound 104)

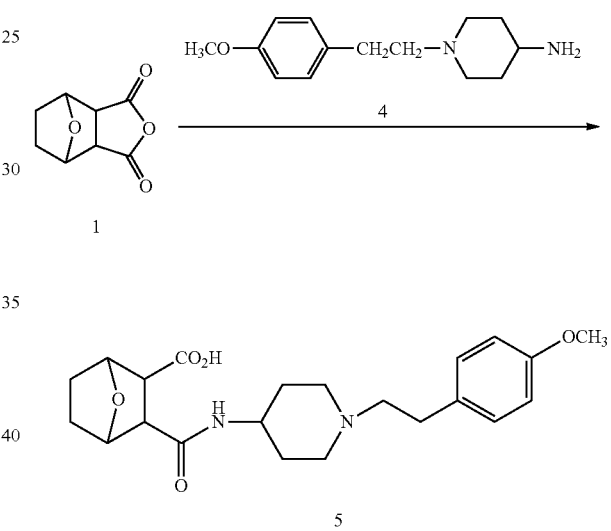

Endothal anhydride (1) (500 mg, 3 mmole) and amine (4) (2.34 g, 10 mmole) were added to dry toluene (8 mL) and heated at 100° C. for 20 h. The solvent was then evaporated under reduced pressure and the residue was taken in water and the solution was acidified to pH to 5.5 to 6 with dilute HCl. The solid which was filtered and recrystallized from methanol to give pure (5) (compound 104). Yield 450 mg (36%). Mp 140-142° C. The mass spectrum and the $^1$HNMR data confirmed the identity of compound 104. Mass spectrometry data measuring the mass to charge ratio of compound 104 showed peaks at 385. $^1$H NMR: (CDCl$_3$): 1.48-1.65 (m, 4H), 1.78-1.95 (m, 2H), 1.98-2.15 (t, 2H), 2.40-2.60 (m, 4H), 2.68-2.78 (m, 2H), 2.80 (s, 2H), 3.02-3.15 (d, 2H), 3.78 (s, 3H), 3.82-3.98 (m, 1H), 4.82-4.88 (m, 2H), 6.78-6.82 (d, 2H), 7.09-7.12 (d, 2H).

Preparation of 3-(4-Benzylpiperazine-1-carbonyl)-7-oxa-bicyclo[2.2.1]heptane-2-carboxylic acid (Compound 103): This compound was prepared in 3 steps starting from Endothal anhydride (1) as shown below in Scheme-1.

SCHEME-1

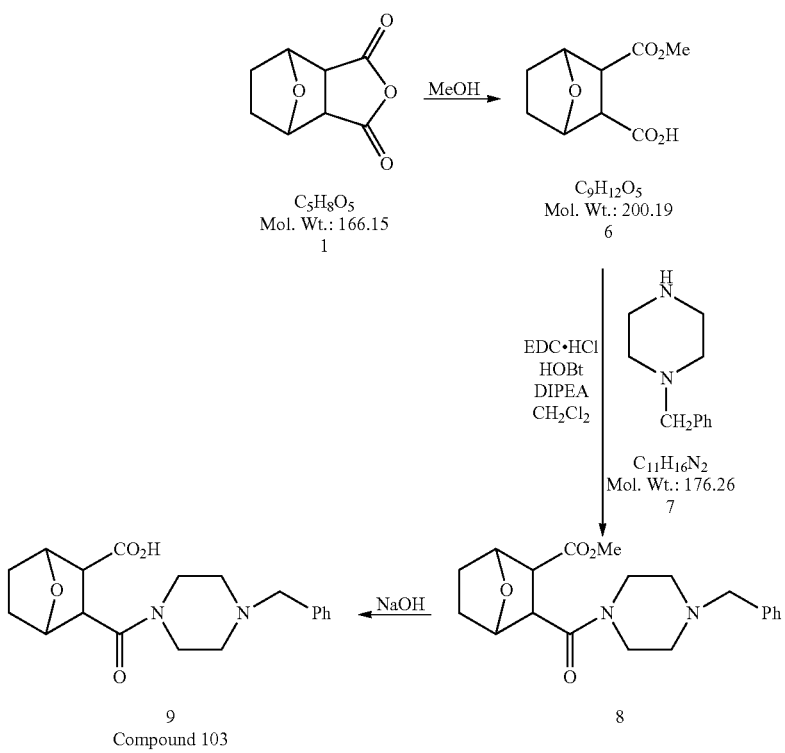

Step 1: Preparation of 7-Oxa-bicyclo[2.2.1]heptane-2,3-dicarboxylic acid monomethyl ester Endothal anhydride (1) (4 g, 24 mmole) was heated under reflux in dry methanol (20 mL) for 3 h. The reactions mixture was cooled to room temperature and the separated solid (6) was filtered and crystallized from methanol. Yield 4.6 g (96%). Mp 114-146° C.

Step 2: Preparation of 3-(4-Benzyl-piperazine-1-carbonyl)-7-oxa-bicyclo[2.2.1]heptane-2-carboxylic acid methyl ester (8)

To the mixture of acid derivative (6) (2.6 g, 13 mmole) in methylene chloride (40 mL) was added EDC.HCL (2.75 g, 15 mmole) followed by HOBt (150 mg). The mixture was stirred for 10 minutes at room temperature before adding N-benzyl piperazine (7) (1.76 g) followed by DIPEA (3.5 mL, 20 mmole). The reaction mixture was stirred at room temperature overnight. Water was added to the reaction mixture, the methylene chloride layer was separated, washed once with aqueous $NaHCO_3$, then dried over $NaSO_4$, filtered and concentrated. The crude residue was purified by column chromatography using 1-2% methanol in methylene chloride as the eluant to give the required pure material (8). Yield 2.7 g. (58%).

Step 3: Preparation of 3-(4-Benzyl-piperazine-1-carbonyl)-7-oxa-bicyclo[2.2.1]heptane-2-carboxylic acid (Compound 103)

To a solution of ester (8)(2.50 g, 7 mmole) in methanol (20 mL) was added aqueous NaOH (360 mg dissolved in 5 mL of water) and was stirred at room temperature overnight. The solvent was then evaporated to dryness, water (20 mL) was added and the pH of the solution was then adjusted to pH 5 using 6N HCL. It was then evaporated to dryness, and methylene chloride (30 mL) was added. The residual solid NaCl was removed by filtration and the filtrate was concentrated. The resulting solid was triturated with isopropyl ether to give the pure acid (9) (compound 103). Yield 1.8 g (75%). mp >190° C. (dec). The mass spectrum and the $^1$HNMR data confirmed the identity of compound 103. $^1$H NMR: ($CDCl_3$): 1.45-1.84 (m, 4H), 2.45-2.68 (m, 2H), 2.75-2.95 (m, 2H), 3.12-3.35 (m, 2H), 3.38-3.55 (m, 2H), 3.60-3.80 (m, 2H), 3.95-4.20 (m, 2H), 4.75-4.85 (m, 2H), 7.40 (s, 5H). Mass spectrometry data measuring the mass to charge ratio of compound 103 showed peaks at 177.2 m/z, 345 m/z and 711 m/z.

Preparation of 3-(Piperazine-1-carbonyl)-7-oxa-bicyclo[2.2.1]heptane-2-carboxylic acid (Compound 101)

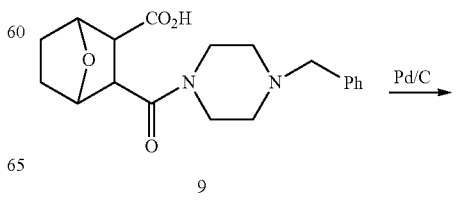

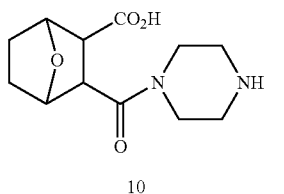

The N-Benzylprotected acid derivative (9) (500 mg, 1.45 mmole) in methanol was hydrogenated using hydrogen balloon over a Pd/C (5%, 50 mg) catalyst at room temperature overnight. The reaction mixture was filtered from the catalysts and concentrated to dryness. The crude residue was crystallized from 2-proponal to give amine (10) (Compound 101) as pure white solid. Yield 215 mg (58%) mp >240° C. (dec). The mass spectrum and the $^1$HNMR data confirmed the identity of Compound 101. $^1$H NMR: (CDCl$_3$-CD$_3$OD): 1.42-1.78 (m, 4H), 2.92-3.15 (m, 8H), 3.52-3.82 (m, 2H), 4.58 (q, 1H), 4.78 (q, 1H). Mass spectrometry data measuring the mass to charge ratio of compound 101 showed peaks at 177.2 m/z, 255.2 m/z, 277.2 m/z and 318.2 m/z.

Preparation of 3-(Piperazine-1-carbonyl)-7-oxa-bicyclo[2.2.1]heptane-2-carbothioic acid salt of N-methyl puperazine (Compound 108)

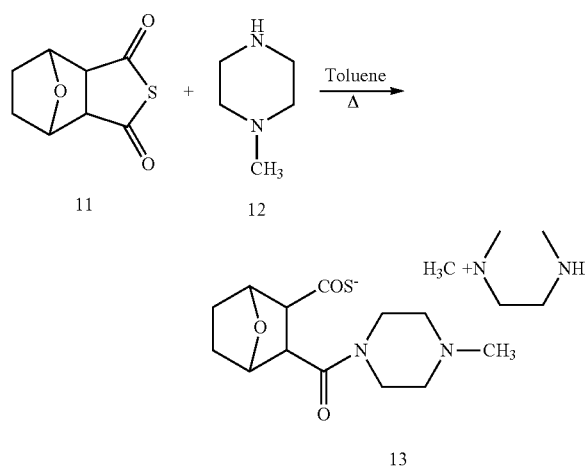

Endothal thioanhydride (11) (552 mg, 3 mmole) and N-methyl piperazine (12)(1 g, 10 mmole) were added to dry toluene (10 mL) and heated under reflux for 2.5 h. The reaction mixture was cooled to room temperature and the solid which had separated was filtered and crystallized from methylene chloride/ethyl acetate to give pure required (13) (Compound 108). Yield 585 mg (51%) mp >180° C. (dec). The mass spectrum and the $^1$HNMR data confirmed the identity of Compound 108. $^1$H NMR: (CDCl$_3$): 1.52-1.56 (m, 2H), 1.82-1.85 (m, 2H), 2.27 (s, 3H), 2.28-2.42 (m, 11H), 3.01 (s, 3H), 3.28-3.36 (m, 2H), 3.42-3.49 (m, 4H), 3.60-3.78 (m, 2H), 4.89-4.91 (m, 2H). Mass spectrometry data measuring the mass to charge ratio of compound 108 showed peaks at 217 m/z, 251 m/z and 351 m/z.

Preparation of 3-(4-Methyl-piperazine-1-carbonyl)-7-oxa-bicyclo[2.2.1]2-carboxylic acid methyl ester (Compound 107)

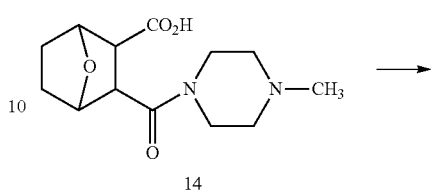

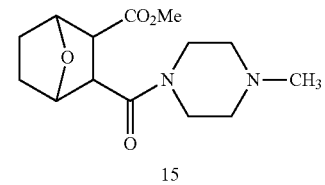

To a suspension of acid derivative (14) (536 mg, 2 mmole) in methylene chloride was added thionyl chloride (0.5 mL) followed by 2 drops DMF. The reaction mixture was stirred at room temperature overnight. It was a suspension of acid chloride hydrochloride salt. Added dry methanol (10 mL) and stirred for 30 minutes and evaporated to dryness using rotary evaporator. To the residue added water (20 mL) and extracted with ethyl acetate (20 mL). The aqueous layer pH was adjusted to 4.5 using aqueous NaHCO3 (10%) and evaporated to dryness. The residue was azeotroped with acetonitrile. It was again dissolved in acetonitrile and the separated NaCl was removed by filtration. The filtrate was evaporated to dryness and triturated with ethyl acetate to get a sticky solid, which was dried in a vacuum oven to get the required compound as a colorless solid (15) (Compound 107). Yield 140 mg (25%, mp 105-107° C.). The $^1$HNMR data were compatible with the expected spectrum for compound 107. $^1$H NMR: (D2O): 1.49-1.53 (m, 2H), 1.60-1.64 (m, 2H), 2.8 (s, 3H), 2.96-3.36 (m, 10H), 3.52 (s, 3H), 4.84-4.86 (m, 2H). Mass spectrometry data measuring the mass to charge ratio of compound 107 showed peaks at 123 m/z, 183 m/z, 251 m/z and 283 m/z.

Preparation of 1-[N-(3-Exocarboxy-7-oxabicyclo [2.2.1]heptane-2-exocarbonyl)amino-2-(N,N-dimethyl) aminoethane (Compound 106)

Endothal anhydride (1.68 g; 10 mmole) and unsym-N,N-dimethlethylene diamine (2.64 g; 30 mmole) were added to toluene (10 mL) and heated under reflux for 2 h. The solvent was then removed by evaporation under reduced pressure and the residue was triturated with a little di-isopropyl ether to cause crystallization. The product was then recrystallized twice from hexane by cooling to −20° C. The pure product (1.9 g; 74% yield) melted at 48-50° C. The $^1$HNMR spectrum is in perfect agreement with the structure which is zwitterionic and undergoes an exchange of two protons when treated with D$_2$O. The mass spectrum also confirmed the identity of Compound 106. $^1$H NMR: (CDCl$_3$): 1.62-1.75 (m, 2H), 1.85-1.95 (m, 2H), 2.2 (s, 6H), 2.45 (t, 2H), 2.92 (s, 2H), 3.60 (t, 2H), 4.85-4.95 (m, 2H). Mass spectrometry data measuring the mass to charge ratio of compound 106 showed peaks at 239.2 m/z, 257 m/z and 513 m/z.
Mass Spectrometry Table 1 shows the correlation between the mass to charge ratio of the ions and corresponding structures. A sample of the compound 100 was ionized in the mass spectrometer. Ions of different masses were separated and their relative abundance was measured

TABLE 1

| Mass to Charge Ratio of Ions | |
| --- | --- |
| Mass to Charge Ratio (m/z) | Theoretical Structure of Ions |
| 141 | [structure: bicyclic with O, $CO_2^-$] |
| 167 | [structure: bicyclic with O, $CO_2^-$, and *CHO] |
| 254 | [structure: bicyclic with O, $CO_2^-$, and piperazine amide, $N^+H$] |
| 199 | [structure: $^-O_2C$-CH=CH-C(O)-piperazine-$N^+H$] |
| 185 | [structure: $CO_2^-$-CH$_2$-CH$_2$-C(O)-piperazine-N—H] |

Table 2 shows the correlation between the mass to charge ratio of the ions and corresponding structures. A sample of the compound 105 was ionized in the mass spectrometer. Ions of different masses were separated and their relative abundance was measured

TABLE 2

| Mass to Charge Ratio of Ions | |
| --- | --- |
| Mass to Charge Ratio (m/z) | Theoretical Structure of Ions |
| 141 | [structure: bicyclic with O, $CO_2^-$] |
| 167 | [structure: bicyclic with O, $CO_2^-$, *CHO] |

TABLE 2-continued

| Mass to Charge Ratio of Ions | |
| --- | --- |
| Mass to Charge Ratio (m/z) | Theoretical Structure of Ions |
| 249 | [structure: bicyclic with O, C(O)-piperazine-N-ethyl] |
| 199 | [structure: $^-O_2C$-CH=CH-C(O)-piperazine-$N^+H$] |
| 185 | [structure: $CO_2^-$-CH$_2$-CH$_2$-C(O)-piperazine-N—H] |

EXAMPLE 1

Effect of Compound 100 and Related Analogues on GBM Cells

To identify novel therapeutic targets for the treatment of glioblastoma multiforme (GBM), cantharidin analogues were evaluated for their ability to inhibit growth of glioblastoma multiforme cells. Specifically, GBM cell line U373 was used in evaluations.

The cantharidin homologs that were evaluated were norcantharidin (nor-Can), which is a bis(normethyl) cantharidin; endothal (End), which is a dicarboxylic acid derivative of norcantharidins; endothal thioanhydride (ET); and Compounds 100 and 105, prepared as described above.

Cells were plated in triplicate on day one with and without different amounts of each drug dissolved in media (Compound 100, Compound 105, and endothal) or in dimethylsulfoxide (endothal thioanhydride and norcantharidin). The total number of cells is counted in the triplicate cultures at each dose and in controls after 7 days and the average number of cells and the standard deviation is determined.

The amount of inhibition of GBM cell growth is expressed as the proportion of the number of cells in the experimental dishes compared to the number of cells in control dishes containing only the drug vehicle and culture medium. The average percent of control is plotted and bracketed by one standard deviation calculated from the triplicate measurements.

Results

Each of the norcantharidin analogues inhibited the growth of GBMs in a dose dependent manner in vivo as shown in FIG. 1.

From graphic plots of the GBM cell line U373 as a function of exposure to different doses of drug for 7 days, the concentration of each compound that inhibited brain tumor cell proliferation by 50% (IC50) was estimated. The IC50s expressed in micro-molarity (uM), were: 2.5, 3.0, 12.0, and 15.0 for endothal thioanhydride, Compound 100, norcantharidin, and endothal respectively as seen in FIG. 1.

Figure 6:
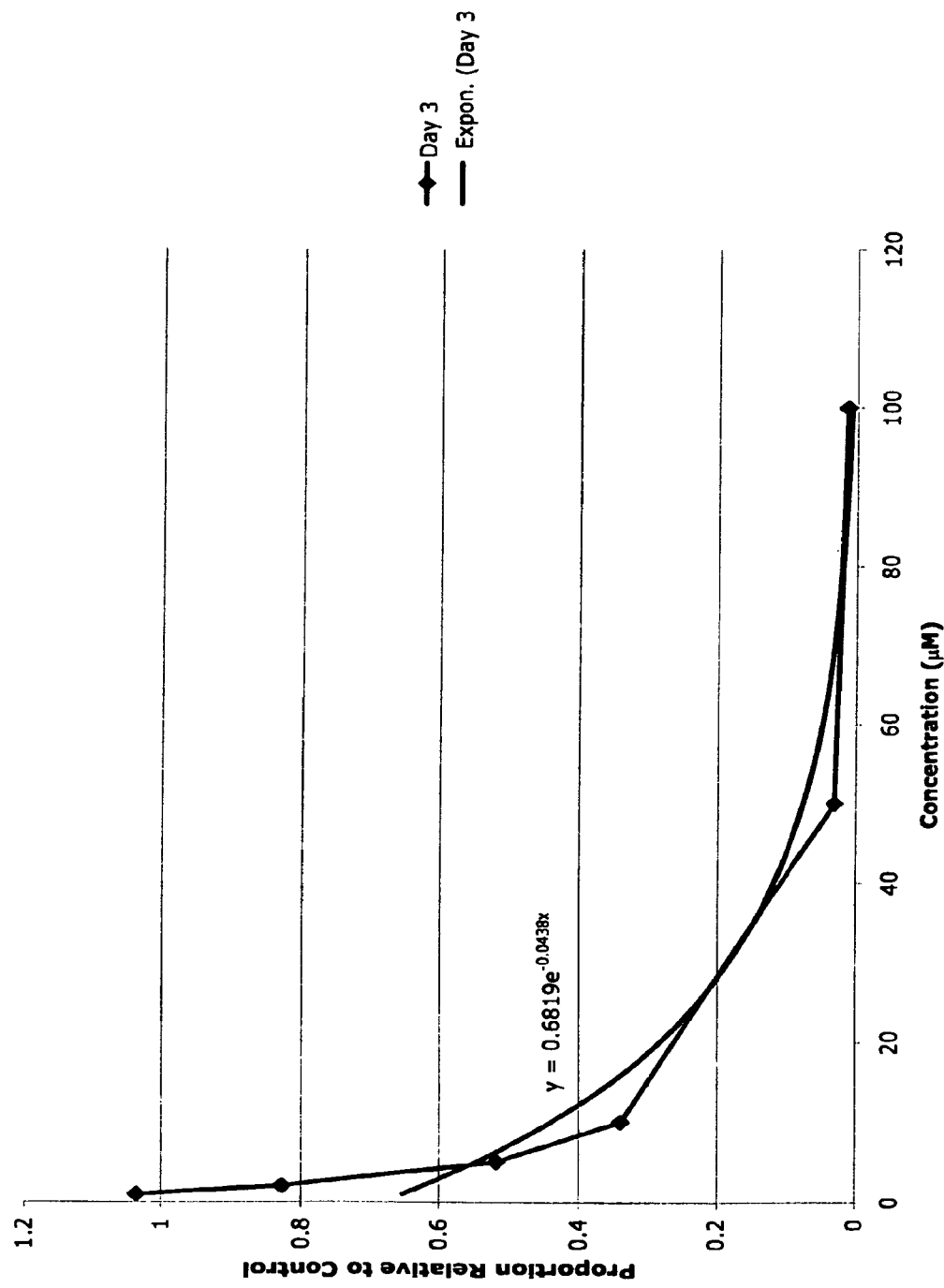
FIG. 6: Logarithmic curve of gliomal cell line U373 treated with 1-(3-Exocarboxy-7-oxabicyclo[2.2.1]heptane-2-exocarbonyl)-4-ethylpiperazine (Compound 105) after three days. Increasing dosages demonstrate a greater inhibition of growth.
Figure 7:
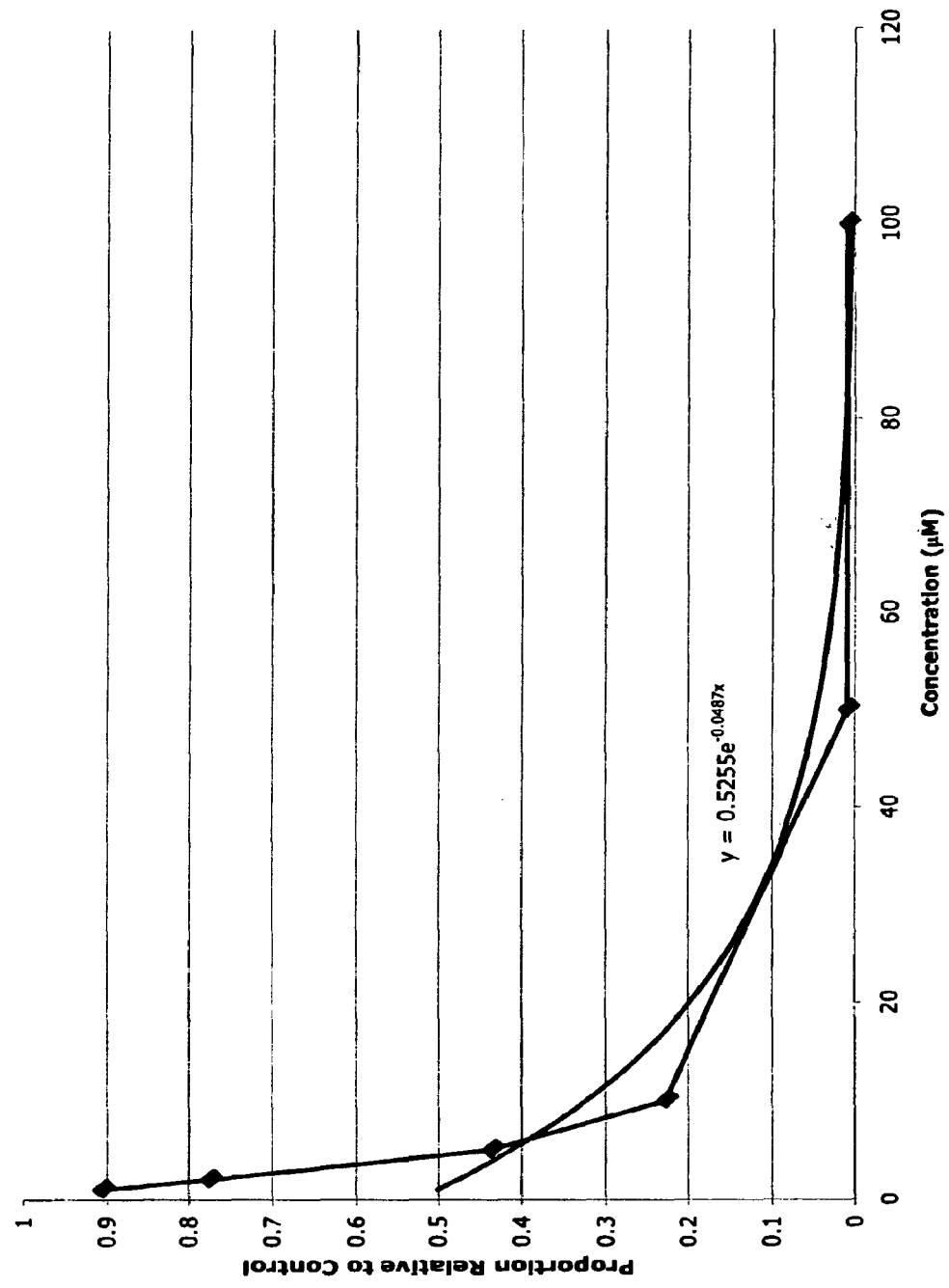
FIG. 7: Logarithmic curve of human GBM cell line U373 treated with 1-(3-Exocarboxy-7-oxabicyclo[2.2.1]heptane-2-exocarbonyl)-4-ethylpiperazine (Compound 105) after seven days. Increasing dosages demonstrate a greater inhibition of growth.
Figure 8:
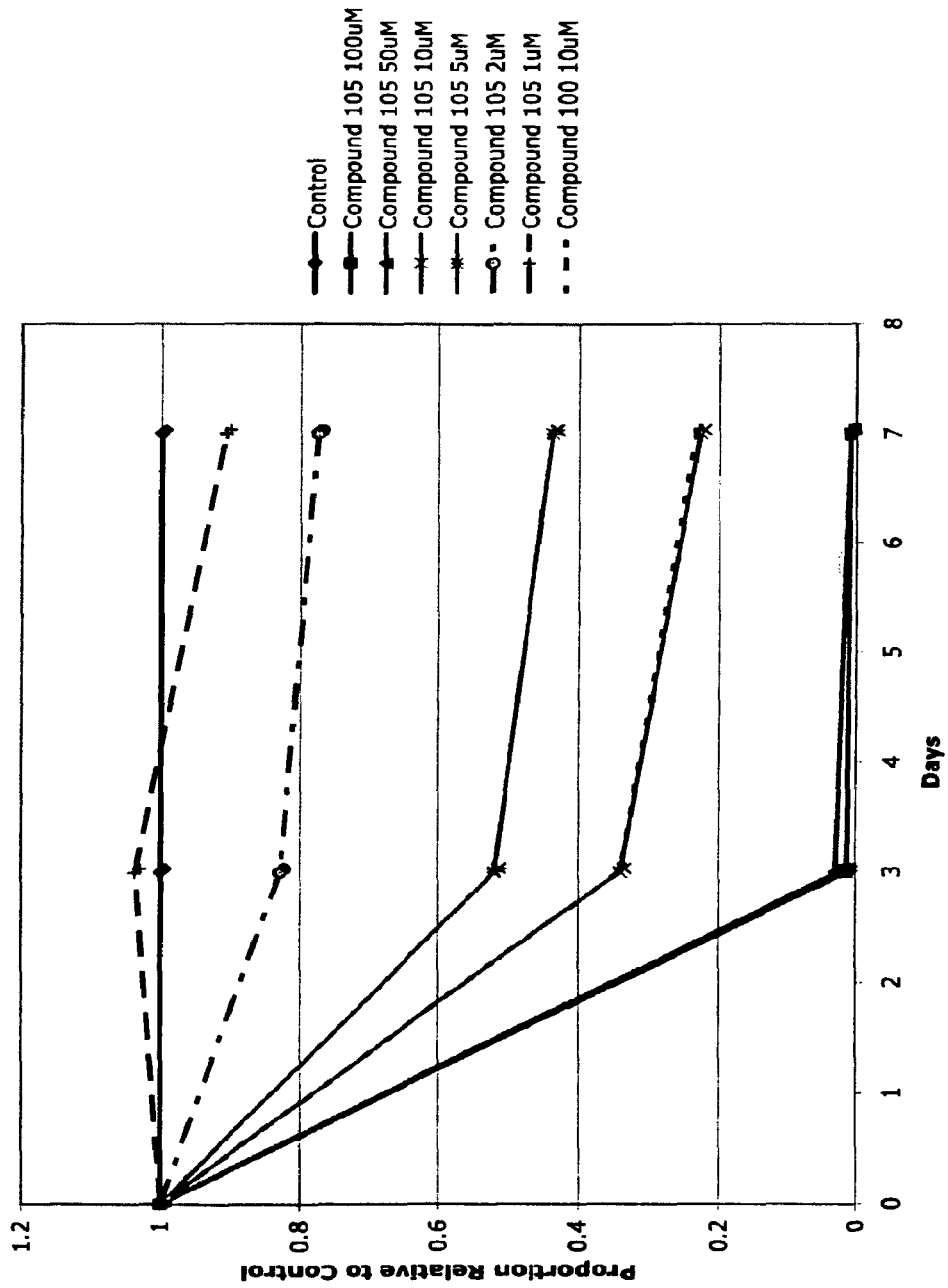
FIG. 8: Inhibition of growth of human GBM cell line U373 treated with Compound 105 for seven days. Graph shows inhibition of growth over seven days at the following dosages: 1, 2, 5, 10, 50 and 100 μM of compound 105, 10 μM of compound 100, and a control dosage.

In addition, logarithmic curves of gliomal cell line U373 treated with different doses of Compound 105 for three (FIG. 6) and seven days (FIG. 7) indicates that increasing dosages demonstrate a greater inhibition of growth. Further, FIG. 8 is a dose-response curve for compound 105 against the human GBM cell growth over seven days at various concentrations of compound 105. It should be noted that Compound 100 was included at a single concentration of 10 µM and that at this concentration the two compounds have identical inhibitory values.

EXAMPLE 2

Effect of Compound 100 Combined with Retinoic Acid

To identify the effect of combinations of PP2A antiphosphatases and retinoids affecting nuclear complexes, we focused on water soluble cantharidin derivatives that have been shown to be active against human GBMs in vitro, endothal and Compound 100.

To observe the effects Compound 100 in combination with retinoic acids, Compound 100 was combined with all-trans retinoic acid. Cells were plated in triplicate on day one with and without different amounts of each drug dissolved in media (Compound 100 and endothal). The total number of cells is counted in the triplicate cultures at each dose and in controls after 7 days and the average number of cells and the standard deviation is determined.

The amount of inhibition of GBM cell growth is expressed as the proportion of the number of cells in the experimental dishes compared to the number of cells in control dishes containing only the drug vehicle and culture medium. The average percent of control is plotted and bracketed by one standard deviation calculated from the triplicate measurements.

Results

FIG. 2 shows that Compound 100 as well as Endothal, each in combination with ATRA, synergistically inhibited proliferation of GBM cell line U373. Synergism (potentiation) of the inhibitory activity of two drugs in combination is said to be present when the percent survival in the presence of two drugs is less than the product of the percent survivals of the two drugs used alone at the same doses in the combination. The extent of synergism of Compound 100 and endothal (end) in combination with ATRA is quantified below in Table 3.

TABLE 3

Endothal and Compound 100 +/− ATRA Inhibition of U373 Cells.

| | Percent of Control | |
| --- | --- | --- |
| | Observed | Expected if Additive |
| ATRA 25 uM | 77% | — |
| END 10 uM | 65% | — |
| ATRA 25 uM + END 10 uM | 32% | 50% |
| Compound 100 1 uM | 78% | — |
| ATRA 25 uM + Compound 100 1 uM | 53% | 60% |

The expected percent survival of U373 cells exposed to the combination of ATRA and Compound 1 was 60% (77% by ATRA×78% by Compound 100=60%), whereas the observed survival was 53%. The expected percent survival in the presence of the combination of ATRA and End was 50% (77% by ATRA×65% by End=50%) whereas the observed survival was 32%.

Compound 100, when combined with Trichostatin A or when combined with 13-cis retinoic acid synergistically inhibited the growth of GBM cell line U373 as shown below in Table 4.

TABLE 4

Compound 100 +/− 13-cis Retinoic Acid (CIS-RA) and Compound 1 +/− Trichostatin A (TSA) Inhibition of GBM Cell Line U373

| | Percent of Control | |
| --- | --- | --- |
| | Observed | Expected If Additive |
| Cis-RA 50 µM | 93.3 +/− 2.2 | |
| TSA 0.033 µM (0.01 µg/ml) | 71.6 +/− 0.4 | |
| Compound 100 - 1 µM | 97.9 +/− 1.0 | |
| Compound 100 - 5 µM | 52.5 +/− 2.9 | |
| Cis-RA 50 µM + Compound 100 - 1 µM | 79.3 +/− 3.2 | 91.3 |
| Cis-RA 50 µM + Compound 100 - 5 µM | 31.6 +/− 2.0 | 49.0 |
| TSA 0.033 µM + Compound 100 - 1 µM | 65.7 +/− 2.0 | 70.1 |
| TSA 0.033 µM + Compound 100 - 5 µM | 13.9 +/− 1.0 | 37.6 |

The two drugs were synergistic in their inhibition of the growth of U373 cells. The percent survival of the cells after exposure to two drugs in combination was less than would be expected from the percent survival of the cells when exposed to each of the two drugs at the same doses used in the combination.

EXAMPLE 3

Determination of Tumor Type Specificity

To determine whether there is tumor type specificity of the inhibitory properties of analogues of Compound 100, retinoic acid and Trichostatin A, we measured their inhibitory effects as single agents against the GBM line U373, a breast cancer line, MCF-7 (obtained from ATCC) and a kidney cancer cell line, UMRC (UMRC obtained by Dr. Zhuang, NINDS, NIH from the Intramural Research Support Program, SAIC, National Cancer Institute, Frederick Cancer Research and Development Center).

Results:

The kidney cancer cell line, UMRC (FIG. 3) was less sensitive than the brain tumor line, U373 (FIG. 4) whereas the breast cancer line, MCF-7 (FIG. 5) was as sensitive as U373 to all-trans retinoic acid, endothal thioanhydride, norcantharidin, endothal, and Trichostatin A. There is some cell type specificity of these drugs for GBMs. The activity of the drugs against MCF-7 cells indicates that regimens being developed for brain tumor treatment may also be useful against breast cancer as well as other tumors that overexpress N-CoR.

EXAMPLE 4

Figure 9:
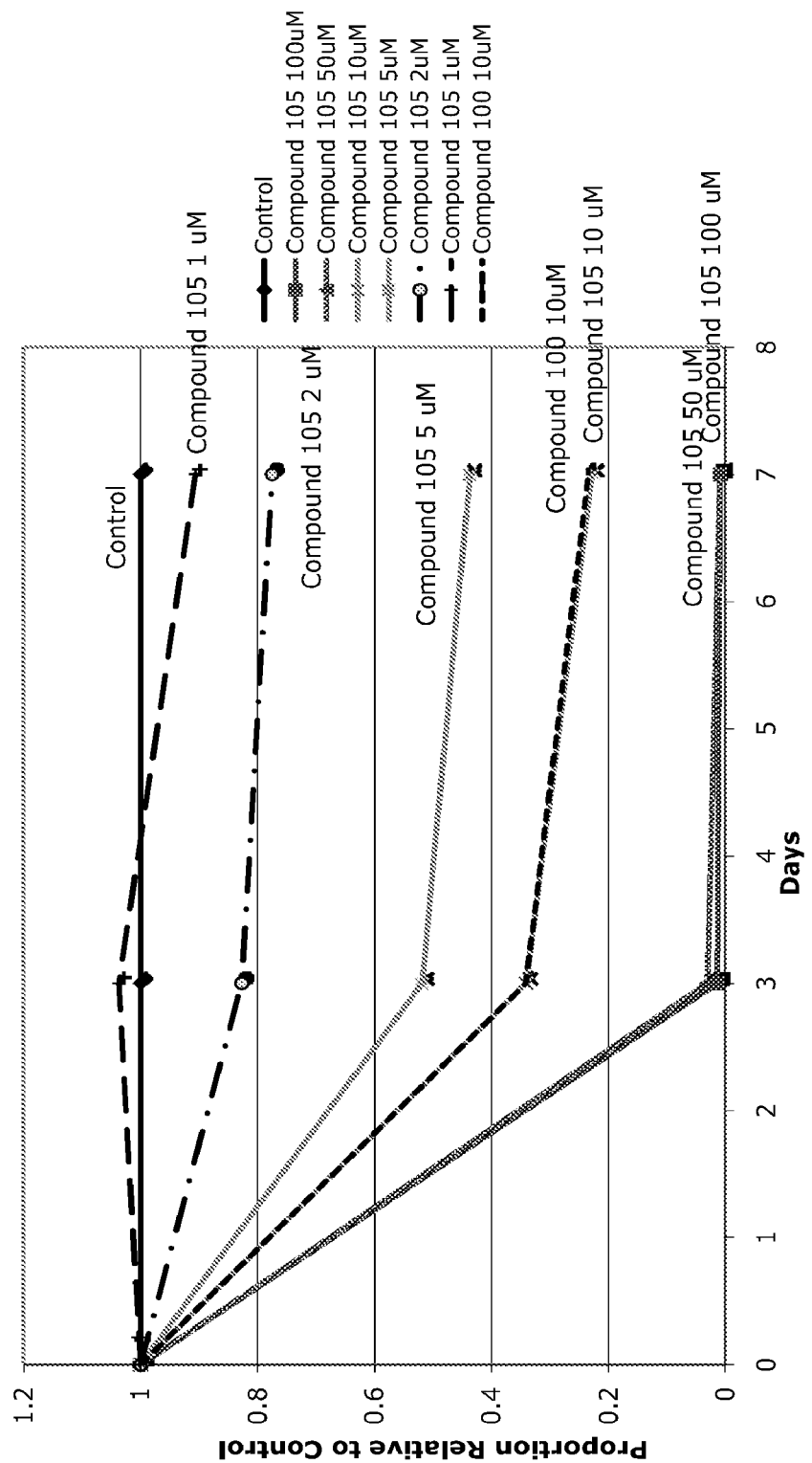
FIG. 9: Inhibition of growth of gliomal cell line U373 by Compound 105 over 7 days.

In addition to the inhibitory activities at low micromolar concentrations of compound 100, compound 105, like compound 100, is also a zwitterion, and is highly active as shown in FIG. 9.

Figure 10:
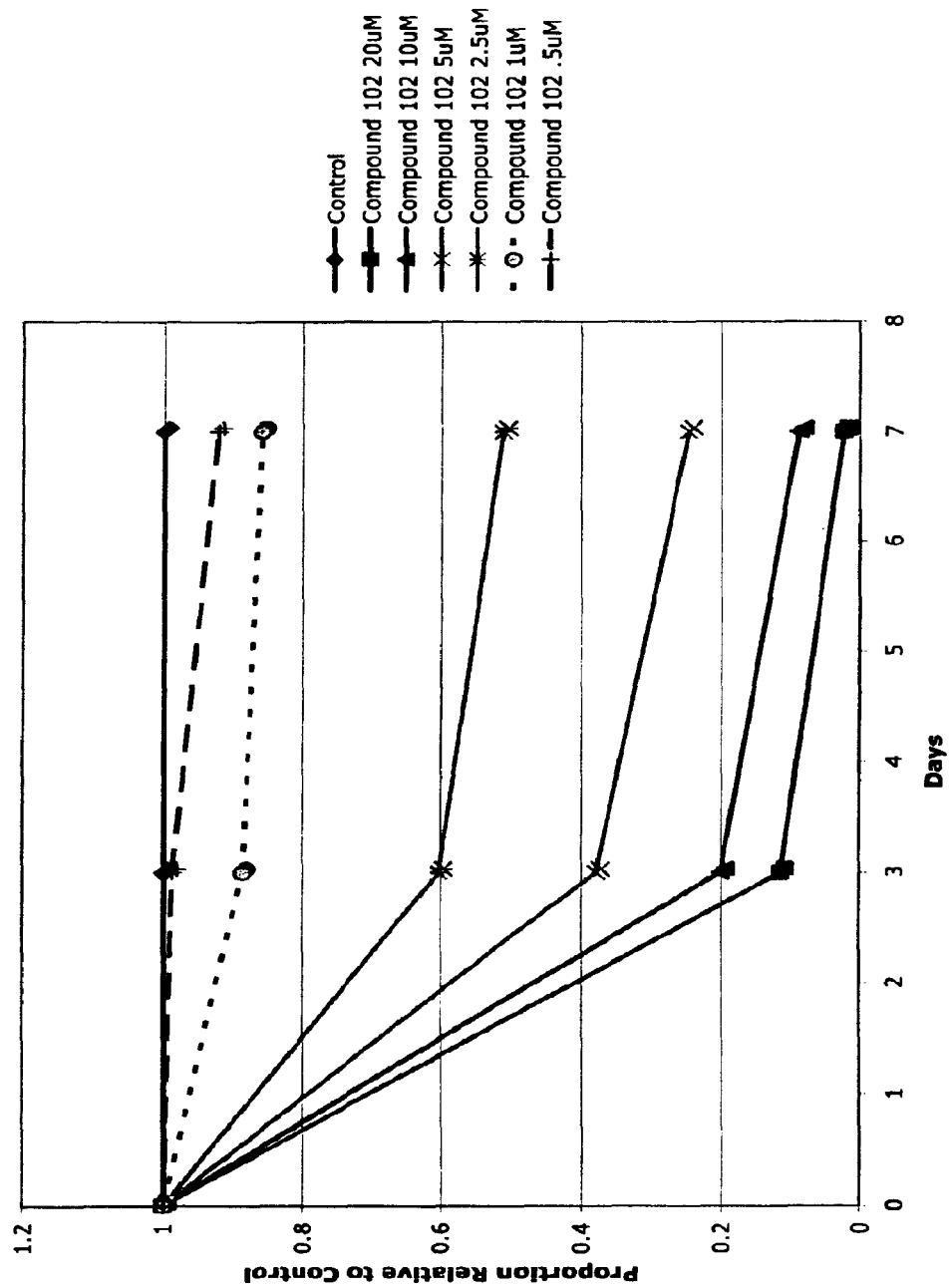
FIG. 10: Inhibition of growth of gliomal cell line U373 by Compound 102 over 7 days.
Figure 11:
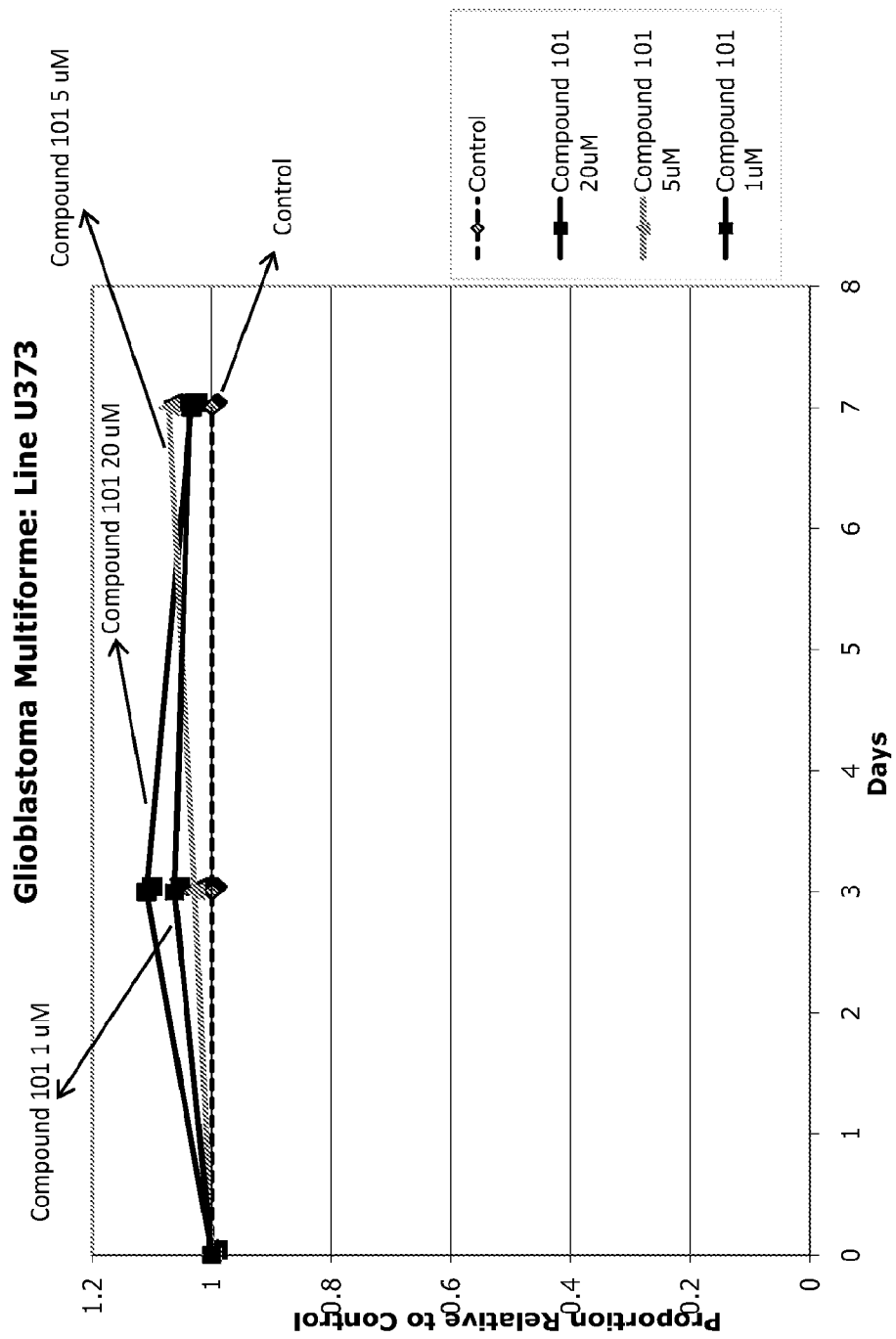
FIG. 11: Inhibition of growth of gliomal cell line U373 by Compound 101 over 7 days.
Figure 12:
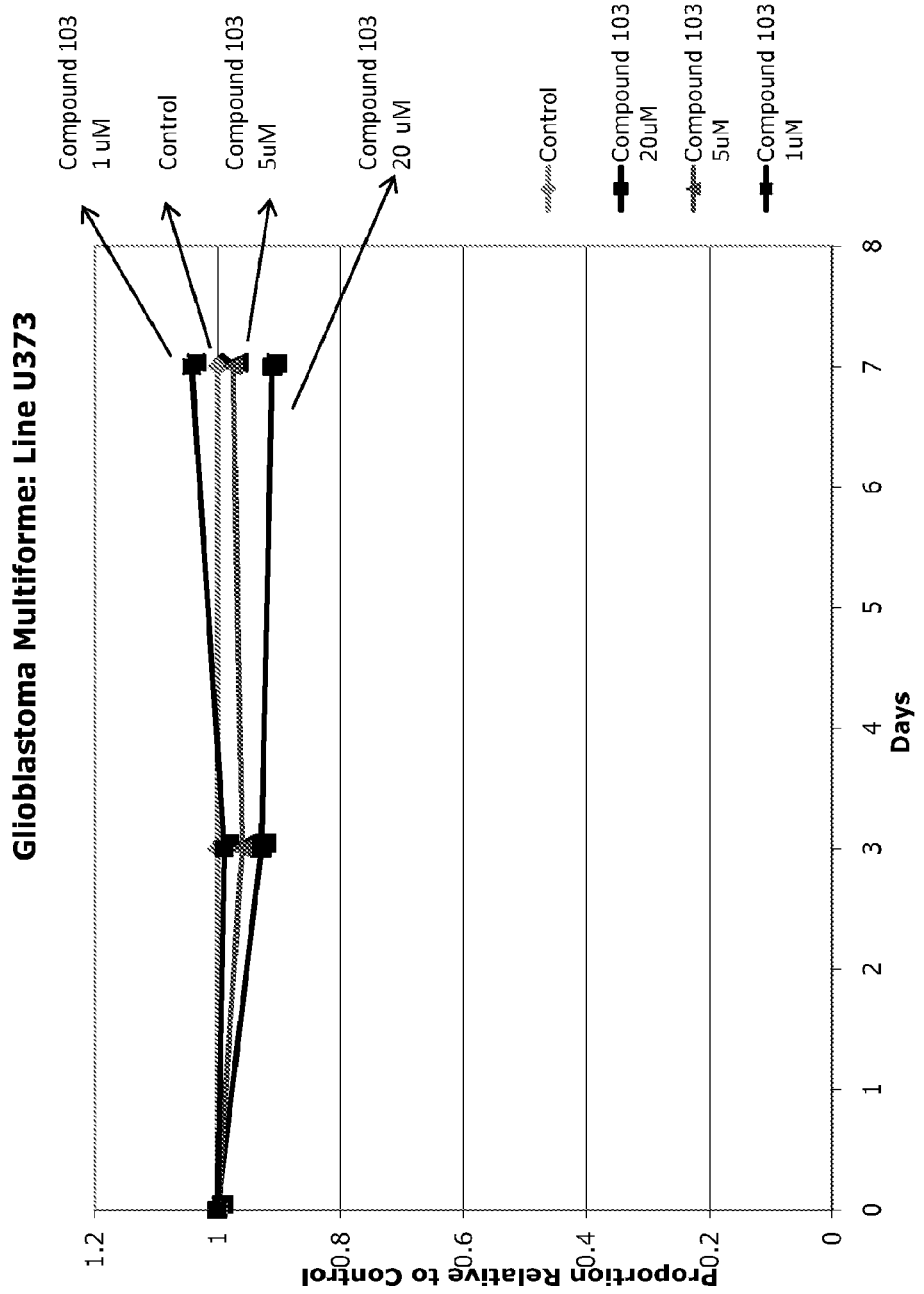
FIG. 12: Inhibition of growth of gliomal cell line U373 by Compound 103 over 7 days.
Figure 13:
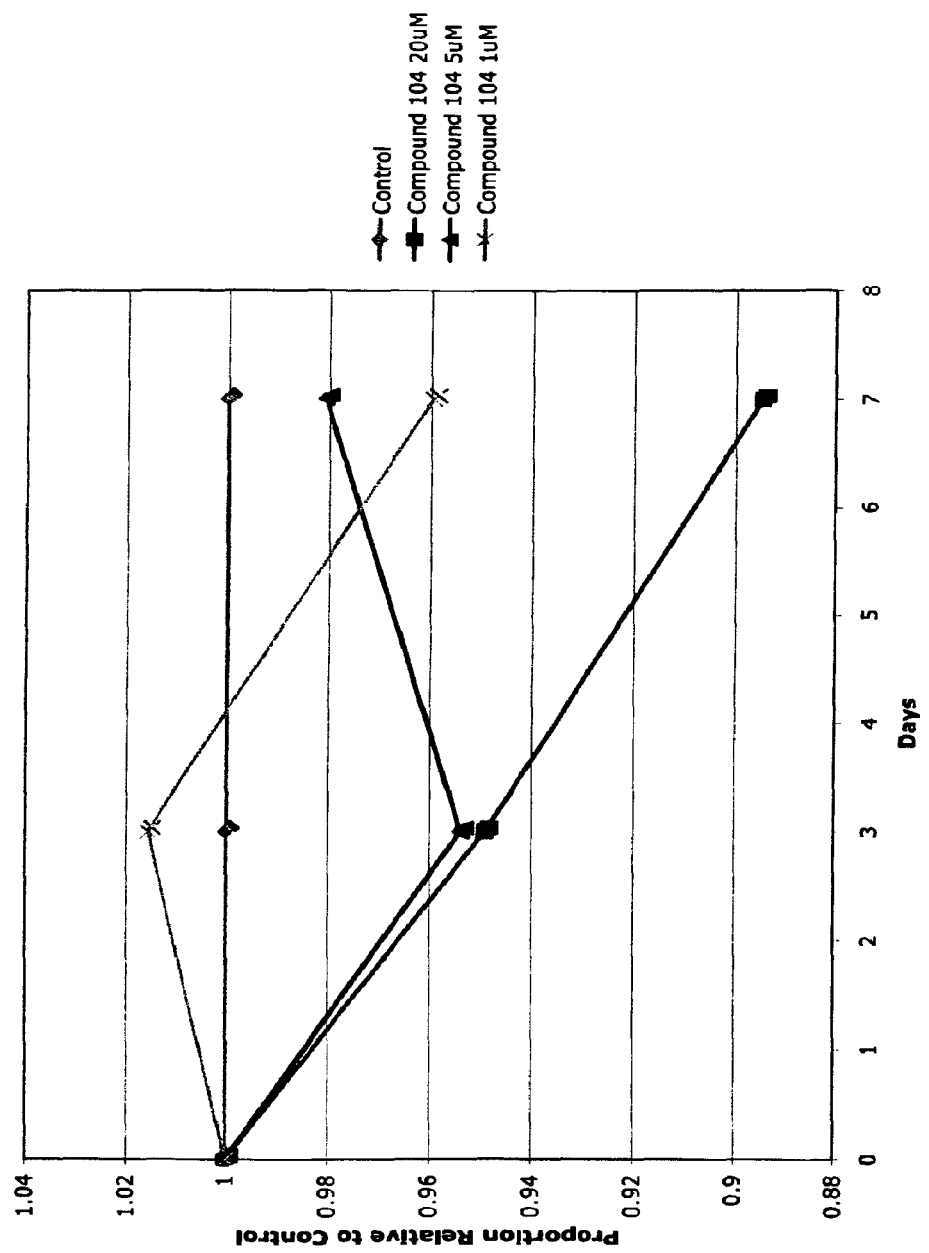
FIG. 13: Inhibition of growth of gliomal cell line U373 by Compound 104 over 7 days.
Figure 14:
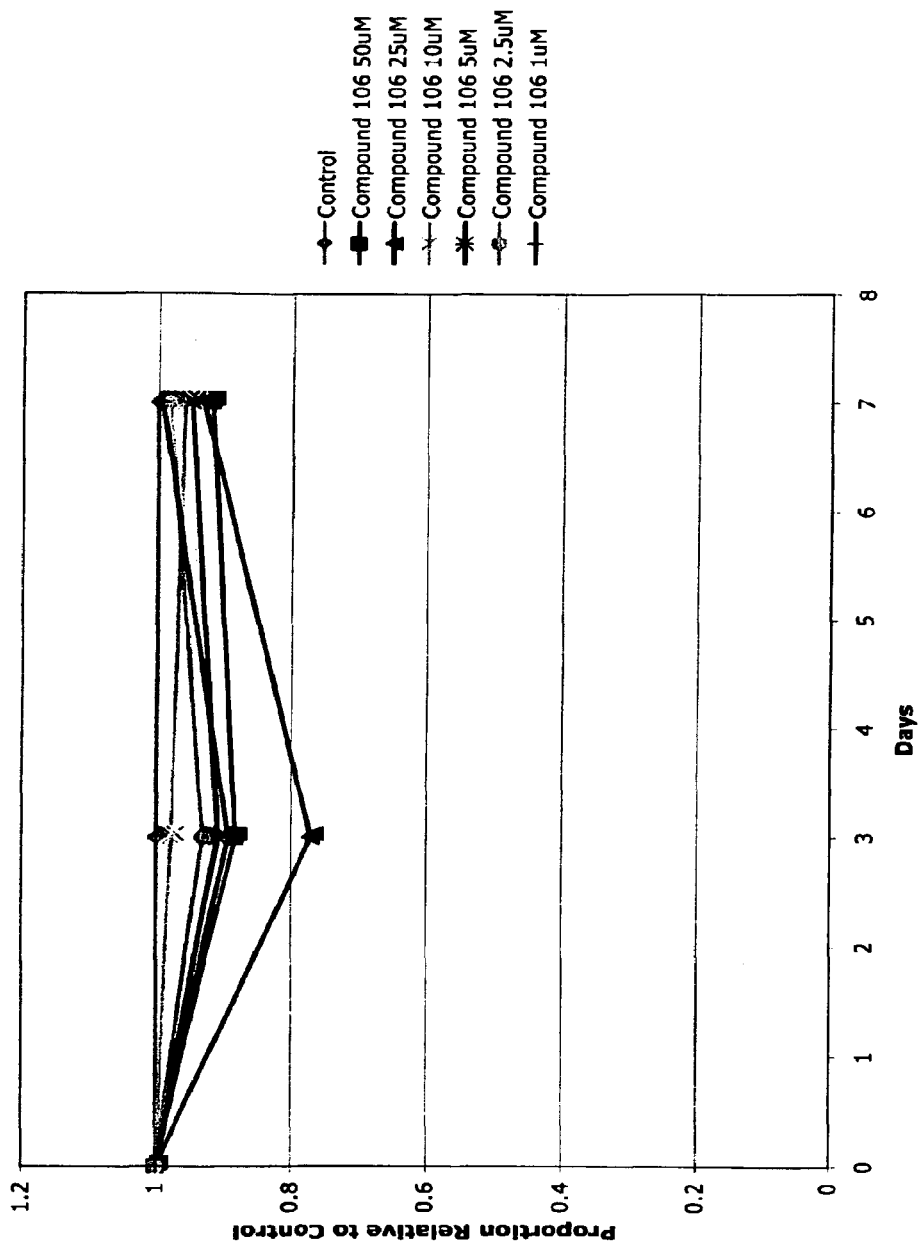
FIG. 14: Inhibition of growth of gliomal cell line U373 by Compound 106 over 7 days.

The lipid soluble compound 102 is also highly potent in inhibiting glioma cell line, U373 (FIG. 10). Other derivatives of nocantharidin, compounds 101, 103, 104 and 106 have less activity (FIGS. 11-14).

For all cell culture experiments, cells are allowed to grow in the presence or absence of different concentrations of drug or in the presence of the vehicle used to dissolve the drug, PBS for compound 100 and DMSO for compound 102. Cell counts are done in triplicate on day 3 and day 7 and inhibition of growth is expressed as a percentage of the number of cells present in the experimental well divided by the number of cells in a control well.

Figure 15:
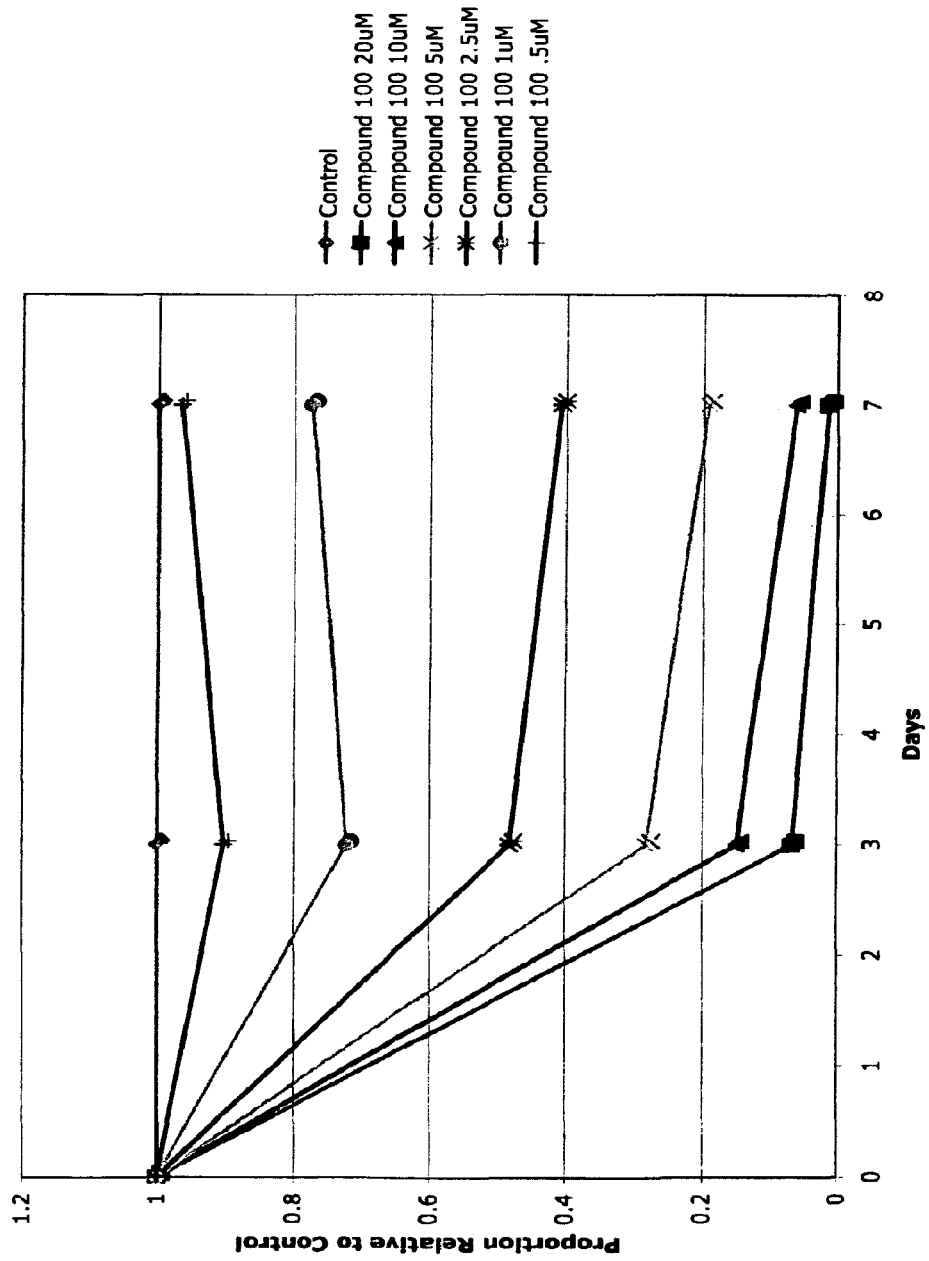
FIG. 15: Inhibition of growth of gliomal cell line U373 by Compound 100 over 7 days.
Figure 16:
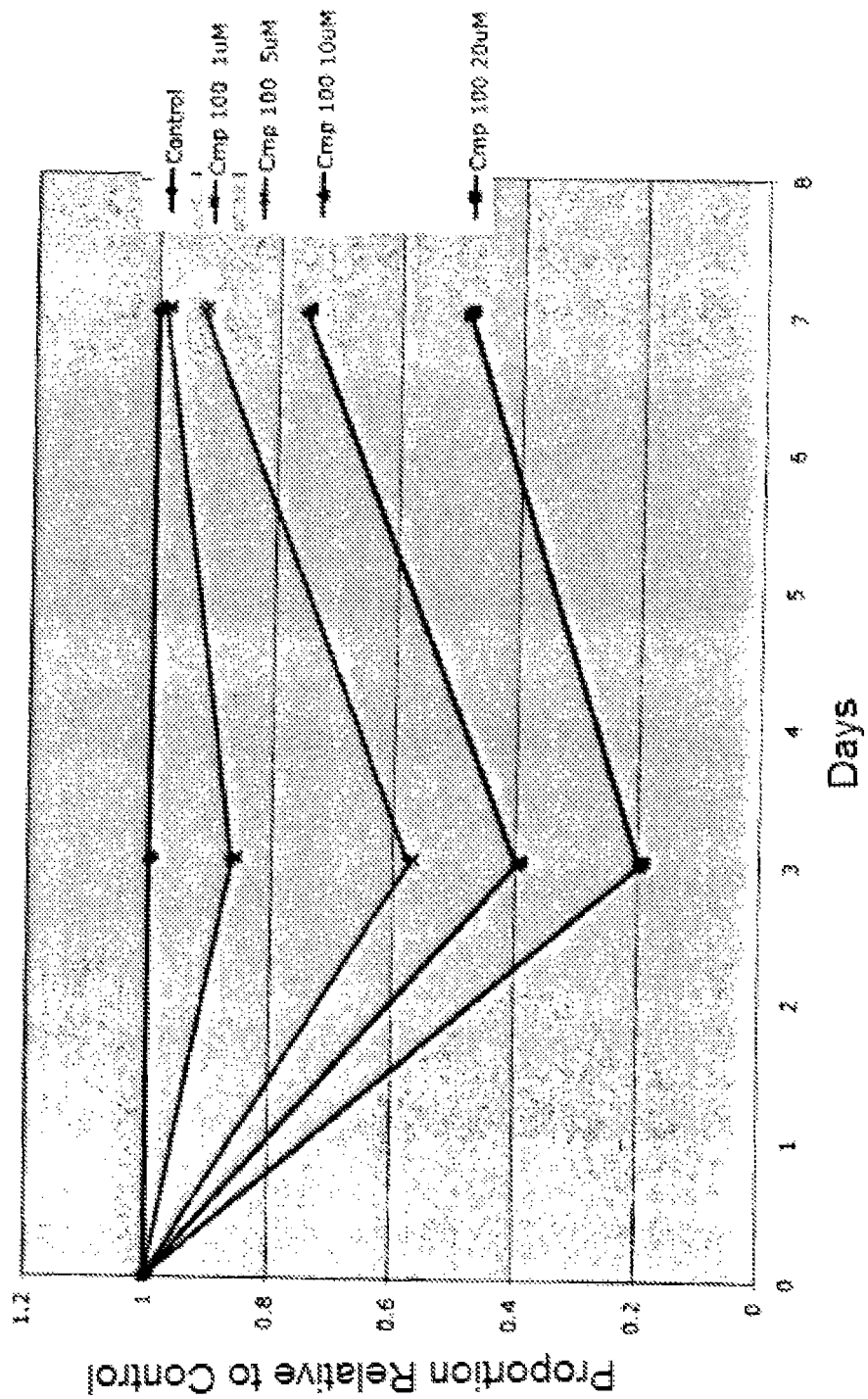
FIG. 16: Inhibition of growth of medulloblastoma cell line DAOY by compound 100 over 7 days.

There is dose dependent inhibition by compound 100 of the GBM cell line U373 (FIG. 15) and dose dependent inhibition of the medulloblastoma cell line DAOY (FIG. 16).

For in vivo experiments, subcutaneously implanted tumor cells are allowed to grow over 7 days to a size of 5-7 mm. On day 7, drug administration is begun ip daily for 20 days. The maximum perpendicular diameters of the tumor masses are measured every 2 to 5 days. On the $21^{st}$ day after initiation of treatment, the animals are sacrificed and dissected free of the subcutaneous tissues and measured.

Figure 17:
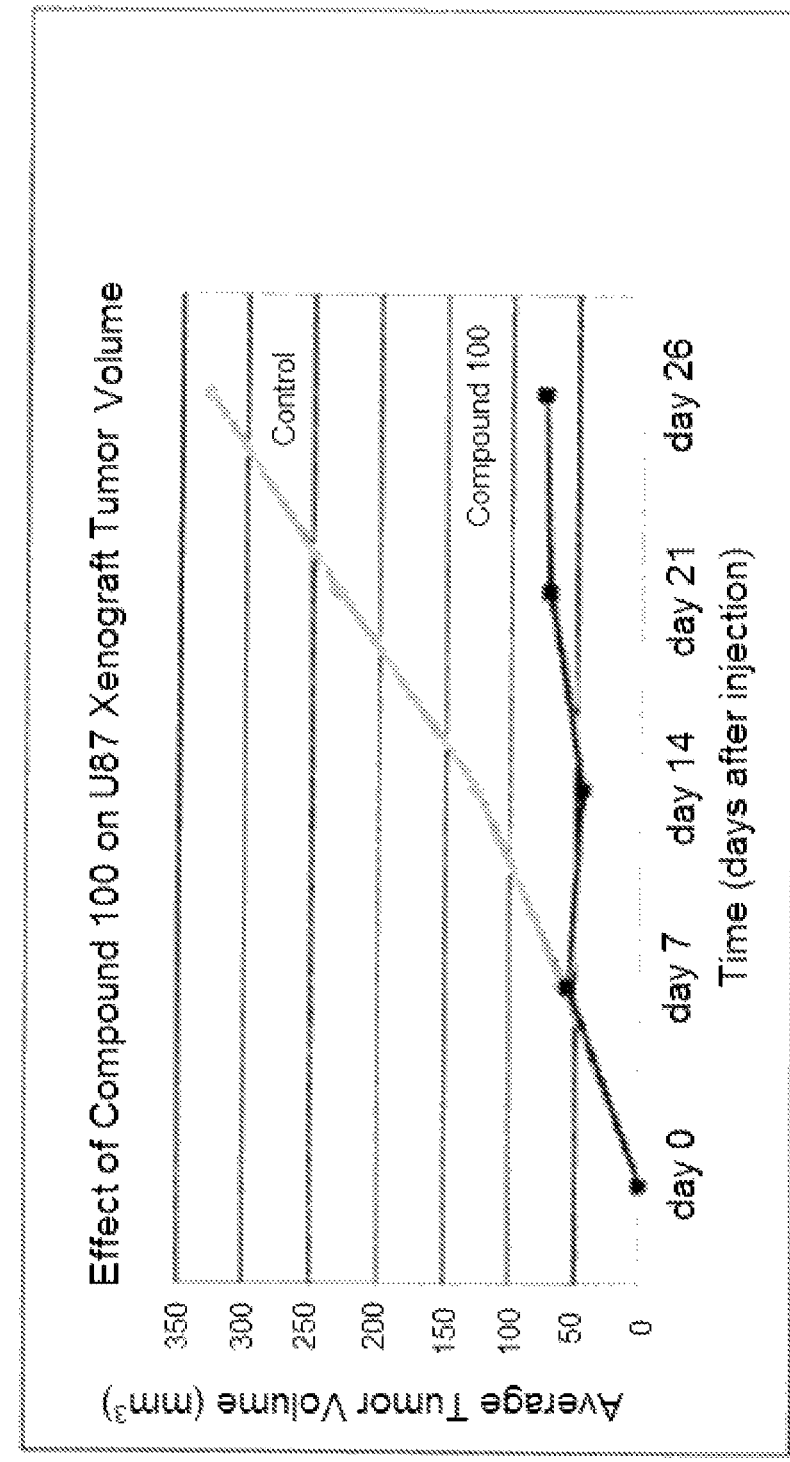
FIG. 17: Effect of compound 100 on U87 xenograft tumor volume over 26 days.
Figure 18:
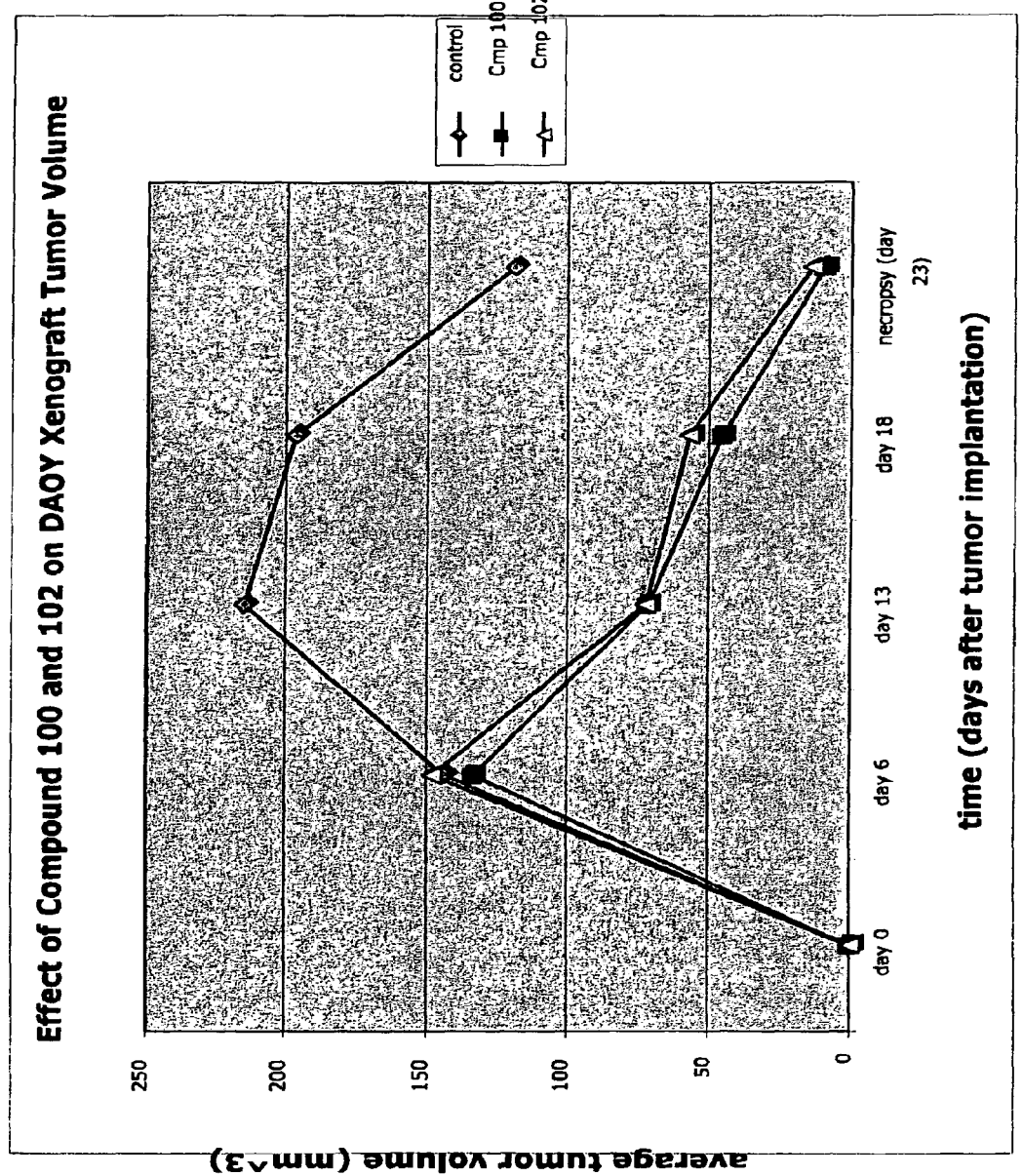
FIG. 18: Effect of compound 100 and compound 102 on DAOY xenograft tumor volume over 23 days.

It is shown the compound 100 supresses the growth of the GBM cell line U87 growing subcutaneously in SCID mice (FIG. 17). It is also demonstrated the compound 100 and compound 102 both inhibit the proliferation of DAOY cells when implanted subcutaneously in SCID mice (FIG. 18).

EXAMPLE 5

Drug Activity Against Human Cancer Cell Lines Other than Glioblastomas and Medulloblastomas Materials and Methods MDA-MB-231, HT-29, NCI-H460, NCI-H522, NCI-H69, GXF-209, HepG2, OVAR-3, PANC-1, DU-145, LNCAP, HL-60, K-562, and MOLT-4 cell lines were either obtained from the American Type Culture Collection (ATCC; Manassas, Va.), or from the National Cancer Institute (NCI; Frederick, Md.). RPMI-1640 media, L-glutamine dipeptide (HyQ SG-200), and HEPES were obtained from Hyclone (Logan, Utah).

Fetal bovine serum (FBS) was obtained from Sigma-Aldrich, (St. Louis, Mo.). DMSO was purchases from Fisher Chemicals (Fair Lawn, N.J.). The CellTiter-Glo Luminescent Cell Viability Assay reagent was obtained from Promega Corporation (Madison, Wis.). All tissue culture plasticware was obtained from Corning Incorporated (New York, N.Y.). Compound 100 and Compound 102 were provided by Lixte Biotechnology Holdings, Inc. (East Setauket, N.Y.).

All cell lines were routinely cultured twice weekly in RPMI-1640 medium supplemented with 2 mM L-glutamine dipeptide, 10 mM HEPES, and 10% FBS.

The adherent cell lines MDA-MB-231, HT-29, NCI-H460, NCI-H522, GXF-209, HepG2, OVAR-3, PANC-1, DU-145, and LNCAP cells were each seeded into two 96-well plates at 2,500 cells per well in a total volume of 50 uL and incubated in a 37° C. humidified 5% $CO_2$ cell culture incubator overnight. The suspension cell lines NCI-H69, HL-60, K-562, and MOLT-4 were each seeded into two 96-well plates at 10,000 cell per well in a total volume of 50 uL and incubated in a 37° C. humidified 5% $CO_2$ incubator overnight.

A 20 mM stock of water soluble drug Compound 100 was made in sterile water, and 20 mM stocks of Compound 102 were made in DMSO. This was followed by making 2× stocks of the final concentrations required in RPMI-1640 medium. 50 uL of the 2× stock solutions were added to the appropriate wells, which contained 50 uL of cells and medium to give the final concentrations outlined in the Appendix. The top concentration of Compound 100 was filter sterilized before use. 50 uL of media were added to media and cell control wells and 50 uL of a mock 2× DMSO stock solution were added to vehicle control wells. At the same time that the drugs were added to the cells, one of the plates from each cell line was used for the CellTiter-Glo assay as described below in order to obtain Day 0 values for each cell Line. Following a 72 hr incubation period, the CellTiter-Glo assay was performed on the remaining plate.

CellTiter-Glo Assay

The assay was performed as per the manufacturer's instructions.

Briefly, plates were removed from the incubator and placed on the bench at room temperatures for 30 minutes. Plates were not stacked. Following the 30 min incubation at room temperature, 100 uL of CellTiter-Glo reagent were added to each well on the plate and mixed for 2 minutes, followed by further 10 minute incubation at room temperature. Luminescence was then recorded using the PerkinElmer Microbeta scintillation and luminescence counter (Trilux).

Results and Discussion

These studies were performed as described in Materials and Methods, with the raw data and plate set-up outlined in the Appendix. The IC50 values obtained for each drug in each cell line are outlined in Table 5. The graphical representation of the effect of the compounds on each cell line, along with the associated curve fits, is illustrated in FIGS. 19A-N.

The majority of cell lines tested were sensitive to all drugs in the low uM range (Table 5). Both Compound 100 and Compound 102 have significant activity (approximately equal for all lines to the positive comparator clinically used anti-cancer drug, doxorubicin). The drugs were active against cell lines of: breast cancer; colon cancer; the three major types of lung cancer, large cell, adenocarcinoma and small cell; stomach cancer; liver cancer (hepatoma); ovary adenocarcinoma; pancreas carcinoma, two types of prostate carcinoma; and three types of leukemia, promylocytic, chronic myelocytic, and acute lymphocytic (Table 5).

TABLE 5

Figure 19B:
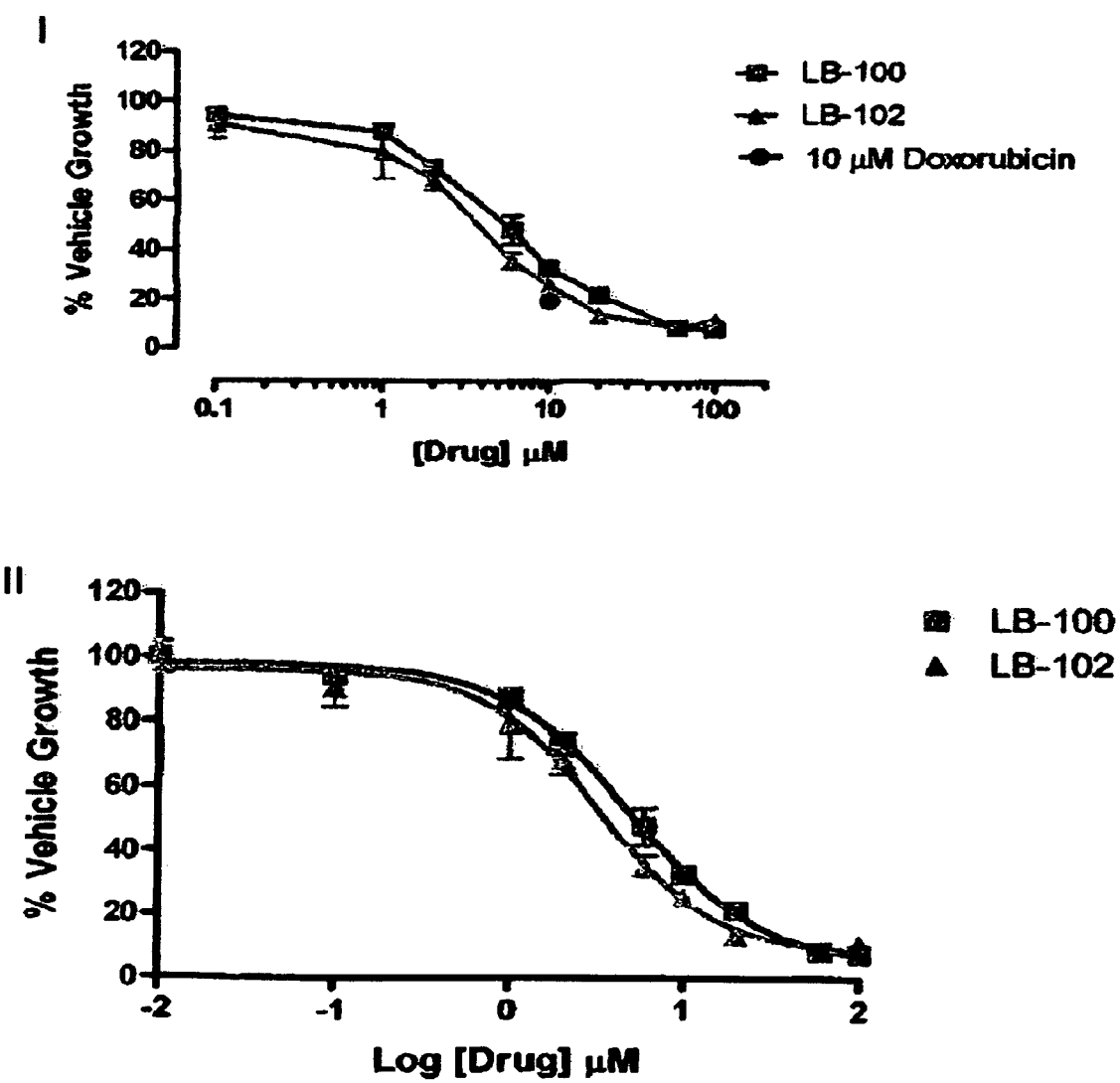
FIG. 19B: Graphical representation (I) and curve fit with $IC_{50}$ value (II) of data obtained following exposure of HT-29 cells to compound 100 and compound 102 using the CellTiter-Glo assay. The effects of 10 μM doxorubicin that was used as a positive control are also shown in I. Each point represents the mean±SD of at least triplicate samples.
Figure 19J:
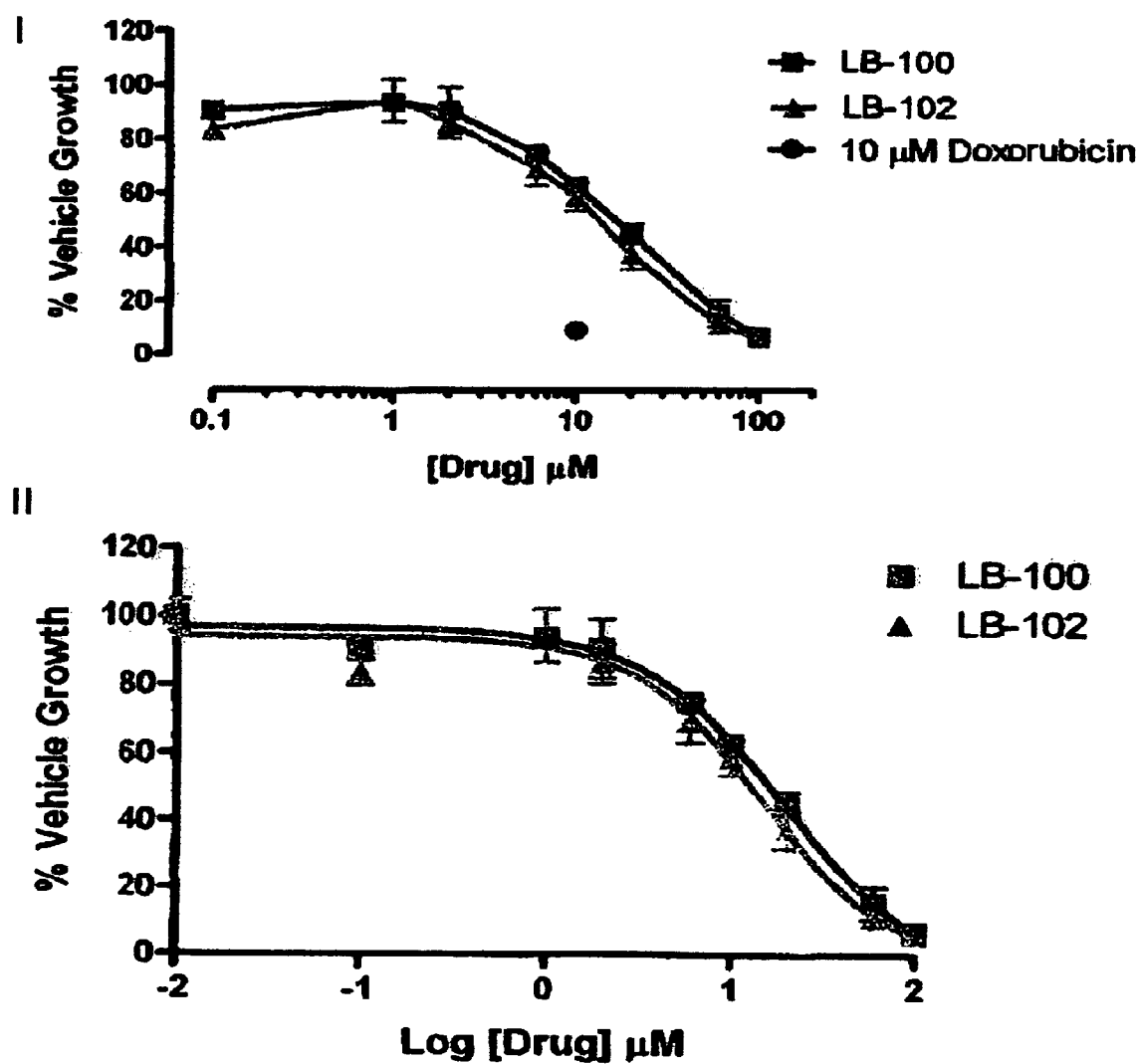
FIG. 19J Graphical representation (I) and curve fit with $IC_{50}$ value (II) of data obtained following exposure of DU-145 cells to compound 100 and compound 102 using the CellTiter-Glo assay. The effects of 10 μM doxorubicin that was used as a positive control are also shown in I. Each point represents the mean±SD of at least triplicate samples.
Figure 19L:
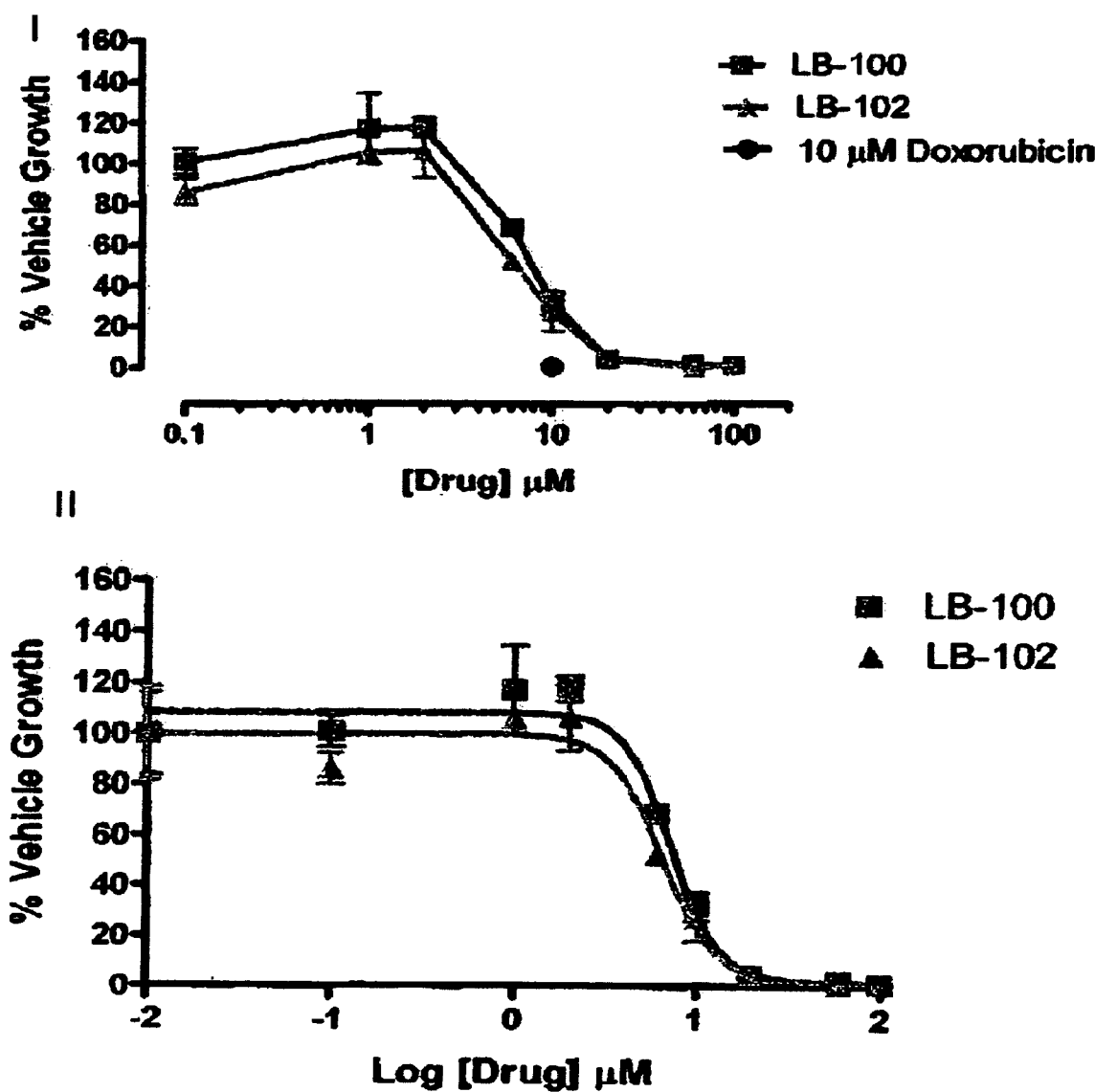
FIG. 19L: Graphical representation (I) and curve fit with $IC_{50}$ value (II) of data obtained following exposure of HL-60 cells to compound 100 and compound 102 using the CellTiter-Glo assay. The effects of 10 μM doxorubicin that was used as a positive control are also shown in I. Each point represents the mean±SD of at least triplicate samples.
Figure 19M:
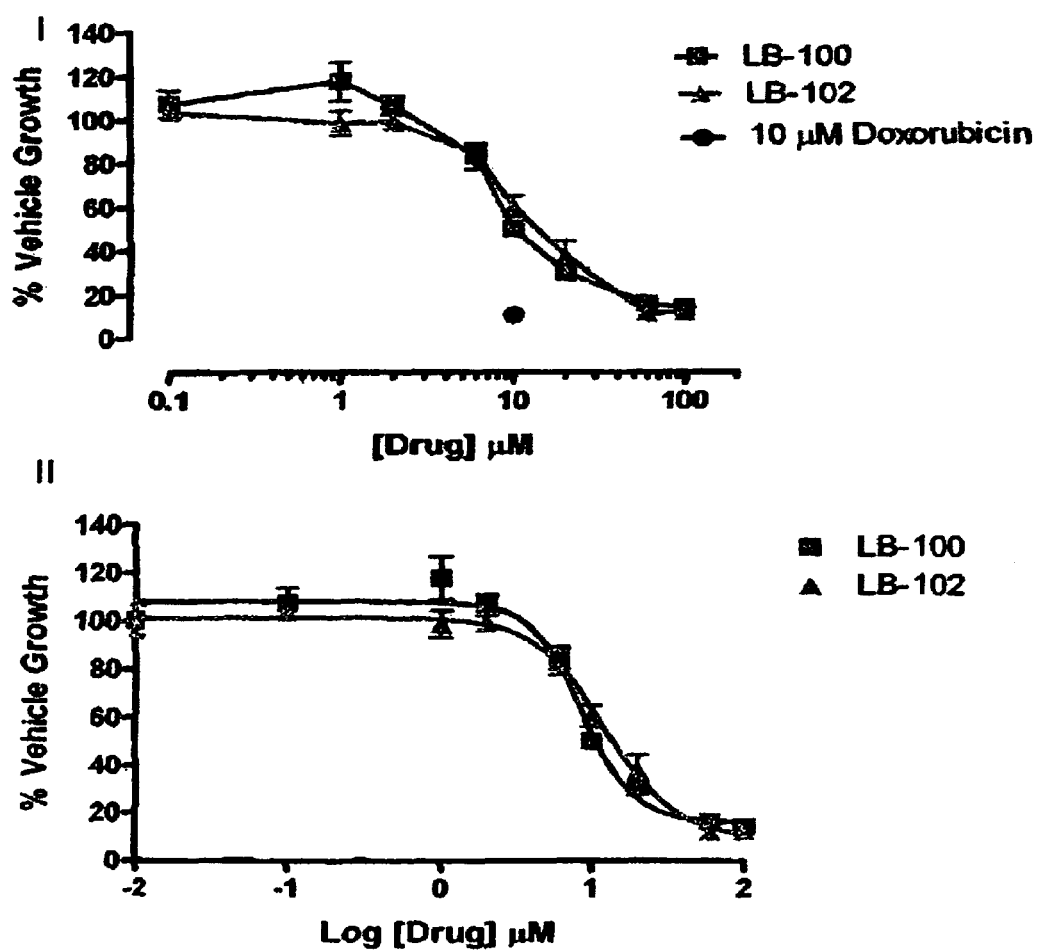
FIG. 19M: Graphical representation (I) and curve fit with $IC_{50}$ value (II) of data obtained following exposure of K-562 cells to compound 100 and compound 102 using the CellTiter-Glo assay. The effects of 10 μM doxorubicin that was used as a positive control are also shown in I. Each point represents the mean±SD of at least triplicate samples.
Figure 19N:
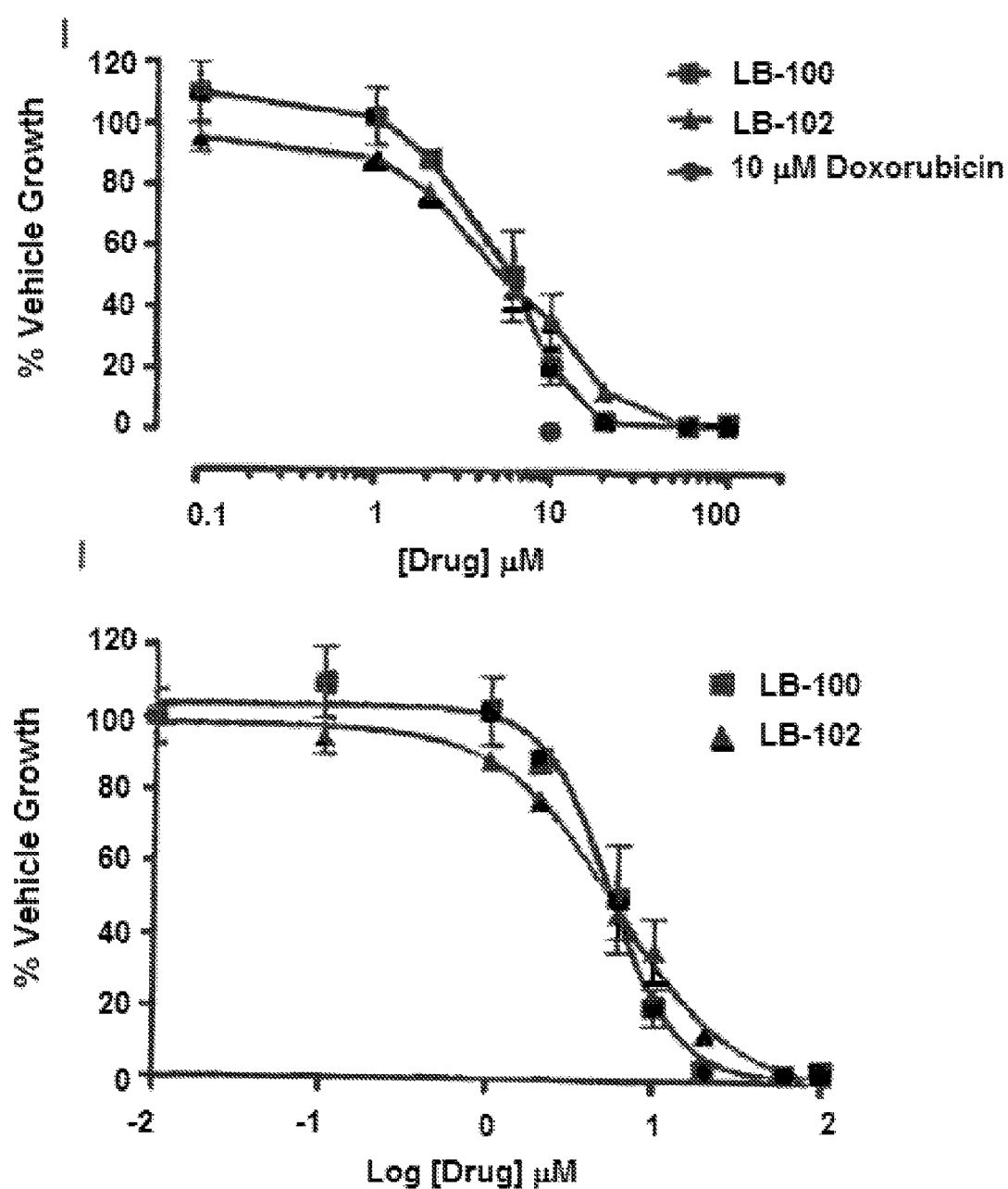
FIG. 19N: Graphical representation (I) and curve fit with $IC_{50}$ value (II) of data obtained following exposure of MOLT-4 cells to compound 100 and compound 102 using the CellTiter-Glo assay. The effects of 10 μM doxorubicin that was used as a positive control are also shown in I. Each point represents the mean±SD of at least triplicate samples.

The Concentration of Compound 100 and 102 that Results in 50% Inhibition of Proliferation (IC50) Obtained from the Curve Fits of Fourteen Human Cancer Cell Lines (FIGS. 19A-N)

| Cell Line | $IC_{50}$ μM | |
| --- | --- | --- |
| Cancer Type | Compound-100 | Compound-102 |
| MDA-MB-231 Breast | 9.5 | 6.6 |
| HT-29 Colon | 5.3 | 3.6 |
| NCI-H460- Lung: large cell | 24.3 | 17.5 |
| NCI-H522 Lung adenoca | 3.4 | 2.2 |
| NCI-H69 Lung small cell | 23.9 | 24.6 |
| GXF-209 Stomach | 7.9 | 5.3 |
| HepG2 Liver | 31.6 | 22.1 |
| OVCAR-3 Ovary adenoca | 2.9 | 5.1 |
| PANC-1 Pancreas | 25.1 | 20.7 |
| DU-145 | 16.4 | 13.0 |

TABLE 5-continued

The Concentration of Compound 100 and 102 that Results in
50% Inhibition of Proliferation (IC50) Obtained from the Curve
Fits of Fourteen Human Cancer Cell Lines (FIGS. 19A-N)

| Cell Line | IC$_{50}$ µM | |
|---|---|---|
| Cancer Type | Compound-100 | Compound-102 |
| Prostate LNCAP | 1.5 | 0.48 |
| Prostate HL-60 | 7.7 | 6.5 |
| Leukemia promyelocytic K-562 | 10.7 | 13.7 |
| Leukemia chronic myelo MOLT-4 | 5.7 | 5.6 |
| acute lympho | | |

EXAMPLE 6

Antifungal Activity

The growing population of immunocompromised patients due to transplantation, HIV/AIDS and cancer, primarily leukemia, has resulted in an increase in severe fungal infections. The fungi most often recovered from infections in these patients are *Aspergillus* spp. and *Candida* spp. Effective therapies are available for the treatment of *Candida* spp. but there remains a concern about the treatment of infections caused by *Aspergillus* spp., which are associated with high mortality in the immunocompromised host. Such infections are difficult to clear in this group of patients thus increasing the need for agents with good activity against these fungi. In addition, less serious but chronic troublesome fungal infections of the nails and skin of the feet and hands, the dermatophytoses, affect millions of people worldwide. As a result of the changing scene of fungal infections and the lack of an overall cure for these infections, Compounds 100 and 102 are undergoing testing for possible future development.

Materials and Methods

Anti-fungal testing was completed with a common lot for compounds 100 and 102.

A 10 mg portion of each powder was weighed out and added to 1 ml of sterile distilled water for compound 100 and DMSO for compound 102. The resulting concentration of 10 µg/ml was diluted to a working concentration of 640 µg/ml for each compound. All subsequent dilutions were also made using the respective diluents. Final testing concentrations ranged from 0.125-64 µg/ml.

Results

A total of 23 isolates were tested to include 3 *Candida albicans*, 3 *Candida glabrata*, 3 *Cryptococcus neoformans*, 3 *Aspergillus fumigatus*, 3 *Rhizopus oryzae*, 3, *Fusarium solani*, 3 *Pseudallescheria boydii*, and 2 *Trichosporon rubrum*. All isolates were clinical isolates submitted to the Fungus Testing Laboratory for evaluation. Antifungal susceptibility testing was accomplished according to the methods outlined in the National Committee for Clinical Laboratory Standards, M-27A2, Reference Method for Broth Dilution Antifungal Susceptibility Testing of Yeasts; Approved Standard, and M38-A "Reference Method for Broth Dilution Antifungal Susceptibility Testing of Conidium-Forming Filamentous Fungi; Approved Standard". This includes testing in RPMI-1640 with glutamine and without bicarbonate, an inoculum size of 0.5-2.5×10$^3$ for yeasts or 1-5×10$^4$ for moulds, and incubation at 35° C. for 24 and 48 hours. The minimum inhibitory concentration (MIC) was defined as the lowest concentration that resulted in an 50% reduction in turbidity as compared to a drug-free control tube for the yeast and 80% inhibition for the moulds.

While no activity was noted for compound 100 at the levels tested, significant activity was found for compound 102 against *T. rubrum* (Table 6).

CONCLUSION

Depending on achievable levels of this compound in human subjects, safety profiles and other pertinent factors, this compound may be a viable contender for dermatophytic infections caused by *Trichosporon rubrum*.

TABLE 6

| | | Compound 100/24 Hours | Compound 100/48 Hours | Compound 102/24 Hours | Compound 102/48 Hours |
|---|---|---|---|---|---|
| CP | Control | | | | |
| 07-3006 | C. albicans | >64 | >64 | >64 | >64 |
| 07-3011 | C. albicans | >64 | >64 | >64 | >64 |
| 07-3012 | C. albicans | >64 | >64 | >64 | >64 |
| 07-2964 | C. glabrata | >64 | >64 | >64 | >64 |
| 07-2965 | C. glabrata | >64 | >64 | >64 | >64 |
| 07-3013 | C. glabrata | >64 | >64 | >64 | >64 |
| 07-2665 | C. neoformans | >64 | >64 | >64 | >64 |
| 07-2737 | C. neoformans | >64 | >64 | >64 | >64 |
| 07-2829 | C. neoformans | >64 | >64 | >64 | >64 |
| 07-1870 | R. arrhizus | >64 | >64 | >64 | >64 |
| 07-2044 | R. arrhizus | >64 | >64 | >64 | >64 |
| 07-2078 | R. arrhizus | >64 | >64 | >64 | >64 |
| 07-1399 | F. solani | >64 | >64 | >64 | >64 |
| 07-1755 | F. solani | >64 | >64 | >64 | >64 |
| 07-1867 | F. solani | >64 | >64 | >64 | >64 |
| 07-1333 | P. boydii | >64 | >64 | >64 | >64 |
| 07-1502 | P. boydii | >64 | >64 | >64 | >64 |
| 07-1601 | P. boydii | >64 | >64 | >64 | >64 |
| 05-388 | A. fumigatus | >64 | >64 | >64 | >64 |
| 06-4126 | A. fumigatus | >64 | >64 | >64 | >64 |
| 07-2039 | A. fumigatus | >64 | >64 | >64 | >64 |
| 07-1743 | T. rubrum | >64 | >64 | 2 | 2 |
| 07-2055 | T. rubrum | >64 | >64 | 2 | 2 |

REFERENCES

Alder, B., (1938) *Ann. Chem.,* 113, 120.
Ayaydin, F. at al., (2000) *The Plant Journal,* 23:85-96.
Baskin, T. and Wilson, J., (1997) *Plant Physiol.* 113:493-502.
Bastien et al. (2004), *Gene,* Vol. 328, pp. 1-16.
Bhongle, N. N. et al., (1984) *Indian J. Chem. Sect. B.,* 23, 465-468.
Blaheta, A et al. (2002), *Current Medicinal Chemistry,* Vol. 9, pp. 1417-1433.
Crafts, A. S., (1953) *Rev. Plant. Physiol.,* 4:253-282.
Drewinko et al. (1967) *Cancer Biochem. Biophys.,* Vol. 1, pp. 187-195.
Erdodi, F. et al., (1985) *Am. J. Physiol.,* 269 (*Cell Physiol.* 38) C1176-C1184.
Essers, M. et al., (2001) *Tetrahedron Lett.,* 42, 5429-5433.
Fanghaemel, F. et al., (1994) *Synthesis,* 10, 1067-1071.
Giannini, R. and Cvallini, A. (2005) *Anticancer Research,* Vol. 36, No. 6B, pp. 4287-4292.
Göttlicher, M et al. (2001) *Eur. Mol. Bio. Journal,* Vol. 20, no. 24, pp. 6969-6978.

Graziano, M. J. and Casida, J. E. (1987) *Toxicol Lett.*, 37, 143-148.
Hart, M E et al. (2004) *Bioorganic & Medicinal Chemistry Letters*, Vol. 14, pp. 1969-1973.
Havrilesky, L J et al. (2001) *J. Soc. Gynecology. Investig.*, Vol. 8, pp. 104-113.
Hermanson et al. (2002) *Nature*, Vol. 419, pp. 934-939.
Honkanan, R. E. et al., (1993) *FEBS Lett.*, 330, 283-286.
Hughes et al. (1988) *Nature*, Vol. 335, pp. 70-73.
Kayser, M. M. et al., (1989) *Can. J. Chem.*, 67, 1401-1410.
Kayser, M. M. et al., (1982) *Can. J. Chem.*, 60, 1199-1208.
Kawamura, N. et al. (1990) *Chem. Res. Toxicol.*, Vol. 3, pp. 318-324.
Kovach, J S et al. (1985) *Cancer Treat. Rep.*, Vol. 69, pp. 97-103.
Li, Y. M. et al., (1992) *Proc. Natl. Acad. Sci. USA*, 89, 11867-11870.
Li, Y. M. et al., (1993) *Biochem. Pharmacol.*, 46, 1435-1443.
Matsuzawa, M. et al. (1987) *J. Agric. Food Chem.*, Col. 35, No. 5.
Momparlet, R L. (1980) *Pharmacol. Ther.*, Vol. 8, pp. 21-35.
Myers, E. et al. (2005) *Clin. Cancer Res.*, Vol. 11, pp. 2111-2122.
Park, D M. et al., (2007) *Cell Cycle*, 6(4): 467-70.
Peng, F. et al. (2002), *J. Cancer Res. Clin. Oncol.*, Vol. 128, pp. 223-230.
Ramezanian, M. et al., (1989) *J. Org. Chem.*, 54, 2852-2854.
Rutka et al. (1988) *Int. J. Cancer*, Vol. 42, pp. 419-427.
Sanderson, L et al. (2004) *Drug Metabolism and Disposition*, Vol. 32, No. 10, pp. 1132-1138.
Sakoff, J A. (2004) *Current Pharmaceutical Design*, Vol. 10, pp. 1139-1159.
Schweizer, H. R., (1989) *Helv. Chin. Acta.*, 2221-2235.
Shimi, I R et al. (1982) *European Journal of Cancer and Clinical Oncology*, 18:785-793.
Singh et al. (2003) *Cancer Research*, Vol. 63, pp. 5821-5828.
Singh et al. (2004*Nature*, Vol. 432, pp. 396-401.
Smith et al., (1994) *Planta* 194:516-524.
Stupp at al. (2005) *N. Engl. J. Med.*, Vol. 352, pp. 987-996.
Trost, L., (1977) *J. Am. Chem Soc.*, 99, 7079.
Tsauer, W. et al., (1997) *Anticancer Research* 17, 2095-2098.
Uchida et al. (2000) *Proc. Nati. Acad. Sci. USA*, Vol. 97, pp. 14720-14725.
Wang, D S, (1989) *Journal of Ethnopharmacology*, 26:147-162.
Yi, S N at al., *Bulletin of Hunan Medical University*, (1988), 13:327-330.
U.S. Pat. No. 6,949,624, Liu et al.
U.S. Patent Publication No. 2004/0197888, Armour et al.
U.S. Patent Publication No. 2004/0253637, Buechler et al.
U.S. Patent Publication No. 2005/0203082, Hsu et al.
U.S. Patent Application No. 2006/0030616A1, filed Feb. 9, 2006 (McCluskey et al.)
Valeriote, F., (1975) *Cancer Chemother. Rep.*, Vol. 59, pp. 895-900.
Wang, G S (1983) *Chin. Pharmac. Bull.*, Col. 18, pp. 18-19.
Wang, G S (1989 *J. Ethnopharmacol.*, Vol. 26, pp. 147-162.
Wang, G S et al. (1986), *Chinese. Pharm. Bull.*, Vol. 21, pp. 90-93.
Wang, G S et al. (1987) *Chinese Pharm. Bull.*, Vol. 22, pp. 517-519.
Waters, C E et al. (2004) *J. Endocrinol.*, Vol. 183, pp. 375-383.
Yoshida, M et al. (1990) *Journal of Biological Chem.*, Vol. 265, No. 28, pp. 17174-17179.
Yung et al. (1996) *Clin. Cancer Res.* Vol. 2, pp. 1931-1935.

What is claimed is:

1. A pharmaceutical composition comprising a compound having the structure

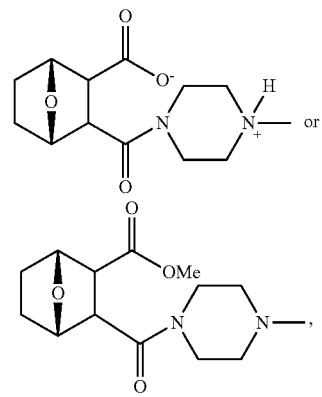

or a pharmaceutically acceptable salt thereof, and a pharmaceutically acceptable carrier.

2. A pharmaceutical composition comprising a compound having the structure

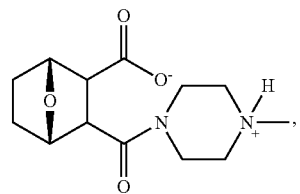

or a pharmaceutically acceptable salt thereof, and a pharmaceutically acceptable carrier.

3. A pharmaceutical composition comprising a compound having the structure

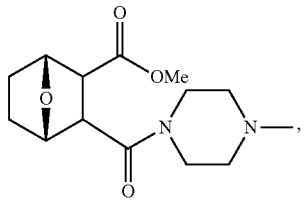 [SMILES: COC(=O)C1C(C(=O)N2CCN(C)CC2)[C@@H]2CC[C@H]1O2]

or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 10,023,587 B2
APPLICATION NO. : 15/425550
DATED : July 17, 2018
INVENTOR(S) : John S. Kovach et al.

It is certified that error appears in the above-identified patent and that said Letters Patent is hereby corrected as shown below:

On the Title Page

In Column 1, item (60), first paragraph, please change to read as follows:
Continuation of application No. 15/275,954, filed on Sep. 26, 2016, now abandoned, which is a continuation of application No. 15/150,129, filed on May 9, 2016, now abandoned, which is a continuation of application No. 15/004,525, filed on Jan. 22, 2016, now abandoned, which is a continuation of application No. 14/794,110, filed on Jul. 8, 2015, now abandoned, which is a continuation of application No. 14/328,384, filed on Jul. 10, 2014, now Pat. No. 9,079,917, which is a division of application No. 13/866,854, filed on Apr. 19, 2013, now Pat. No. 8,822,461, which is a continuation of application No. 13/174,249, filed on Jun. 30, 2011, now Pat. No. 8,426,444, which is a division of application No. 12/069,147, filed on Feb. 6, 2008, now Pat. No. 7,998,957.

Signed and Sealed this
Thirtieth Day of July, 2019

Andrei Iancu
*Director of the United States Patent and Trademark Office*